(12) United States Patent
Anderson et al.

(10) Patent No.: US 8,126,736 B2
(45) Date of Patent: Feb. 28, 2012

(54) METHODS AND SYSTEMS FOR DIAGNOSING, TREATING, OR TRACKING SPINAL DISORDERS

(75) Inventors: Kent Anderson, Sunnyvale, CA (US);
Matthew M Morrison, Cordova, TN (US); Thomas Carls, Memphis, TN (US); Eric Lange, Pleasanton, CA (US); David W Poley, Collierville, TN (US); Patrick Farrell Turner, Winston-Salem, NC (US); Scott James Drapeau, Cordova, TN (US); Michael Allen Ferguson, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 451 days.

(21) Appl. No.: 12/358,425

(22) Filed: Jan. 23, 2009

(65) Prior Publication Data
US 2010/0191071 A1    Jul. 29, 2010

(51) Int. Cl.
*G06Q 50/00* (2006.01)
(52) U.S. Cl. .......................................... 705/2
(58) Field of Classification Search ........... 705/2
See application file for complete search history.

(56) References Cited

U.S. PATENT DOCUMENTS

| | | |
|---|---|---|
| 3,906,931 A | 9/1975 | Terekhov |
| 4,013,074 A | 3/1977 | Siposs |
| 4,214,322 A | 7/1980 | Kraus |
| 4,402,694 A | 9/1983 | Ash et al. |
| 4,505,710 A | 3/1985 | Collins et al. |
| 4,650,492 A | 3/1987 | Barkhordar et al. |
| 4,781,181 A | 11/1988 | Tanguy |
| 4,793,825 A | 12/1988 | Benjamin et al. |
| 4,813,435 A | 3/1989 | Arms |
| 4,945,342 A | 7/1990 | Steinemann |
| 4,971,069 A | 11/1990 | Gracovetsky |
| 4,993,428 A | 2/1991 | Arms |
| 5,016,631 A | 5/1991 | Hogrefe |
| 5,030,236 A | 7/1991 | Dean |

(Continued)

FOREIGN PATENT DOCUMENTS

EP          0119660 A1     9/1984

(Continued)

OTHER PUBLICATIONS

The Montreal Imaging and Orthopedics Research Laboratory; Focus on the LIO and ARGOS; AROGS SpineNews, Apr. 2000, pp. 37-38.

(Continued)

*Primary Examiner* — Gerald J. O'Connor
*Assistant Examiner* — Hiep V. Nguyen

(57) ABSTRACT

A method of patient assessment, treatment, and outcome modeling is disclosed. The method includes obtaining patient characteristic information from a current patient, defining a plurality of therapeutic factors based on the characteristic information of the current patient, and weighting the therapeutic factors. The method also includes accessing at least one database having medical records of prior patients, the medical records including prior patient characteristic information, prior patient treatment plan, and prior patient outcome, comparing the weighted factors of the current patient to the medical records of the prior patients to identify one or more relevant prior patient records, and retrieving at least a portion of the relevant prior patient records, the portion including at least the prior patient treatment plan and the prior patient outcome. The method also includes performing a simulation of at least one of the prior patient treatment plans based on the current patient's characteristic information and selecting a treatment plan for the current patient.

19 Claims, 16 Drawing Sheets

U.S. PATENT DOCUMENTS

| | | |
|---|---|---|
| 5,037,376 A | 8/1991 | Richmond et al. |
| 5,062,856 A | 11/1991 | Sawamura et al. |
| 5,080,682 A | 1/1992 | Schectman |
| 5,083,573 A | 1/1992 | Arms |
| 5,101,814 A | 4/1992 | Palti |
| 5,114,240 A | 5/1992 | Kindt-Larsen et al. |
| 5,125,408 A | 6/1992 | Basser |
| 5,133,773 A | 7/1992 | Sawamura et al. |
| 5,133,774 A | 7/1992 | Sawamura et al. |
| 5,197,488 A | 3/1993 | Kovacevic |
| 5,201,772 A | 4/1993 | Maxwell |
| 5,202,939 A | 4/1993 | Belleville et al. |
| 5,209,240 A | 5/1993 | Jain et al. |
| 5,246,463 A | 9/1993 | Giampapa |
| 5,289,826 A | 3/1994 | Kovacevic |
| 5,306,306 A | 4/1994 | Bisek et al. |
| 5,324,518 A | 6/1994 | Orth et al. |
| 5,337,757 A | 8/1994 | Jain et al. |
| 5,344,446 A | 9/1994 | Sawamura et al. |
| 5,360,016 A | 11/1994 | Kovacevic |
| 5,368,028 A | 11/1994 | Palti |
| 5,374,285 A | 12/1994 | Vaiani et al. |
| 5,376,128 A | 12/1994 | Bozeman |
| 5,383,939 A | 1/1995 | James |
| 5,388,591 A | 2/1995 | De Luca et al. |
| 5,392,119 A | 2/1995 | McArthur et al. |
| 5,421,328 A | 6/1995 | Bedingham |
| 5,425,775 A | 6/1995 | Kovacevic et al. |
| 5,456,724 A | 10/1995 | Yen et al. |
| 5,458,655 A | 10/1995 | Bozeman |
| 5,469,846 A | 11/1995 | Khan |
| 5,470,354 A | 11/1995 | Hershberger et al. |
| 5,480,439 A | 1/1996 | Bisek et al. |
| 5,480,454 A | 1/1996 | Bozeman |
| 5,497,147 A | 3/1996 | Arms et al. |
| 5,533,519 A | 7/1996 | Radke et al. |
| 5,558,640 A | 9/1996 | Pfeiler et al. |
| 5,571,205 A | 11/1996 | James |
| 5,609,162 A | 3/1997 | Blumentritt et al. |
| 5,610,966 A | 3/1997 | Martell et al. |
| 5,694,946 A | 12/1997 | Tenerz et al. |
| 5,695,496 A | 12/1997 | Orsak et al. |
| 5,701,895 A | 12/1997 | Prutchi et al. |
| 5,716,330 A | 2/1998 | Goldman |
| 5,728,281 A | 3/1998 | Hohnström et al. |
| 5,755,675 A | 5/1998 | Sihvonen |
| 5,777,467 A | 7/1998 | Arms et al. |
| 5,810,735 A | 9/1998 | Halperin et al. |
| 5,833,603 A | 11/1998 | Kovacs et al. |
| 5,843,093 A | 12/1998 | Howard |
| 5,853,005 A | 12/1998 | Scanlon |
| 5,873,840 A | 2/1999 | Neff |
| 5,888,212 A | 3/1999 | Petrofsky et al. |
| 5,893,891 A | 4/1999 | Zahedi |
| 5,914,593 A | 6/1999 | Arms et al. |
| 5,935,171 A | 8/1999 | Schneider et al. |
| 5,967,986 A | 10/1999 | Cimochowski et al. |
| 6,001,067 A | 12/1999 | Shults et al. |
| 6,034,295 A | 3/2000 | Rehberg et al. |
| 6,034,296 A | 3/2000 | Elvin et al. |
| 6,056,671 A | 5/2000 | Marmer |
| 6,059,784 A | 5/2000 | Perusek |
| 6,063,046 A | 5/2000 | Allum |
| 6,074,394 A | 6/2000 | Krause |
| 6,092,530 A | 7/2000 | Weissman et al. |
| 6,099,479 A | 8/2000 | Christopherson et al. |
| 6,113,642 A | 9/2000 | Petrofsky et al. |
| 6,120,174 A | 9/2000 | Hoag et al. |
| 6,120,502 A | 9/2000 | Michelson |
| 6,120,540 A | 9/2000 | Apple et al. |
| 6,129,685 A | 10/2000 | Howard |
| 6,134,461 A | 10/2000 | Say et al. |
| 6,140,740 A | 10/2000 | Porat et al. |
| 6,143,035 A | 11/2000 | McDowell |
| 6,161,047 A | 12/2000 | King et al. |
| 6,164,284 A | 12/2000 | Schulman et al. |
| 6,171,239 B1 | 1/2001 | Humphrey |
| 6,185,452 B1 | 2/2001 | Schulman et al. |
| 6,200,265 B1 | 3/2001 | Walsh et al. |
| 6,203,523 B1 | 3/2001 | Haller et al. |
| 6,206,914 B1 | 3/2001 | Soykan et al. |
| 6,212,416 B1 | 4/2001 | Ward et al. |
| 6,227,203 B1 | 5/2001 | Rise et al. |
| 6,230,052 B1 | 5/2001 | Wolff et al. |
| 6,231,527 B1 | 5/2001 | Sol |
| 6,245,109 B1 | 6/2001 | Mendes et al. |
| 6,250,309 B1 | 6/2001 | Krichen et al. |
| 6,259,937 B1 | 7/2001 | Schulman et al. |
| 6,261,280 B1 | 7/2001 | Houben et al. |
| 6,267,724 B1 | 7/2001 | Taylor |
| 6,268,161 B1 | 7/2001 | Han et al. |
| 6,280,604 B1 | 8/2001 | Allen et al. |
| 6,287,452 B1 | 9/2001 | Allen et al. |
| 6,289,251 B1 | 9/2001 | Huepenbecker et al. |
| 6,292,680 B1 | 9/2001 | Somogyi et al. |
| 6,292,702 B1 | 9/2001 | King et al. |
| 6,330,885 B1 | 12/2001 | Weissman et al. |
| 6,344,062 B1 | 2/2002 | Abboudi et al. |
| 6,348,055 B1 | 2/2002 | Preissman |
| 6,398,710 B1 | 6/2002 | Ishikawa et al. |
| 6,402,689 B1 | 6/2002 | Scarantino et al. |
| 6,409,675 B1 | 6/2002 | Turcott |
| 6,415,184 B1 | 7/2002 | Ishikawa et al. |
| 6,416,474 B1 | 7/2002 | Penner et al. |
| 6,416,495 B1 | 7/2002 | Kriesel et al. |
| 6,422,990 B1 | 7/2002 | Prem |
| 6,432,050 B1 | 8/2002 | Porat et al. |
| 6,433,629 B2 | 8/2002 | Hamel et al. |
| 6,437,257 B1 | 8/2002 | Yoshida |
| 6,443,993 B1 | 9/2002 | Koniuk |
| 6,447,448 B1 | 9/2002 | Ishikawa et al. |
| 6,464,671 B1 | 10/2002 | Elver et al. |
| 6,464,687 B1 | 10/2002 | Ishikawa et al. |
| 6,471,645 B1 | 10/2002 | Warkentin et al. |
| 6,473,651 B1 | 10/2002 | Kuzma et al. |
| 6,475,170 B1 | 11/2002 | Doron et al. |
| 6,475,750 B1 | 11/2002 | Han et al. |
| 6,478,824 B1 | 11/2002 | Hagenmeyer |
| 6,482,154 B1 | 11/2002 | Haubrich et al. |
| 6,484,046 B1 | 11/2002 | Say et al. |
| 6,485,462 B1 | 11/2002 | Kriesel |
| 6,486,588 B2 | 11/2002 | Doron et al. |
| 6,493,587 B1 | 12/2002 | Eckmiller et al. |
| 6,494,867 B1 | 12/2002 | Elver et al. |
| 6,497,655 B1 | 12/2002 | Linberg et al. |
| 6,499,368 B2 | 12/2002 | Arms et al. |
| 6,500,210 B1 | 12/2002 | Sabolich et al. |
| 6,502,608 B1 | 1/2003 | Burchett et al. |
| 6,503,249 B1 | 1/2003 | Krause |
| 6,514,219 B1 | 2/2003 | Guimond et al. |
| 6,514,689 B2 | 2/2003 | Han et al. |
| 6,517,585 B1 | 2/2003 | Zahedi et al. |
| 6,527,744 B1 | 3/2003 | Kriesel et al. |
| 6,529,127 B2 | 3/2003 | Townsend et al. |
| 6,530,954 B1 | 3/2003 | Eckmiller |
| 6,533,733 B1 | 3/2003 | Ericson et al. |
| 6,537,233 B1 | 3/2003 | Rangayyan et al. |
| 6,537,250 B1 | 3/2003 | Kriesel |
| 6,549,811 B2 | 4/2003 | Stewart et al. |
| 6,558,321 B1 | 5/2003 | Burd et al. |
| 6,562,001 B2 | 5/2003 | Lebel et al. |
| 6,571,130 B1 | 5/2003 | Ljungström et al. |
| 6,572,543 B1 | 6/2003 | Christopherson et al. |
| 6,573,706 B2 | 6/2003 | Mendes et al. |
| 6,582,365 B1 | 6/2003 | Hines et al. |
| 6,583,630 B2 | 6/2003 | Mendes et al. |
| 6,585,644 B2 | 7/2003 | Lebel et al. |
| 6,585,763 B1 | 7/2003 | Keilman et al. |
| 6,589,172 B2 | 7/2003 | Williams et al. |
| 6,592,518 B2 | 7/2003 | Denker et al. |
| 6,592,519 B1 | 7/2003 | Martinez |
| 6,606,521 B2 | 8/2003 | Paspa et al. |
| 6,610,096 B2 | 8/2003 | MacDonald |
| 6,610,101 B2 | 8/2003 | Herr et al. |
| 6,615,067 B2 | 9/2003 | Hoek et al. |
| 6,621,278 B2 | 9/2003 | Ariav |
| 6,622,567 B1 | 9/2003 | Hamel et al. |

| Patent Number | Date | Inventor(s) |
|---|---|---|
| 6,628,989 B1 | 9/2003 | Penner et al. |
| 6,635,014 B2 | 10/2003 | Starkweather et al. |
| 6,640,137 B2 | 10/2003 | MacDonald |
| 6,641,587 B2 | 11/2003 | Scribner et al. |
| 6,645,143 B2 | 11/2003 | VanTassel et al. |
| 6,645,252 B2 | 11/2003 | Asai et al. |
| 6,648,821 B2 | 11/2003 | Lebel et al. |
| 6,650,919 B2 | 11/2003 | Edelberg et al. |
| 6,652,464 B2 | 11/2003 | Schwartz et al. |
| 6,656,117 B2 | 12/2003 | Jentsch et al. |
| 6,656,135 B2 | 12/2003 | Zogbi et al. |
| 6,656,162 B2 | 12/2003 | Santini et al. |
| 6,658,300 B2 | 12/2003 | Govari et al. |
| 6,659,948 B2 | 12/2003 | Lebel et al. |
| 6,660,042 B1 | 12/2003 | Curcie et al. |
| 6,666,821 B2 | 12/2003 | Keimel |
| 6,667,725 B1 | 12/2003 | Simons et al. |
| 6,669,631 B2 | 12/2003 | Norris et al. |
| 6,673,117 B1 | 1/2004 | Soss et al. |
| 6,679,920 B2 | 1/2004 | Biedermann et al. |
| 6,682,500 B2 | 1/2004 | Soltanpour et al. |
| 6,687,546 B2 | 2/2004 | Lebel et al. |
| 6,692,446 B2 | 2/2004 | Hoek |
| 6,694,191 B2 | 2/2004 | Starkweather et al. |
| 6,695,885 B2 | 2/2004 | Schulman et al. |
| 6,702,847 B2 | 3/2004 | DiCarlo |
| 6,706,005 B2 | 3/2004 | Roy et al. |
| 6,706,071 B1 | 3/2004 | Wolter |
| 6,719,806 B1 | 4/2004 | Zahedi et al. |
| 6,726,678 B1 | 4/2004 | Nelson et al. |
| 6,729,336 B2 | 5/2004 | Silva et al. |
| 6,733,446 B2 | 5/2004 | Lebel et al. |
| 6,733,485 B1 | 5/2004 | Whitehurst et al. |
| 6,740,075 B2 | 5/2004 | Lebel et al. |
| 6,740,123 B2 | 5/2004 | Davalli et al. |
| 6,743,173 B2 | 6/2004 | Penner et al. |
| 6,743,180 B1 | 6/2004 | Van Bockel |
| 6,746,408 B2 | 6/2004 | Krivitski et al. |
| 6,755,870 B1 | 6/2004 | Biedermann et al. |
| 6,758,810 B2 | 7/2004 | Lebel et al. |
| 6,761,741 B2 | 7/2004 | Iesaka |
| 6,764,446 B2 | 7/2004 | Wolinsky et al. |
| 6,792,314 B2 | 9/2004 | Byers et al. |
| 6,802,811 B1 | 10/2004 | Slepian |
| 6,810,290 B2 | 10/2004 | Lebel et al. |
| 6,810,753 B2 | 11/2004 | Valdevit et al. |
| 6,811,533 B2 | 11/2004 | Lebel et al. |
| 6,811,534 B2 | 11/2004 | Bowman et al. |
| 6,821,299 B2 | 11/2004 | Kirking et al. |
| 6,824,512 B2 | 11/2004 | Warkentin et al. |
| 6,824,561 B2 | 11/2004 | Soykan et al. |
| 6,829,507 B1 | 12/2004 | Lidman et al. |
| 6,832,987 B2 | 12/2004 | David et al. |
| 6,845,267 B2 | 1/2005 | Harrison et al. |
| 6,850,635 B2 | 2/2005 | Gerard et al. |
| 6,850,804 B2 | 2/2005 | Eggers et al. |
| 6,856,141 B2 | 2/2005 | Ariav |
| 6,862,479 B1 | 3/2005 | Whitehurst et al. |
| 6,873,268 B2 | 3/2005 | Lebel et al. |
| 6,875,208 B2 | 4/2005 | Santini et al. |
| 6,878,112 B2 | 4/2005 | Linberg et al. |
| 6,889,165 B2 | 5/2005 | Lind et al. |
| 6,908,488 B2 | 6/2005 | Passivaara et al. |
| 6,918,308 B2 | 7/2005 | Biedermann et al. |
| 6,918,873 B1 | 7/2005 | Millar et al. |
| 6,922,590 B1 | 7/2005 | Whitehurst |
| 6,923,817 B2 | 8/2005 | Carson et al. |
| 6,941,171 B2 | 9/2005 | Mann et al. |
| 6,949,075 B2 | 9/2005 | Hatlesad et al. |
| 6,950,707 B2 | 9/2005 | Whitehurst |
| 6,952,687 B2 | 10/2005 | Andersen et al. |
| 6,962,568 B1 | 11/2005 | Morger |
| 6,965,791 B1 | 11/2005 | Hitchcock et al. |
| 6,969,360 B1 | 11/2005 | Pai et al. |
| 6,969,382 B2 | 11/2005 | Richter |
| 6,974,437 B2 | 12/2005 | Lebel et al. |
| 6,976,982 B2 | 12/2005 | Santini et al. |
| 6,980,865 B1 | 12/2005 | Wang et al. |
| 6,984,993 B2 | 1/2006 | Ariav |
| 6,987,982 B2 | 1/2006 | Willenegger et al. |
| 7,001,346 B2 | 2/2006 | White |
| 7,001,372 B2 | 2/2006 | Richter |
| 7,001,393 B2 | 2/2006 | Schwenke et al. |
| 7,018,089 B2 | 3/2006 | Wenz et al. |
| 7,020,531 B1 | 3/2006 | Colliou et al. |
| 7,022,072 B2 | 4/2006 | Fox et al. |
| 7,024,249 B2 | 4/2006 | Weisner et al. |
| 7,025,760 B2 | 4/2006 | Miller et al. |
| 7,027,874 B1 | 4/2006 | Sawan et al. |
| 7,029,500 B2 | 4/2006 | Martin |
| 7,043,295 B2 | 5/2006 | Starkebaum |
| 7,044,911 B2 | 5/2006 | Drinan et al. |
| 7,052,488 B2 | 5/2006 | Uhland |
| 7,060,031 B2 | 6/2006 | Webb et al. |
| 7,061,523 B2 | 6/2006 | Fujita et al. |
| 7,063,691 B2 | 6/2006 | Nelson et al. |
| 7,070,591 B2 | 7/2006 | Adams et al. |
| 7,076,305 B2 | 7/2006 | Imran et al. |
| 7,079,881 B2 | 7/2006 | Schulman et al. |
| 7,097,662 B2 | 8/2006 | Evans et al. |
| 7,107,832 B2 | 9/2006 | Blumentritt et al. |
| 7,115,096 B2 | 10/2006 | Siejko et al. |
| 7,118,601 B2 | 10/2006 | Yasui et al. |
| 7,120,498 B2 | 10/2006 | Imran et al. |
| 7,122,027 B2 | 10/2006 | Trescony et al. |
| 7,125,382 B2 | 10/2006 | Zhou et al. |
| 7,131,998 B2 | 11/2006 | Pasolini |
| 7,134,999 B2 | 11/2006 | Brauker et al. |
| 7,137,998 B2 | 11/2006 | Bédard |
| 7,147,667 B2 | 12/2006 | Bédard |
| 7,151,961 B1 | 12/2006 | Whitehurst et al. |
| 7,155,284 B1 | 12/2006 | Whitehurst et al. |
| 7,174,199 B2 | 2/2007 | Berner et al. |
| 7,174,206 B2 | 2/2007 | Frei et al. |
| 7,195,645 B2 | 3/2007 | Disilvestro et al. |
| 7,234,180 B2 | 6/2007 | Horton et al. |
| 2002/0007198 A1 | 1/2002 | Haupert et al. |
| 2002/0010390 A1 | 1/2002 | Guice et al. |
| 2002/0016568 A1 | 2/2002 | Lebel et al. |
| 2002/0024450 A1 | 2/2002 | Townsend et al. |
| 2002/0045804 A1 | 4/2002 | Christopherson et al. |
| 2002/0045921 A1 | 4/2002 | Wolinsky et al. |
| 2002/0052539 A1 | 5/2002 | Haller et al. |
| 2002/0055779 A1 | 5/2002 | Andrews |
| 2002/0062143 A1 | 5/2002 | Baudino et al. |
| 2002/0065454 A1 | 5/2002 | Lebel et al. |
| 2002/0072656 A1 | 6/2002 | Vantassel et al. |
| 2002/0082583 A1 | 6/2002 | Lerner |
| 2002/0091310 A1 | 7/2002 | Jentsch et al. |
| 2002/0099359 A1 | 7/2002 | Santini et al. |
| 2002/0103543 A1 | 8/2002 | Asai et al. |
| 2002/0111542 A1 | 8/2002 | Warkentin et al. |
| 2002/0115944 A1 | 8/2002 | Mendes et al. |
| 2002/0120332 A1 | 8/2002 | Law et al. |
| 2002/0123672 A1 | 9/2002 | Christopherson et al. |
| 2002/0123673 A1 | 9/2002 | Webb et al. |
| 2002/0123674 A1 | 9/2002 | Plicchi et al. |
| 2002/0137991 A1 | 9/2002 | Scarantino et al. |
| 2002/0138153 A1 | 9/2002 | Koniuk |
| 2002/0173702 A1 | 11/2002 | Lebel et al. |
| 2002/0173703 A1 | 11/2002 | Lebel et al. |
| 2002/0173723 A1 | 11/2002 | Lewis et al. |
| 2002/0177790 A1 | 11/2002 | Meredith et al. |
| 2002/0191487 A1 | 12/2002 | Sand |
| 2002/0198513 A1 | 12/2002 | Lebel et al. |
| 2002/0198526 A1 | 12/2002 | Shaolian et al. |
| 2003/0004438 A1 | 1/2003 | Berthonnaud et al. |
| 2003/0009221 A1 | 1/2003 | Forseil |
| 2003/0023319 A1 | 1/2003 | Andersen et al. |
| 2003/0028079 A1 | 2/2003 | Lebel et al. |
| 2003/0028080 A1 | 2/2003 | Lebel et al. |
| 2003/0040806 A1 | 2/2003 | MacDonald |
| 2003/0050535 A1 | 3/2003 | Bowman et al. |
| 2003/0055406 A1 | 3/2003 | Lebel et al. |
| 2003/0065308 A1 | 4/2003 | Lebel et al. |
| 2003/0069644 A1 | 4/2003 | Kovacevic et al. |
| 2003/0078560 A1 | 4/2003 | Miller et al. |
| 2003/0078643 A1 | 4/2003 | Schulman et al. |

| Publication No. | Date | Inventor |
|---|---|---|
| 2003/0114735 A1 | 6/2003 | Silver et al. |
| 2003/0114905 A1 | 6/2003 | Kuzma |
| 2003/0120150 A1 | 6/2003 | Govari |
| 2003/0120458 A1 | 6/2003 | Rao et al. |
| 2003/0120514 A1 | 6/2003 | Rao et al. |
| 2003/0125988 A1 | 7/2003 | Rao et al. |
| 2003/0126101 A1 | 7/2003 | Rao et al. |
| 2003/0136417 A1 | 7/2003 | Fonseca et al. |
| 2003/0139690 A1 | 7/2003 | Aebli et al. |
| 2003/0139778 A1 | 7/2003 | Fischell et al. |
| 2003/0139783 A1 | 7/2003 | Kilgore et al. |
| 2003/0181791 A1 | 9/2003 | Thomas et al. |
| 2003/0181794 A1 | 9/2003 | Rini et al. |
| 2003/0181830 A1 | 9/2003 | Guimond et al. |
| 2003/0195396 A1 | 10/2003 | Scarantino et al. |
| 2003/0204181 A1 | 10/2003 | Starkebaum |
| 2003/0208109 A1 | 11/2003 | David et al. |
| 2004/0011137 A1 | 1/2004 | Hnat et al. |
| 2004/0019382 A1 | 1/2004 | Amirouche et al. |
| 2004/0021322 A1 | 2/2004 | Ariav |
| 2004/0034332 A1 | 2/2004 | Uhland |
| 2004/0054352 A1 | 3/2004 | Adams et al. |
| 2004/0054423 A1 | 3/2004 | Martin |
| 2004/0059315 A1 | 3/2004 | Erickson et al. |
| 2004/0059423 A1 | 3/2004 | Barnes et al. |
| 2004/0064133 A1 | 4/2004 | Miller et al. |
| 2004/0064195 A1 | 4/2004 | Herr |
| 2004/0068205 A1 | 4/2004 | Zogbi et al. |
| 2004/0073093 A1 | 4/2004 | Hatlestad |
| 2004/0078027 A1 | 4/2004 | Shachar |
| 2004/0078236 A1 * | 4/2004 | Stoodley et al. .................. 705/2 |
| 2004/0113790 A1 | 6/2004 | Hamel et al. |
| 2004/0121486 A1 | 6/2004 | Uhland et al. |
| 2004/0129095 A1 | 7/2004 | Churchill et al. |
| 2004/0147816 A1 | 7/2004 | Policker et al. |
| 2004/0147906 A1 | 7/2004 | Voyiazis et al. |
| 2004/0152972 A1 | 8/2004 | Hunter |
| 2004/0158232 A1 | 8/2004 | Schetky et al. |
| 2004/0186396 A1 | 9/2004 | Roy et al. |
| 2004/0199059 A1 | 10/2004 | Brauker et al. |
| 2004/0204647 A1 | 10/2004 | Grupp et al. |
| 2004/0204744 A1 | 10/2004 | Penner et al. |
| 2004/0207409 A1 | 10/2004 | Ariav et al. |
| 2004/0215299 A1 | 10/2004 | Zhao et al. |
| 2004/0228510 A1 | 11/2004 | Berthonnaud et al. |
| 2004/0236192 A1 | 11/2004 | Shehada et al. |
| 2004/0236395 A1 | 11/2004 | Iaizzo et al. |
| 2004/0243148 A1 | 12/2004 | Wasielewski |
| 2004/0243207 A1 | 12/2004 | Olson et al. |
| 2004/0260156 A1 | 12/2004 | David et al. |
| 2005/0010299 A1 | 1/2005 | DiSilvestro |
| 2005/0010300 A1 | 1/2005 | DiSilvestro et al. |
| 2005/0010302 A1 | 1/2005 | Dietz et al. |
| 2005/0012610 A1 | 1/2005 | Liao et al. |
| 2005/0012617 A1 | 1/2005 | DiSilvestro et al. |
| 2005/0027175 A1 | 2/2005 | Yang |
| 2005/0027192 A1 | 2/2005 | Govari et al. |
| 2005/0033132 A1 | 2/2005 | Shults et al. |
| 2005/0033133 A1 | 2/2005 | Kraft |
| 2005/0043594 A1 | 2/2005 | Dinsmoor et al. |
| 2005/0049578 A1 | 3/2005 | Tu et al. |
| 2005/0055014 A1 | 3/2005 | Coppeta et al. |
| 2005/0064009 A1 | 3/2005 | Bates |
| 2005/0090866 A1 | 4/2005 | Miller et al. |
| 2005/0099290 A1 | 5/2005 | Govari |
| 2005/0101843 A1 | 5/2005 | Quinn et al. |
| 2005/0119713 A1 | 6/2005 | Whitehurst et al. |
| 2005/0134452 A1 | 6/2005 | Smith |
| 2005/0137626 A1 | 6/2005 | Pastore et al. |
| 2005/0154374 A1 | 7/2005 | Hunter et al. |
| 2005/0165317 A1 | 7/2005 | Turner et al. |
| 2005/0177097 A1 | 8/2005 | Hildebrand et al. |
| 2005/0177135 A1 | 8/2005 | Hildebrand et al. |
| 2005/0183954 A1 | 8/2005 | Hitchcock et al. |
| 2005/0186245 A1 | 8/2005 | Hunter et al. |
| 2005/0215871 A1 | 9/2005 | Feldman et al. |
| 2005/0234307 A1 | 10/2005 | Heinonen et al. |
| 2005/0234555 A1 | 10/2005 | Sutton et al. |
| 2005/0245821 A1 | 11/2005 | Govari et al. |
| 2005/0247319 A1 | 11/2005 | Berger |
| 2005/0267440 A1 | 12/2005 | Herman et al. |
| 2005/0267597 A1 | 12/2005 | Flaherty et al. |
| 2005/0272990 A1 | 12/2005 | Ariav et al. |
| 2005/0283198 A1 | 12/2005 | Haubrich et al. |
| 2005/0288596 A1 | 12/2005 | Eigler et al. |
| 2005/0288604 A1 | 12/2005 | Eigler et al. |
| 2005/0288722 A1 | 12/2005 | Eigler et al. |
| 2006/0004417 A1 | 1/2006 | Rossing et al. |
| 2006/0004431 A1 | 1/2006 | Fuller et al. |
| 2006/0009856 A1 | 1/2006 | Sherman et al. |
| 2006/0015020 A1 | 1/2006 | Neale et al. |
| 2006/0015470 A1 | 1/2006 | Lauer et al. |
| 2006/0017576 A1 | 1/2006 | Gordon et al. |
| 2006/0030914 A1 | 2/2006 | Eggers et al. |
| 2006/0032314 A1 | 2/2006 | Hnat et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036301 A1 | 2/2006 | Eggers et al. |
| 2006/0036323 A1 | 2/2006 | Carl et al. |
| 2006/0036324 A1 | 2/2006 | Sachs et al. |
| 2006/0041183 A1 | 2/2006 | Massen et al. |
| 2006/0047283 A1 | 3/2006 | Evans et al. |
| 2006/0052782 A1 | 3/2006 | Morgan et al. |
| 2006/0057737 A1 | 3/2006 | Santini et al. |
| 2006/0058588 A1 | 3/2006 | Zdeblick |
| 2006/0069436 A1 | 3/2006 | Sutton et al. |
| 2006/0069447 A1 | 3/2006 | DiSilvestro et al. |
| 2006/0074449 A1 | 4/2006 | Denker et al. |
| 2006/0079740 A1 | 4/2006 | Silver et al. |
| 2006/0079858 A1 | 4/2006 | Miller et al. |
| 2006/0087325 A1 | 4/2006 | Ariav et al. |
| 2006/0095020 A1 | 5/2006 | Casas et al. |
| 2006/0100508 A1 | 5/2006 | Morrison |
| 2006/0155385 A1 | 7/2006 | Martin |
| 2006/0173444 A1 | 8/2006 | Choy et al. |
| 2006/0178617 A1 | 8/2006 | Adams et al. |
| 2006/0183979 A1 | 8/2006 | Rini et al. |
| 2006/0189854 A1 | 8/2006 | Webb et al. |
| 2006/0200010 A1 * | 9/2006 | Rosales et al. ................. 600/300 |
| 2006/0200022 A1 | 9/2006 | Brauker et al. |
| 2006/0211914 A1 | 9/2006 | Hassler et al. |
| 2006/0211921 A1 | 9/2006 | Brauker et al. |
| 2006/0212082 A1 | 9/2006 | Svanerudh |
| 2006/0224088 A1 | 10/2006 | Roche |
| 2006/0224108 A1 | 10/2006 | Brauker et al. |
| 2006/0229534 A1 | 10/2006 | Chang et al. |
| 2006/0235472 A1 | 10/2006 | Goetz et al. |
| 2006/0247773 A1 | 11/2006 | Stamp |
| 2006/0253005 A1 | 11/2006 | Drinan et al. |
| 2006/0263763 A1 | 11/2006 | Simpson et al. |
| 2006/0271199 A1 | 11/2006 | Johnson |
| 2006/0282062 A1 | 12/2006 | Ishikawa et al. |
| 2006/0283465 A1 | 12/2006 | Nickel et al. |
| 2007/0005042 A1 | 1/2007 | Anderson |
| 2007/0005145 A1 | 1/2007 | Banks et al. |
| 2007/0016163 A1 | 1/2007 | Santini et al. |
| 2007/0027370 A1 | 2/2007 | Brauker et al. |
| 2007/0032706 A1 | 2/2007 | Kamath et al. |
| 2007/0156453 A1 * | 7/2007 | Frielinghaus et al. ............ 705/2 |

FOREIGN PATENT DOCUMENTS

| | | |
|---|---|---|
| EP | 0619101 A1 | 10/1994 |
| EP | 1285640 A2 | 2/2003 |
| EP | 1442715 A2 | 8/2004 |
| WO | WO0038599 A1 | 7/2000 |
| WO | WO0150956 A1 | 7/2001 |
| WO | WO03048688 A2 | 6/2003 |
| WO | WO03061467 A1 | 7/2003 |
| WO | WO03061504 A1 | 7/2003 |
| WO | WO2004014456 A2 | 2/2004 |
| WO | WO2005062719 A2 | 7/2005 |
| WO | WO2005120167 A2 | 12/2005 |
| WO | WO2007001624 A2 | 1/2007 |

OTHER PUBLICATIONS

Rapp, Susan M.; Ortho Supersite; Orthopedic Surgeons and Rheumatologists only; Business of Orthopedics; Smart implants to provide biofeedback, measure joint loads, detect infection; Orthopedics Today 2008, (3 pages).

Dumas, R., et al., Finite element simulation of spinal deformities correction by in situ contouring technique, Computer Methods in Biomechanics and Biomedical Engineering, vol. 8, Issue 5, pp. 331-337, Oct. 2005 (Abstract only, 1 page).

Breau, C., et al; BioMEMS and Biomedical Nanotechnology, SpringerLink Journal, Dec. 6, 1990 (Abstract only,1 page).

Papin, P., et al.; Hand Transplantation, SpringerLink Journal, (Abstract only, 2 pages).

Eberlein, R., et al.; SpringerLink Journal, Apr. 2004 (Abstract only, 1 page).

Aubin, C.E., et al.; Deformable Models, SpringerLink Journal, Sep. 2003 (Abstract only, 1 page).

Rajamani, K.T., et al.; Bone Model Morphing for Enhanced Surgical Visualization; Biomedical Imaging: Nano to Macro, Apr. 2004, IEEE International Symposium, (Summary only, 1 page).

Zebris, zebris Force Measuring Platform, The World of Biomechanics, zebris Medical GmbH, Max-Eyth-Weg 42 (1 page).

Zebris, zebris Real Time Motion Analysis, The World of Biomechanics, zebris Medical GmbH, Max-Eyth-Weg 42 (1 page).

\* cited by examiner

Lumbar Disc Herniation Treatment Options

48 — Spinal Disorder

Lumbar Disc Herniation

50 — Treatment Options (Select At Least One)

- ☑ Option 1 — Fusion Cages
- ☑ Option 2 — Anterior Lumbar Interbody Fusion
- ☐ Option 3 — Posterior Lumbar Interbody Fusion
- ☐ Option 4 — Transforamental Lumbar Interbody Fusion
- ☐ Option 5 — Intradiscal Electrothermal Therapy
- ☐ Option 6 — Laminotomy
- ☐ Option 7 — Laparoscopic Fusion
- ☑ Option 8 — Artificial Disc Replacement Back    Next

*Fig. 8*

METHODS AND SYSTEMS FOR DIAGNOSING, TREATING, OR TRACKING SPINAL DISORDERS

FIELD/BACKGROUND

The present disclosure is directed to improved systems and methods for diagnosing, treating, and/or tracking medical conditions. More particularly, in some aspects the present disclosure is directed to systems and methods for diagnosing, treating, and/or tracking spinal disorders.

In addition to the areas that are scientific in nature, a significant portion of the practice of medicine is artistic in nature. The medical professional studies at length the biology, physiology and other disciplines related to his or her preferred medical specialty or practice, and thereafter may reference the scientific work of others for assistance. Further, he or she may have specific data obtained from measurements or assessments of the particular patient by way of x-rays, thermometers, electrocardiograms, and/or other devices and machines. Even though the data obtained may be undisputed, in many cases the root problem may not be entirely clear. Further, even where the root problem is clear there may be several possible treatment options. Accordingly, the physician or other medical professional will rely on experience, skill, and intuition to come to a conclusion as to what the most effective treatment may be for the patient.

While decisions based on experience, skill, and intuition are successful in many instances, in other instances these decisions result in a course of treatment that is less effective than had been hoped. In such cases, the patient may continue to be subjected to discomfort during the less-effective treatment, or a condition may worsen. Additionally, as medical procedures and devices become more expensive and time-consuming, it becomes more important to achieve a successful patient outcome in the first place from a resource-conservation standpoint as well. Accordingly, there is a need for improved devices, systems, and methods for diagnosing, treating, and/or tracking medical problems. For example and without limitation, there remains a need for improved devices, systems, and methods for diagnosing, treating, and/or tracking spinal disorders.

SUMMARY

The present disclosure provides devices, systems, and methods for diagnosing, treating, and/or tracking medical conditions and, in particular, spinal disorders.

In certain embodiments, a method of pathology assessment, treatment, and outcome modeling is provided. The method includes obtaining information from a patient concerning at least one of the patient's characteristics, and defining one or more possible therapeutic outcomes, thereby creating a plurality of therapeutic factors, and weighting the factors. Accessing at least one database having records of prior treatments of patients having similar characteristics, pathologies, and/or therapeutic outcomes and comparing the factors to information in the records. In at least one embodiment, the most relevant of the records is identified according to the weighted factors and at least a portion of each of the records is retrieved from the database. In some instances, the portion of the records obtained includes information regarding an administered treatment plan. A simulation and/or outcome modeling of each administered treatment from the records obtained is performed to obtain a level of confidence in a particular outcome resulting from said treatment. Based on the simulation and/or outcome modeling a treatment plan for the current patient is selected. The database includes information collected from one or more medical treatment studies. In some instances, the medical treatment studies include general spinal treatment and outcome studies, spine trauma studies, lumbar spine studies, cervical spine studies, spinal deformity studies, and/or other studies. In some embodiments, the database also includes patient characteristic, measurement, and pathology information, including information from diagnostic tests. In some embodiments, some or all of the steps of the method are performed electronically, such as over a computer network. The selected treatment for the patient and its outcome are provided to a database and/or a medical study in some instances. In some embodiments, the prior treatments and the administered treatments include spinal surgical procedures.

In another embodiment, a system for pathology assessment, treatment and outcome modeling includes a database having a series of records of patient treatments, the records including patient measurement information, treatment information, and outcome information. In one aspect, the system also includes at least one processor operatively connected to the database and into which a set of information of a current patient is entered and weighted. In some instances, the processor is programmed to compare the current patient information to the database information and to output information from records in the database with similar information sets to the current patient information. The outputted information includes treatment information and outcome information. In some embodiments, the at least one processor is programmed to simulate treatment options and/or model outcomes. The processor is programmed for use with item response theory models to compare said current patient information to the database information in some embodiments. In some instances, the processor is part of a computer or a computer network and in some embodiments includes multiple processors at a single or multiple locations.

In another embodiment, a method for pathology assessment, treatment and outcome modeling includes obtaining a plurality of therapeutic factors from a current patient, including information of at least one of the patient's characteristics, the patient's pathology, and one or more possible therapeutic outcomes, weighting the factors, accessing at least one database having records of prior treatments for patients having similar pathologies, comparing the factors to information in the records, retrieving from one or more of the records most relevant to the weighted factors, at least a portion of each of the records, the portions including information regarding the outcome of an administered treatment, and selecting a treatment for the current patient based at least in part on said outcome information. The weighting of the factors varies in some instances based on the preferences of the practitioner, the hypothesized pathology, experience, and/or other factors. The treatment may be performed on the current patient and the database may be updated with information regarding the patient's treatment and outcome.

In another embodiment, a method for identifying available treatment options for a patient having an increased likelihood of success is provided. The method includes obtaining a plurality of therapeutic factors from a current patient. The factors are based at least partially on the current patient's physical characteristics, pathology, and desired therapeutic outcomes. The method also includes weighting the therapeutic factors and accessing at least one database having records of prior patient treatments. The records including prior patient therapeutic factors, treatment plans, and treatment outcomes. The method also includes comparing the therapeutic factors of the current patient with the prior patient therapeutic factors in the records of the database to identify prior patients with similar therapeutic factors and retrieving from the database at least a portion of one or more records of prior patients with similar therapeutic factors. Finally, the method includes identifying available treatment options for the current patient based at least in part on the records of the prior patients with similar therapeutic factors.

In another embodiment, a system for identifying available treatment options for a current patient having an increased likelihood of success is provided. The system includes at least one local database having a plurality of records of prior local patients. The records of the prior local patients includes patient characteristic information, treatment information, and outcome information. The system also includes at least one remote database having a plurality of records of prior remote patients. The records of the prior remote patients includes patient characteristic information, treatment information, and outcome information. The system also includes at least one processing system operatively connected to the local and remote databases. The at least one processing system includes a diagnostic module, a modeling module, and a treatment module. The diagnostic module is configured to receive and weight current patient information, compare the current patient information to the plurality of records of in the local and remote databases, and retrieve records of prior patients with similar characteristic information from the local and remote databases. The treatment module is configured to identify available treatment options for the current patient based at least partially on the records retrieved from the local and remote databases by the diagnostic module. The modeling module is configured to simulate the available treatment options for the current patient identified by the treatment module. The simulation is at least partially based on the outcome information from the records of prior patients retrieved from the local and remote databases.

In another embodiment, a method for identifying available treatment options is provided. The method includes accessing at least one database having records of prior patients. The records include prior patient treatment plans and treatment outcomes. The method also includes identifying prior patients with similar characteristics to a current patient and retrieving from the database at least a portion of the records of prior patients with similar characteristics to the current patient. The portion of the records retrieved includes the treatment plans and treatment outcomes of the prior patients with similar characteristics. Finally, the method includes identifying successful treatment plans of prior patients based on the treatment outcomes.

In another embodiment, a method of obtaining and analyzing patient information for diagnosis and treatment is provided. The method includes identifying at least one patient symptom and selecting at least one patient category associated with the at least one patient symptom. The method also includes obtaining data corresponding to the at least one patient category. The method also provides the obtained data to a software application. The software application analyzes the obtained data. The method also includes providing a summary of the software application analysis for use in diagnosing the patient's medical condition and identifying available treatment options.

In another embodiment, a method of obtaining and analyzing patient information for diagnosis and treatment is provided. The method includes submitting a patient to diagnostic testing and obtaining results from the diagnostic testing. The method also includes categorizing the patient based on the results from the diagnostic testing. The method also includes obtaining additional data regarding the patient. In some instances, the additional data is associated with the categorization of the patient. The method also includes providing the obtained data and the results from the diagnostic testing to a software application and analyzing the obtained data and results from the diagnostic testing with the software application. The method also includes identifying at least one available treatment option for the patient based on the analysis.

In another embodiment, a method of visualizing and analyzing anatomical motion is provided. The method includes providing a plurality of implantable sensors. Each of the plurality of implantable sensors is configured for implantation adjacent to an anatomical feature of a patient. The method also includes tracking the positions of the implantable sensors as the patient is put through a diagnostic motion protocol. The method also includes correlating the positions of the implantable sensors to the positions of the anatomical features of the patient adjacent to the sensors. A motion sequence of the anatomical features is visualized according to the positions of the anatomical features from the diagnostic motion protocol. Finally, the method includes analyzing the motion sequence of the anatomical features to identify a medical problem.

In another embodiment, a system for visualizing and analyzing anatomical motion is provided. The system includes a plurality of implantable sensors. Each of the plurality of implantable sensors is configured for implantation adjacent to an anatomical feature of a patient. The system also includes a monitoring system in communication with the implantable sensors. The monitoring system is configured to track the positions of the sensors within the patient during a diagnostic motion protocol. The system also includes at least one processing system in communication with the monitoring system. The at least one processing system includes a modeling module configured to create an animated model of the patient's anatomical features based at least partially on the positions of the sensors as tracked by the monitoring system during the diagnostic motion protocol. In some instances, a marker-less or sensor-less tracking system is utilized. For example, in one embodiment a plurality of cameras track the patient's motion from different angles. The resultant images from the cameras are then combined to create 3-D reconstructions of the motion, which are then mapped to models of the patient's anatomical features.

In another embodiment, a method of performing a surgical procedure using implantable sensors is provided. The method includes providing one or more implantable sensors. Each of the sensors is configured for implantation adjacent to an anatomical feature of a patient. The method also includes imaging the patient to determine the relative positions of the one or more implantable sensors relative to the anatomical features of the patient. The method also includes inserting an implant adjacent to at least one of the anatomical features and tracking the position of the implant relative to the at least one anatomical feature during the inserting of the implant using the implantable sensors.

In another embodiment, a method of inserting a spinal implant is disclosed. The method includes providing at least one sensor. The at least one sensor is positioned within a housing having a bone engaging portion and an asymmetrical head portion. The method also includes engaging the bone engaging portion of the housing with a vertebra. The patient is imaged to determine the relative position of the sensor relative to the vertebra using the asymmetrical head portion of the housing as a guide. The method also includes inserting an implant adjacent to the vertebra. Finally, the method includes tracking the position of the implant relative to the vertebra by correlating the relative position of the implant to the sensor to the vertebra.

In another embodiment, a method of selecting implant parameters is provided. The method includes introducing one or more sensors adjacent to an anatomical feature and monitoring a motion sequence of the anatomical feature with the one or more sensors. The method also includes analyzing the monitored motion sequence of the anatomical feature to detect a problem in the motion sequence of the anatomical feature. Finally, the method includes determining a parameter for an implant for at least partially correcting the problem in the motion sequence of the anatomical feature.

In another embodiment, a method of selecting a spinal implant and its parameters is provided. The method includes introducing a plurality of sensors adjacent to a pair of vertebrae defining a spinal joint and monitoring a motion sequence of the spinal joint with the plurality of sensors. The method also includes analyzing the monitored motion sequence of the vertebrae to detect an initial problem in the motion sequence of the spinal joint. The method includes determining a parameter for an implant for correcting the initial problem in the motion sequence of the spinal joint. Finally, the method also includes identifying at least one spinal implant with the parameter for correcting the initial problem in the motion sequence of the spinal joint.

In another embodiment, a method of detecting implant loosening is provided. The method includes providing an implant for fixedly engaging with an anatomical feature of a patient. The implant has a first sensor secured thereto. The method also includes tracking a first motion pattern of the first sensor and tracking a second motion pattern of a second sensor secured to the anatomical feature. The method also includes determining a relative motion between the first sensor and the second sensor based on the first and second motion patterns. Finally, the method includes identifying implant loosening by analyzing the relative motion between the first sensor and the second sensor.

In another embodiment, a method of detecting implant loosening is provided. The method includes inserting a first sensor into a bone structure and securing the first sensor in a fixed position with respect to the bone structure. The method also includes engaging an implant with at least a portion of the bone structure. The implant has a second sensor positioned therein. The method also includes securing the implant with the portion of the bone structure such that the second sensor is substantially fixed with respect to the bone structure and the first sensor. Finally, the method includes monitoring the position of the second sensor with respect to the first sensor to identify implant loosening.

Further aspects, forms, embodiments, objects, features, benefits, and advantages of the present disclosure shall become apparent from the detailed drawings and descriptions provided herein.

BRIEF DESCRIPTION OF THE DRAWINGS

FIG. 8 is an exemplary screen shot of a software interface that is utilized as part of the identification step of the method of FIG. 2 according to one embodiment of the present disclosure.

DETAILED DESCRIPTION

Figure 1:
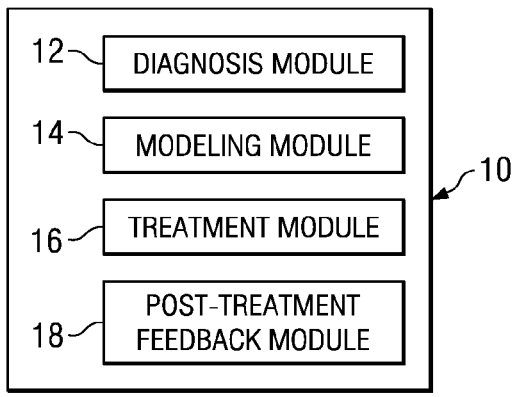
FIG. 1 is a diagrammatic schematic view of a system for use in treating a patient according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications in the described devices, instruments, methods, and any further application of the principles of the disclosure as described herein are contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure.

Referring to FIG. 1, shown therein is a diagrammatic schematic view of a system 10 for use in treating a patient according to a first embodiment of the present disclosure. Among other aspects, the system 10 is used by medical professionals and other medical personnel for assisting them in making decisions on treatments aimed at the desired clinical outcomes for the patient. The system 10 includes methods for coordinating a number of sources of data and assimilating the relevant data to provide actionable information for the medical personnel. Using such information with the appropriate confidence intervals, the medical personnel develop a clinical decision on an appropriate treatment plan based on data of actual patient outcomes relating to identical or similar treatments. In particular embodiments, the data analysis takes the form of an item response theory (IRT) modelization technique that allows medical personnel to compare the patient's symptoms to previous patients having similar symptoms, and then identify the treatments and corresponding outcomes for the previously treated patients. The previous patient outcomes are conditioned or weighted based on a probabilistic treatment result. Based on the available data, the system 10 objectively decides one or more of the variable or "trade-off" decisions typically performed by skilled professionals that are used to select among a plurality of different treatment options.

In some instances, the system 10 is continuously optimized by tracking patient outcomes with the corresponding treatment plans and modifying treatment plans for future patients accordingly. In that regard, in some instances the system 10 utilizes fuzzy logic and/or genetic algorithms for correlating future patient symptoms with prior patient symptoms and outcomes to identify the best treatment plan for the patient based on desired outcomes. In that regard, patient outcome goals may include, without limitation, a particular Oswestry disability form and score (ODI), overall patient satisfaction with treatment, reduction or elimination of symptoms (e.g., pain, limited mobility, etc.), improved score on Neck Disability Index (NDI), improved SF-36 (Short Form 36) score, improved HRQL (Health Related Quality of Life) score, restoration or improvement of quality of life, and/or other factors. More particularly, where surgical treatments are undertaken the outcome goals may include, without limitation, restoration or improvement of mobility, restoration or improvement of range of motion, restoration or improvement of balance in the sagittal and/or coronal planes, restoration or improvement of center of gravity, preservation of healthy anatomy (ligaments, cartilage, bony anatomy, etc.), restoration or improvement of gait, and/or other factors. In addition to the patient specific surgical outcome goals, the present disclosure provides methods and systems for improving aspects of surgical procedures in general including, without limitation, improved cosmesis (particularly muscular and skin incision in some instances), reduced harvest morbidity, reduced need for harvests (BMP), reduced morbidity, reduced complications, reduced cost of surgery, reduced time in operating room, reduced recovery time, reduced blood loss, reduced likelihood of revision surgery, reduced likelihood of adjacent level disc disease, reduced adjacent organ restrictions or impairment (e.g., lung) caused by trauma or extreme deformity, and/or other factors.

While the systems and methods disclosed herein will be described in the context of orthopedic treatments and, in particular, with surgical orthopedic treatments of the spine, it is understood that systems and/or methods similar to those described herein are useful for diagnosing and treating patients in numerous other medical fields, including but not limited to cardiology and oncology. Further, while the treatment plans discussed herein will be focused on surgical procedures, the treatment plans also include non-invasive treatments, such as physical therapy protocols, in addition to or in lieu of the surgical procedures in some embodiments. Similarly, the treatment plans also include medicinal treatments as well in some embodiments.

Referring again to FIG. 1, the system 10 includes a diagnosis module 12, a modeling module 14, a treatment module 16, and a post-treatment feedback module 18. In some embodiments, the system 10 is a spinal disorder diagnostic and treatment system. In that regard, the system 10 is utilized by physicians, surgeons, medical assistants, and/or other medical personnel to diagnose motion disorders, model patient-specific treatment plans, plan and deliver treatment to the patient, acquire feedback regarding the effectiveness of the treatment, modify the treatment as needed, track patient results based on treatment plans, and/or continuously improve patient treatment by correlating successful treatment plans with specific patient symptoms or characteristics related to the motion disorders. As described below, the system 10 provides communication between medical personnel (physicians, surgeons, therapists, medical assistants, etc.), patients, and/or medical device manufacturers. Also, the system 10 is particularly adapted for providing a platform for executing the methods described below. Additional details regarding the modules 12, 14, 16, and 18 of the system 10 will be described in more detail below in relation to these methods. Other uses of the system 10 and its modules 12, 14, 16, and 18 will be apparent to one skilled in the art from the following description and should be considered part of the present disclosure.

Figure 2:
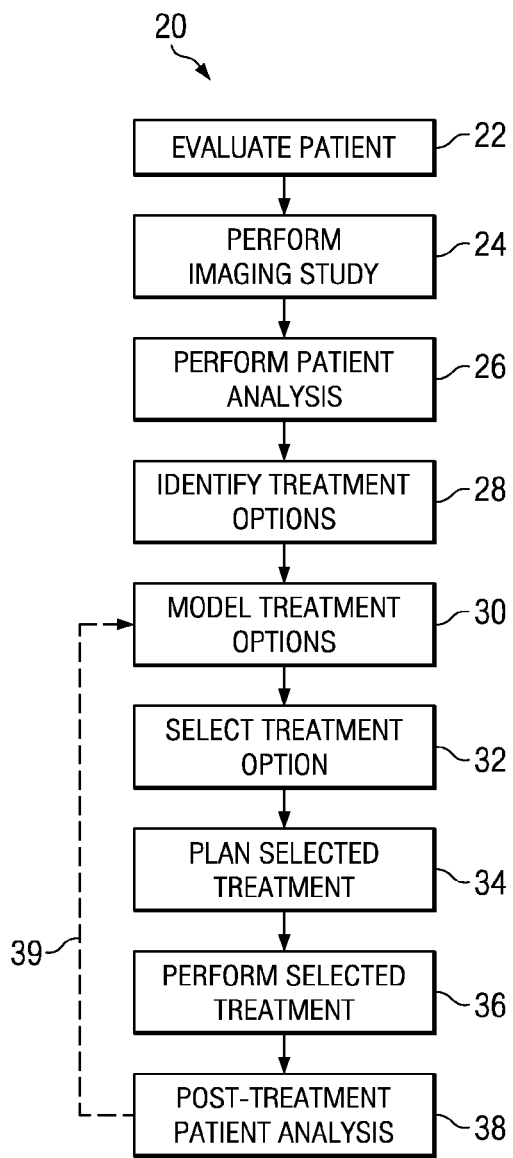
FIG. 2 is a flow chart illustrating a method for diagnosing, treating, and monitoring a patient according to another embodiment of the present disclosure.

Referring to FIG. 2, shown therein is a flow chart illustrating a method 20 for diagnosing, treating, and monitoring a patient according to another aspect of the present disclosure. The method 20 begins at step 22 with evaluation of the patient. The evaluation determines whether the patient should be subjected to the subsequent steps of the method 20. In that regard, the evaluation may vary depending on the types of treatments contemplated by the method 20. For example, in some embodiments the method 20 is based predominantly on surgical treatments. In such embodiments, the evaluation at step 22 focuses on determining whether the patient is a potential candidate for the available surgical treatments. If the evaluation at step 22 indicates that the patient is not a candidate for the available surgical treatments (e.g., due to age or other factors), then the subsequent steps of the method 20 are not performed. On the other hand, if the patient has a condition or symptom that indicates that the patient is definitely a candidate for the available surgical treatments (e.g., spondylolisthesis of grade 2 or more), then the evaluation step may either be truncated or completely skipped, and the method 20 may continue with the subsequent steps.

Figure 3:
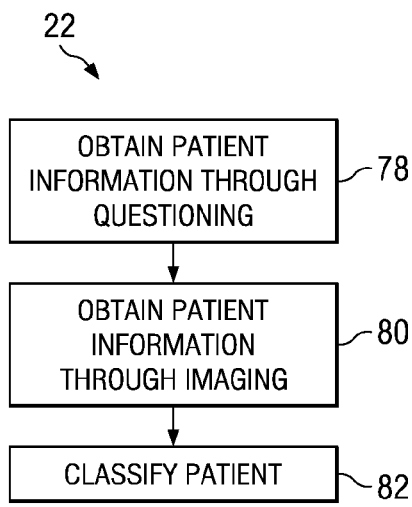
FIG. 3 is a flow chart illustrating the evaluation step of the method of FIG. 2 according to one embodiment of the present disclosure.

Referring more specifically to FIG. 3, shown therein is a flow chart illustrating the evaluation step 22 of the method 20 according to one embodiment of the present disclosure. Generally, the evaluation at step 22 will focus on determining whether the patient is a candidate for the contemplated treatment options. For example, in the context of spinal disorders the method 20 provides treatment options that include spinal implants and related surgical techniques for correcting the spinal disorder. The evaluation step 22 includes obtaining information from the patient. Such information may include standard information on the physical characteristics and condition of the patient. In a particular embodiment, such information includes a series of options for the patient and/or the medical professional to select. Such options are geared toward helping to determine an appropriate treatment, as disclosed herein, and also include goals as to post-operative mobility, activity, or relative deformity; pre-operative condition; prior surgeries or other treatments; or other factors. In the current embodiment, at least some information is obtained by determining the answers to a series of diagnostic questions in step 78. The diagnostic questions include questions such as: How far can the patient walk without pain? Does the patient have pain lying down? Does the patient have pain sitting? Does the patient have pain standing? Does the patient have back pain with leg pain? If yes, is the leg pain localized or radiating? These are exemplary questions and are not to be considered limiting. Numerous other questions may be utilized to evaluate the patient. In that regard, the questions are nested such that subsequent questions depend on the answers to previous questions. Further, some or all of the information provided is weighted so as to emphasize one or more factors as the analysis of potential treatments is performed in some instances. That is, answers to particular questions or information provided are given more importance than other answers or information.

Figure 4:
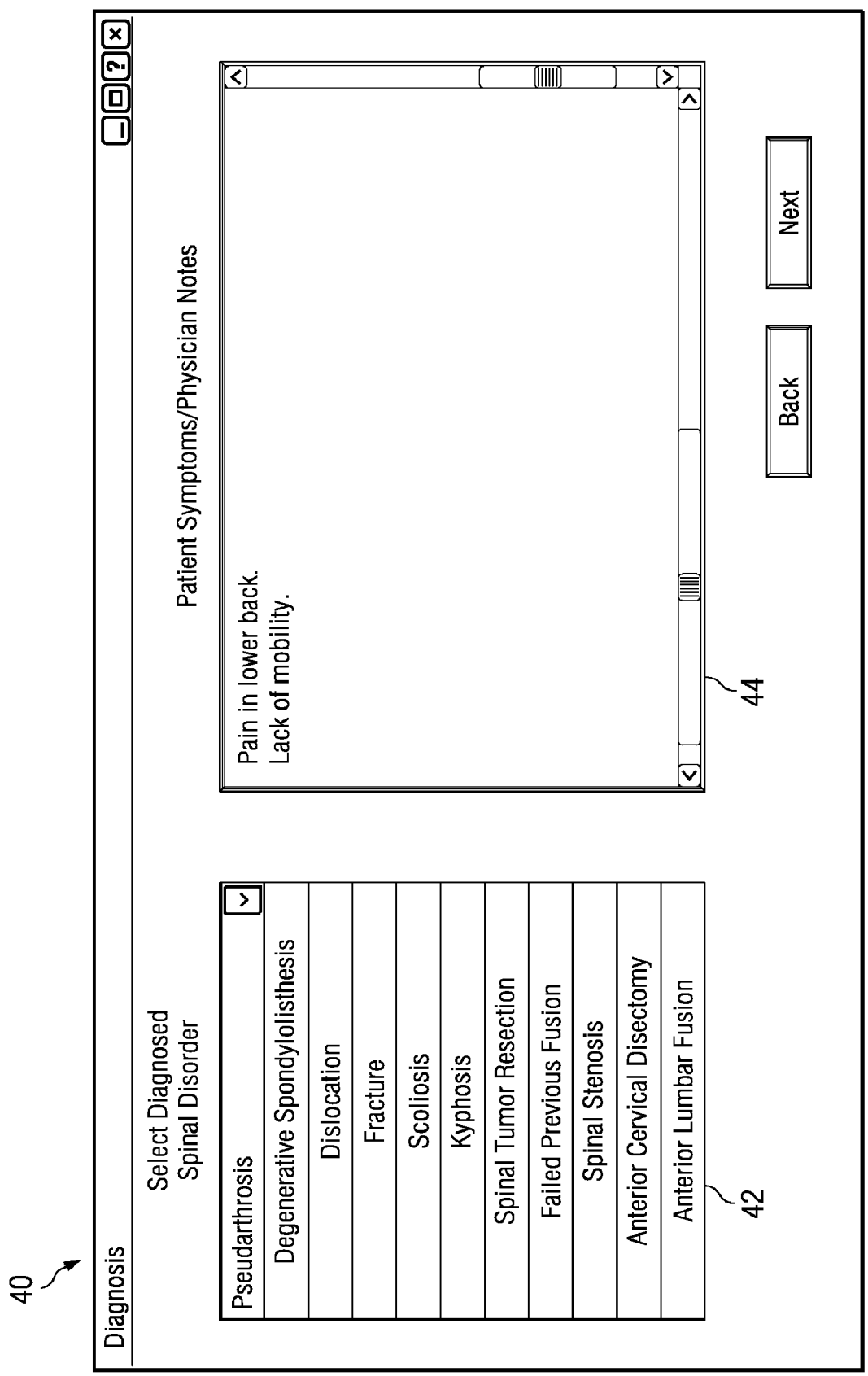
FIG. 4 is an exemplary screen shot of a software interface that is utilized as part of the evaluation step of the method of FIG. 2 according to one embodiment of the present disclosure.

In some embodiments, the questions of step 78 are provided to the patient and/or medical personnel in an interactive computer program. In some embodiments, the diagnosis module 12 of the system 10 (FIG. 1) prompts a user to answer the series of diagnostic questions and/or provide menus for selecting items indicative of the patient's medical condition. Referring to FIG. 4, shown therein is an exemplary screen shot 40 of a software interface that is utilized as part of the evaluation at step 22. A spinal disorder selection menu 42 is provided on the left hand side of the screen shot 40. The menu 42 provides a drop down menu containing a plurality of spinal disorders. The treating physician or other medical personnel selects the spinal disorder(s) afflicting the patient using the menu 42. In other embodiments, the menu 42 includes symptoms (e.g., low back pain, limited flexion, etc.) instead of or in addition to the spinal disorders in some embodiments. A note field 44 is provided on the right hand side of the screen shot 40 allowing additional information regarding the patient to be recorded. It is understood that the screen shot 40 represents a single part of the evaluation step 22 and is not to be considered limiting. In that regard, the evaluation step 22 includes one or more additional pages or screen shots containing additional questions, menus, and/or other inputs related to the patient's condition in some embodiments.

Referring again to FIG. 3, in addition to or in lieu of the diagnostic questions 78 the evaluation at step 22 includes other types of patient analysis. In the current embodiment, imaging techniques are utilized to evaluate the patient at step 80. For example, in some embodiments radiographic images of the patient's anatomy are obtained. The radiographic images are then analyzed to identify any medical conditions afflicting the patient. The medical conditions are then considered as a factor in evaluating the patient. In some embodiments, the patient is put through a series of movements appropriate to determine the patient's motion sequence and/or range of motion for one or more anatomical areas. The patient's motion sequence and/or range of motion in each area is then considered as a factor in evaluating the patient. Additional considerations and/or tests are taken into account during the evaluation of the patient as desired by the treating physician or other medical personnel.

Based on the response to the diagnostic questions 78, imaging data 80, and/or other types of patient analysis, the patient can be grouped into a classification at step 82. In some embodiments, the classification 82 is by type of injury or medical condition. In other embodiments, the classification 82 is based on other patient factors. In some embodiments, the classification 82 is at least partially based on a treating physician or other medical personnel's preferences. It is contemplated that, in some embodiments, each classification is further subdivided into groups based on factors such as the severity of the condition, age, health, and/or other factors. In some embodiments, the classifications and groupings are based on factors identified in clinical studies and/or past patient treatments as being indicators of success for the available treatment options. A general determination can be made regarding whether the patient is a candidate for the available treatment options based on the grouping and classifications. In that regard, it is contemplated that each classification or grouping defines an inclusion group that indicates that the patient is a candidate for an available group of treatment options. If the patient is not a candidate for the available treatment options then the method 20 terminates. If, however, it is determined that the patient is a candidate for the available treatment options, then the method 20 continues with step 24.

Figure 5:
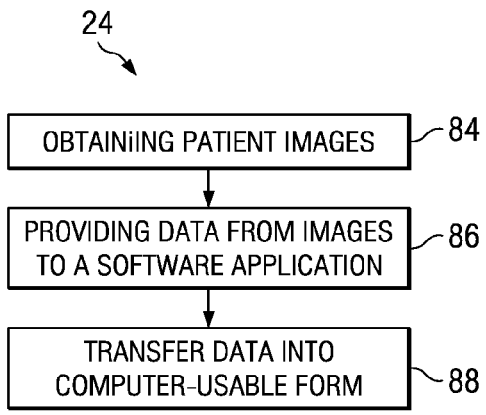
FIG. 5 is a flow chart illustrating the imaging step of the method of FIG. 2 according to one embodiment of the present disclosure.

At step 24, the patient is subjected to an imaging study. Referring more specifically to FIG. 5, shown therein is a flow chart illustrating the imaging step 24 of the method 20 according to one embodiment of the present disclosure. The imaging study includes obtaining patient images through the use of magnetic resonance imaging ("MRI"), computed tomography ("CT"), video fluoroscopy, and/or other imaging techniques at step 84. In some embodiments, the imaging study includes techniques as described in commonly owned U.S. patent application Ser. No. 11/697,426 filed Apr. 6, 2007 and titled "System and Method for Patient Balance and Position Analysis", herein incorporated by reference in its entirety. In general, the imaging study obtains images of the patient's anatomy that are utilized in subsequent steps of the method 20. In particular, the imaging study of step 24 focuses on obtaining images and/or information necessary to model portions of the patient's anatomy.

In some embodiments, the imaging study of step 24 includes tracking the movement of anatomical features of the patient using sensors. In some embodiments the sensors are implantable and are placed in direct contact with and/or within the relevant anatomical feature(s) of the patient. In other embodiments, the sensors remain outside of the patient's body, but are positioned in close proximity to the anatomical feature(s) of interest. For example, in some embodiments the imaging study tracks the position of at least some of a patient's vertebrae. In one embodiment, a sensor is implanted into each vertebra and the location of the vertebra is tracked using the sensor. In another embodiment, a sensor is placed outside the patient's body adjacent the spinous process. The location of the spinous process and, in turn, the vertebra are tracked using the sensor. In some embodiments, the position of the sensors and anatomical features are tracked while the patient is put through a particular motion sequence or protocol. For example, in one embodiment the patient is asked to walk on a treadmill. The position of the sensors and anatomical features are tracked and correlated to the patient's gait cycle. It is understood that these described uses of sensors are merely exemplary and should not be considered limiting. Sensors, implantable or otherwise, may be utilized in numerous other combinations and ways to track the position of anatomical features during the imaging study.

The data from the imaging study is provided to one or more software applications at step 86 in order to derive further information and/or new views of the imaging data. Generally suitable software packages will be capable of one or more of 2-D radiographic measurement and analysis; 3-D modeling, reconstruction, and kinematic simulation; therapy modeling or simulation; and outcome simulation. Examples of such software include the Montreal 3D Radiographic Modeling, Measurement and Surgery Simulation software ("Montreal software"); the TruBalance patient measurement software ("TruBalance software"); and the DRPro radiographic measurement software offered by PhDx eSystems, Inc. of Albuquerque. Other brands or types of software for obtaining, analyzing, or otherwise handling patient data may be used in addition to or instead of one or more of the software applications mentioned above for one or more of the data categories. Also, multiple software applications may be applied to a given set of data. It is understood that data from each study can be assembled together prior to submission to such software, or each study can be treated individually.

In some embodiments, the Montreal software is used to generate a three-dimensional model of the patient's spine, the TruBalance software is used to calculate a global balance for the patient, and the DRPro software is used to measure the images. In some embodiments, an additional step that can be used is to measure the images with software known as Clindexia. At step 88, these software applications transform the raw images into mathematical or other forms that can be manipulated via a computer system and compared to other images and/or other data sets.

Figure 6:
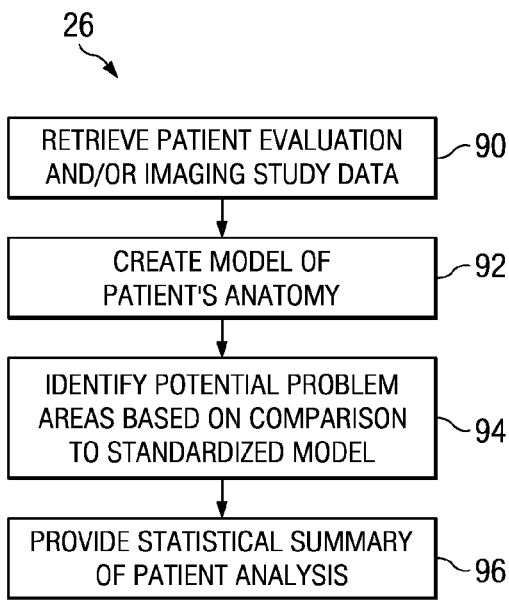
FIG. 6 is a flow chart illustrating the patient analysis step of the method of FIG. 2 according to one embodiment of the present disclosure.

Referring to FIGS. 2 and 6, after the imaging study of step 24, the method 20 continues with step 26 in which a patient analysis is performed. Referring more particularly to FIG. 6, shown therein is a flow chart illustrating the patient analysis step 26 of the method 20 according to one embodiment of the present disclosure. Generally, the patient analysis of step 26 synthesizes the information obtained during steps 22 and 24 to identify the abnormal medical conditions afflicting the patient. In that regard, in the current embodiment step 26 begins with retrieving the patient evaluation and/or imaging study data from steps 22 and 24 at step 90. The patient analysis step 26 continues with step 92 in which a 3-D and/or 2-D animated model of the patient's anatomy is created. Generally, the animated model is based on the data obtained from the imaging study of step 24. In some embodiments, the animated model is used to highlight the problem areas and/or times in the patient's anatomical motion sequence or motion pattern. In that regard, motion sequences and/or motion patterns as the terms are used herein are intended to include a patient's gait, a portion of the patient's gait, a single movement of a single anatomical structure, a series of movements of a single anatomical structure, a single movement of a plurality of anatomical structures, a series of movements of a plurality of anatomical structures, or other aspects of a patient's motion. Generally, any patient motion in whole or part may be referred to as a motion sequence or motion pattern.

The model of the patient's anatomy includes layers of anatomical features that are selectively included or removed. For example, in one embodiment the patient's motion anatomy is grouped into layers according to types of anatomical tissue, such as bones, cartilage, ligaments, tendons, muscles, and/or combinations thereof. The animated model then analyzes motion according to each grouping of anatomical tissue and the interactions therebetween.

In some embodiments, the animated model combines diagnostic tests with the imaging study. For example, in some embodiments the animated model combines muscle monitoring with the imaging study to identify muscle contractions and tensions during a motion sequence or protocol. The results of the muscle monitoring are combined with the other imaging data to provide additional details and/or realism to the animated model. In other embodiments, the animated model utilizes center-of-balance or center-of-gravity data for the patient obtained during the motion sequence or protocol. Muscle monitoring and center-of-balance data are merely examples of the types of additional data that may be combined with the imaging data in forming the animated model. Other types of the patient data may also be utilized. In that regard, in some embodiments the treating physician or medical personnel selects the types of patient data to be used in formulating the animated model.

The animated model includes additional features to allow medical personnel and/or a computer system to analyze the patient. In that regard, in some embodiments the animated model includes a stress grid overlay that indicates potential areas of increased stress or strain on the patient's anatomy, such as increased muscle activity; overstretching of muscles, ligaments, and/or tendons; friction between bones; and/or other areas of stress/strain. In some embodiments the model allows for zooming, panning, or otherwise changing the orientation of the view of the patient's anatomy. A user adjusts the orientation to better observe or isolate a potential problem area. Similarly, the animated model allows a user to pause, rewind, slow down, and/or speed up simulation of a motion sequence to better observe a potential problem. Further, the animated model allows 3-D and/or 2D tracking of specific anatomical features through the motion sequences. At step 94, the animated model highlights potential problem areas automatically based on a comparison to a standardized model associated with the patient and/or the treating physician or medical personnel highlights potential problem areas based on their observations. In some embodiments, the problem areas are identified by a computer system and/or medical personnel by recognizing an abnormal motion pattern(s).

At step 96, a statistical summary of the patient analysis is provided. The summary provides information important to the diagnosis and subsequent treatment of the patient's medical condition. In some embodiments, the statistical summary identifies such things as damaged anatomical features or areas, limited ranges of motion, and/or other data related to the patient's condition. The information provided is at least partially determined by the medical personnel. For example, in some embodiments the medical personnel selects or otherwise accesses the particular information or data sets they deem to be most important in diagnosing and treating the patient. In some embodiments, the statistical summary provides a comparison to other patients with similar medical conditions, medical histories, and/or patient profiles. Further, the selected treatment plans and relative success of those plans for the other patients is provided. The statistical summary also provides a list of possible causes for the medical condition and/or identifies possible relationships between abnormal motion patterns.

Figure 7:
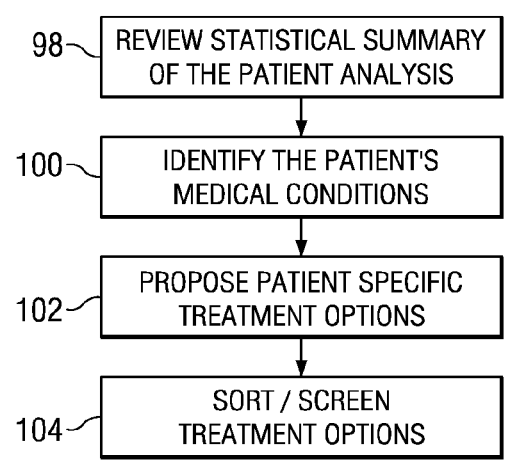
FIG. 7 is a flow chart illustrating the identification step of the method of FIG. 2 according to one embodiment of the present disclosure.

Referring to FIGS. 2, 7, and 8, after the patient analysis of step 26, the method 20 continues with step 28 in which the available treatment options are identified. The treatment options are based upon the patient analysis. Referring more particularly to FIG. 7, shown therein is a flow chart illustrating the identification step 28 of the method 20 according to one embodiment of the present disclosure. In this particular embodiment, the treatment options are determined by looking at the statistical summary of the patient analysis at step 98, identifying the patient's medical condition(s) at step 100, and proposing treatment plans based on the patient's medical condition(s) at step 102. The proposed treatment plans include surgical procedures, non-invasive treatments, and/or medicinal treatments. For sake of example and simplicity, a series of proposed surgical treatment plans will now be discussed in the context of a disc herniation in the lumbar region of the spine as identified by a patient analysis. This is for exemplary purposes only and should not be considered limiting in any way.

Referring more particularly to FIG. 8, shown therein is an exemplary screen shot 46 of a software interface that is utilized as part of identifying the available treatment options at step 28. In the current embodiment, a spinal disorder menu 48 is provided on the left hand side of the screen shot 46. The spinal disorder menu 48 currently indicates that the patient suffers from a lumbar disc herniation. In other instances, the patient may suffer from other spinal disorders and/or a plurality of spinal disorders. A treatment menu 50 is provided on the right hand side of the screen shot 46 and includes a plurality of treatment plans. The treating physician or other medical personnel selects one or more of the treatment plans from among the plurality of treatment plans using the treatment menu 50. In the current embodiment, the treatment menu 50 provides a plurality of surgical treatment options for correcting a lumbar disc herniation. In some embodiments, the treatment menu 50 includes an option allowing a surgeon or other physician to input a treatment plan based on her own experience that is not included in the plurality of treatment options.

Referring again to FIGS. 2, 7, and 8, in some embodiments the treatment options of step 28 are sorted and/or screened based on physician preference at step 104. For example, if a physician prefers surgical procedures that utilize a posterior approach, then the available treatment options are limited to those implants and surgical procedures that are implanted through a posterior approach. As another example, the treatment options are sorted based on the success of the treatment plan for previous patients having a similar profile to the current patient. Similarly, in some embodiments the treatment options are sorted based on the previous procedures performed by the treating physician/surgeon and the relative success of those procedures. In other embodiments, the patient suffers from medical conditions unrelated to the spine that is presented in a similar manner—indicating the medical condition and proposing a plurality of treatment options.

Figure 9:
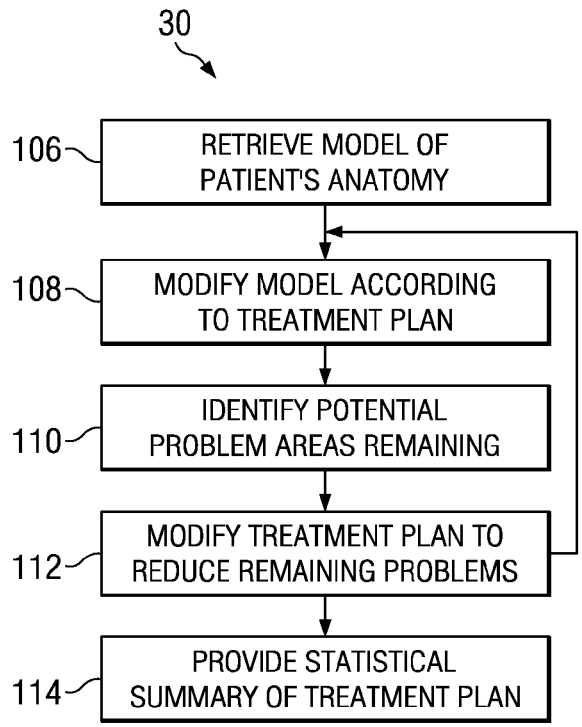
FIG. 9 is a flow chart illustrating the modeling step of the method of FIG. 2 according to one embodiment of the present disclosure.
Figure 10:
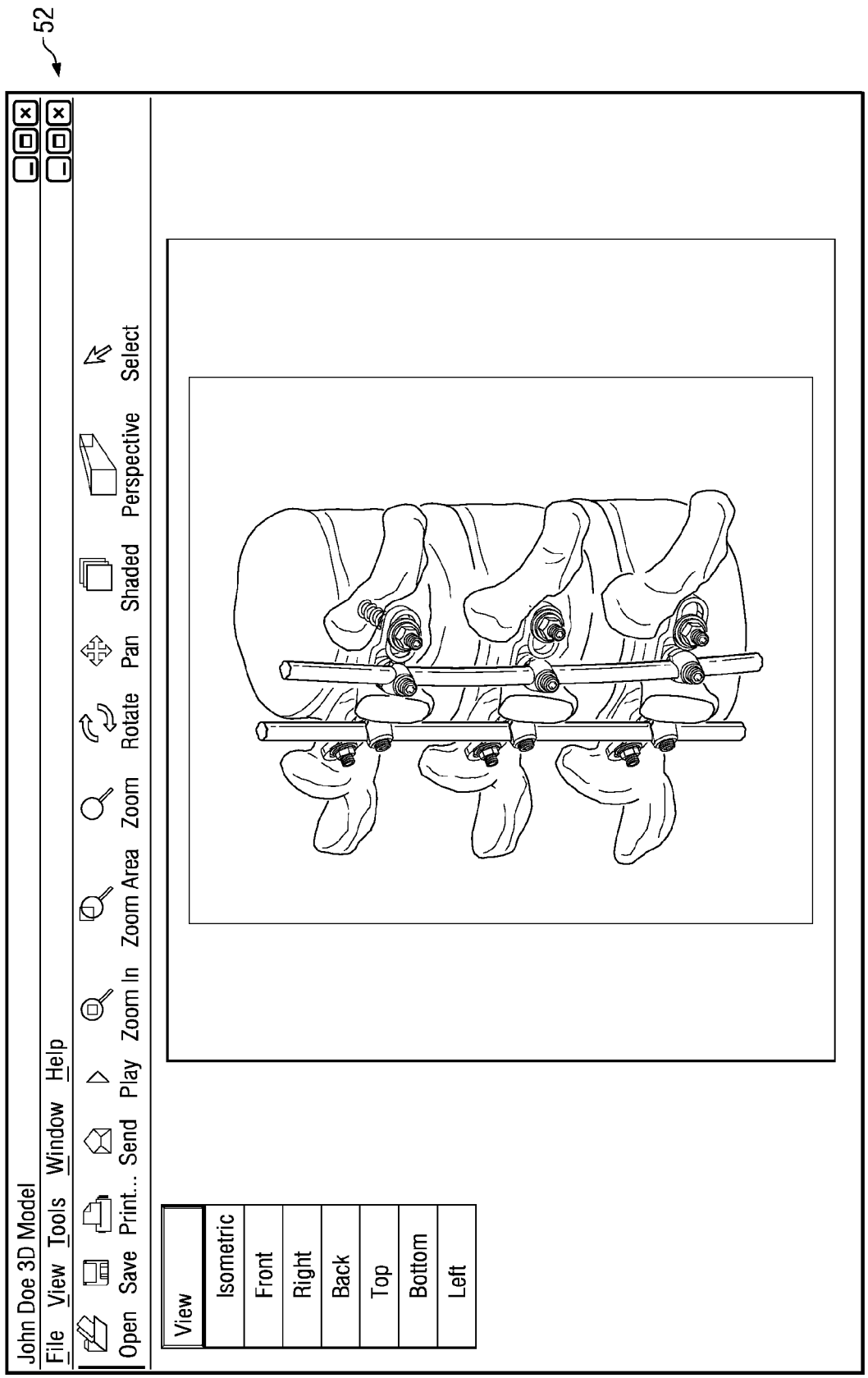
FIG. 10 is an exemplary screen shot of a software interface showing a representative figure of the modeling step of the method of FIG. 2 according to one embodiment of the present disclosure.

Referring to FIGS. 2, 9, and 10, after identifying one or more of the available treatment plans at step 28, the method 20 continues at step 30 with modeling of the available treatment options. Referring more specifically to FIG. 9, shown therein is a flow chart illustrating the modeling step 30 of the method 20 according to one embodiment of the present disclosure. Modeling of the treatment options builds upon the animated model of the patient analysis of step 26. In that regard, the modeling step 30 begins with retrieving the model of the patient's anatomy at step 106. Next, the modeling step 30 continues by modifying the 3-D and/or 2-D animated model of the patient's anatomy according to the treatment plan at step 108. For example, in some embodiments the animated model is modified by replacing a damaged portion of the patient's anatomy with an implant. A model can then be created utilizing the characteristics of the implant in place of the damaged portion of the patient's anatomy as indicated by step 108. Referring to FIG. 10, shown therein is a screen shot 52 of a software interface showing a representative figure of a modeling according the present embodiment.

In some embodiments, the modeling is used to identify potential problem areas and/or times in the patient's anatomical motion sequence that remain after implantation of the implant at step 110. In that regard, as previously described the model includes layers of anatomical features that may be selectively included or removed, such as bones, cartilage, ligaments, tendons, muscles, and/or combinations thereof. The model analyzes the motion sequence at each level of anatomical tissue with the implant in place and then the model the resultant motion sequence including all of the levels. In that regard, in some embodiments the model takes into account the surgical procedure or approach utilized in inserting the implant. For example, if muscles, tendons, cartilage, and/or other supporting tissues will be cut or resected during the surgical procedure, then the model takes this into account in modeling the resultant motion sequences. The model highlights potential problem areas automatically based on a comparison to a standardized model associated with the patient and/or the treating physician or medical personnel may highlight potential problem areas based on their observations of the resultant motion sequence. In some embodiments, the problem areas are identified by a computer system and/or medical personnel by recognizing or tracking an abnormal motion pattern(s).

By identifying potential problem areas and/or times in the patient's anatomical motion sequence and taking into account the tissues that will be compromised during the surgical procedure, the modeling provides a realistic estimation of the resultant outcome of the treatment plan. In that regard, the treating physician optimizes each treatment plan by modifying such factors as the size, placement, orientation, and material properties of a particular implant and/or modifying the surgical procedure to adjust the tissues that will be compromised at step 112. Further, the treatment plan is modified according to weighted factors concerning the patient's characteristics and/or the desired outcome at step 112. After the treatment plan is modified the modeling step 30 may return to step 108 and update the model according to the modified treatment plan. This process may be iterated until the physician is satisfied with the parameters of the treatment plan. For each of the selected treatment plans and/or implants, the treating physician saves one or more optimized plans in a database or other accessible memory location. A statistical summary of the optimized treatment plan is provided for each selected treatment plan at step 114.

Additional features as previously mentioned may be utilized to model the treatment plans. In some embodiments the model includes a stress grid overlay that indicates potential areas of increased stress or strain on the patient's anatomy, such increased muscle activity; overstretching of muscles, ligaments, and/or tendons; friction between bones; and/or other areas of stress/strain caused by the implant and/or treatment plan. In some embodiments the model allows for zooming, panning, or otherwise changing the orientation of the view of the patient's anatomy with the implant inserted. A user adjusts the orientation to better observe placement and/or functioning of the implant. Similarly, the model allows a user to pause, rewind, slow down, and/or speed up simulation of a motion sequence to better observe the patient's motion with the implant. Further, the model allows 3-D and/or 2D tracking of specific anatomical features through the motion sequences.

In some embodiments, the method 20 does not include step 30. In other embodiments, the method 20 includes the modeling and optimization of step 30 with respect to only some of the selected treatment plans. In that regard, some treatment plans do not lend themselves to modeling and, therefore, may not be modeled even when other selected treatment plans are modeled. Further, the example described above focused on treatment plans including insertion of implant and the corresponding surgical procedures. It is understood that similar modeling and optimization approaches are utilized to model non-surgical procedures and/or other types of treatment plans in some embodiments.

Figure 11:
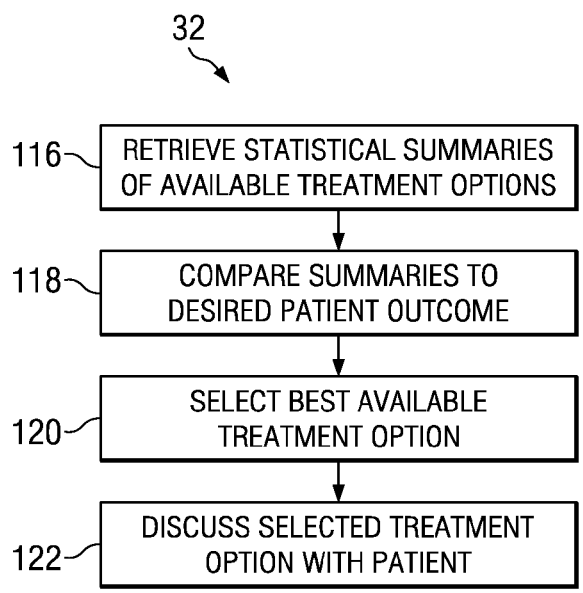
FIG. 11 is a flow chart illustrating the selection step of the method of FIG. 2 according to one embodiment of the present disclosure.
Figure 12:
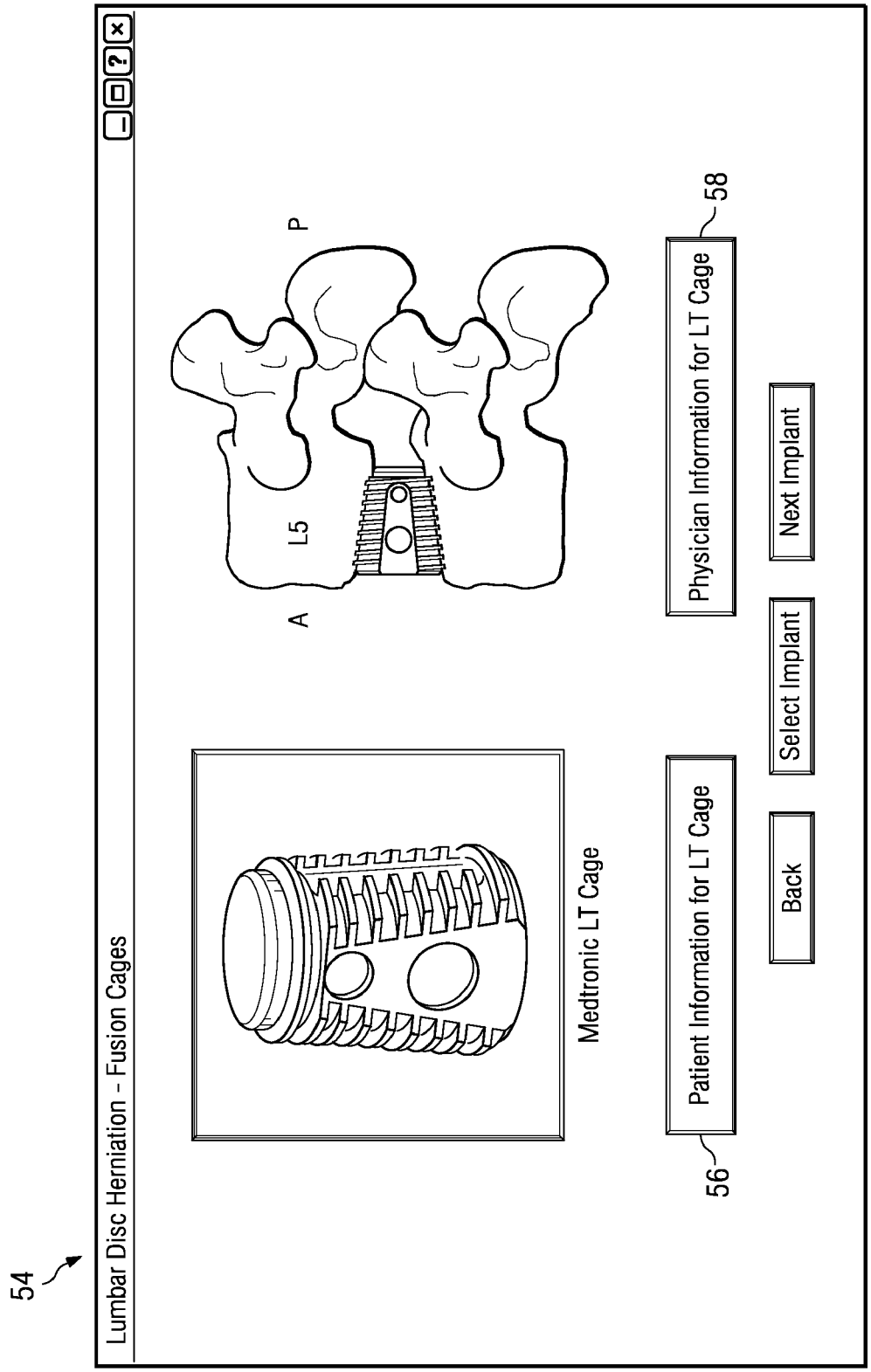
FIG. 12 is an exemplary screen shot of a software interface that is utilized as part of the selection step of the method of FIG. 2 according to one embodiment of the present disclosure.

Referring to FIGS. 2, 11, and 12, after optimizing each of the selected treatment plans at step 30, the method 20 continues at step 32 where a treatment option is selected. Referring more particularly to FIG. 11, shown therein is a flow chart illustrating the treatment plan selection step 32 of the method 20 according to one embodiment of the present disclosure. Generally, a physician and/or a computer system compares the modeled results and/or statistical summaries for each of the optimized plans and selects the plan best suited for correcting the patient's medical condition. The selection step 32 begins with retrieving the statistical summaries of the available treatment options at step 116. The plan best suited for the patient is based on such factors as the patient's profile, the desired results, the physician's preferences, and/or the patient's preferences. It is contemplated that in some instances a computer system ranks the treatment options based on the results of previous patients having similar profiles to the current patient. In that regard, the computer system includes the confidence level for particular outcomes for each treatment option in some embodiments. Accordingly, at step 118 the statistical summaries of the available treatment options are compared to the desired patient outcomes. With the clinical outcomes modeled and the results displayed with respective confidence intervals or levels for each outcome related to the particular treatment options, medical personnel can make the appropriate decisions for treating the patient with by balancing the trade-off of parameters that important to the medical personnel and the patient's outcome. The medical personnel's decision can be made from actual patient data relative to a similar condition that represents their particular patient's problem. In the end, taking all of the various considerations into account the best available treatment option for the patient is selected at step 120.

In addition to selecting a treatment option, step 32 also includes discussing the selected treatment option with the patient at step 122. In that regard, the results of the analyses and modeling are shown and/or explained to the patient to support the decision to go with a particular treatment. Further, in the case of a treatment plan that includes inserting an implant or otherwise employing a medical device, the patient may be given access to additional product information regarding the medical device. In some embodiments, discussing the treatment option with the patient is accomplished over the internet, an intranet, computer network, telecommunications network, or other type of remote connection. In that regard, the link between the patient and the medical professional may be a secure link or secured communication channel so as to protect the patient's confidentiality. In some instances, the treatment options are provided over a secure website. The patient is provided access to the secure website via a username and password associated with the patient. In addition to providing the patient information regarding the selected treatment option(s), the patient interface also provides the patient with the ability to ask questions. In some embodiments, the interface includes a query box that is filled out and submitted by the patient, which a medical professional replies to. In other embodiments, the interface is in the form of a chat or instant messaging session. The patient may ask questions over the chat session and the medical personnel can provide answers to these questions immediately or seek answers to the questions and reply to the patient at a later time. In yet other embodiments, the patient interface may be combined with video-conferencing or telephonic-conferencing to provide additional information and opportunities for questions to the patient.

Referring to FIG. 12, shown therein is an exemplary screen shot 54 of a software interface that may be utilized as part of step 32. In the current embodiment, a link 56 to a product information page regarding an implant designed for the patient is provided on the left hand side of the screen shot 54. In that regard, the product information page designed for the patient includes generalized information regarding the type of implant, the typical uses of the implant, specifications of the implant, success stories related to the implant, and/or other information related to the implant that would be desirable to share with a patient. A link 58 to a product information page regarding an implant designed for the physician or medical personnel is provided on the right hand side of the screen shot 54. The product information page designed for the physician includes information related to the appropriate surgical approaches available for inserting the implant, details of the preferred surgical procedure(s), specifications of the implant, available variations/models of the implant (e.g., sizes, materials, etc.), and/or other information related to the implant that would be desirable to share with the physician.

Figure 13:
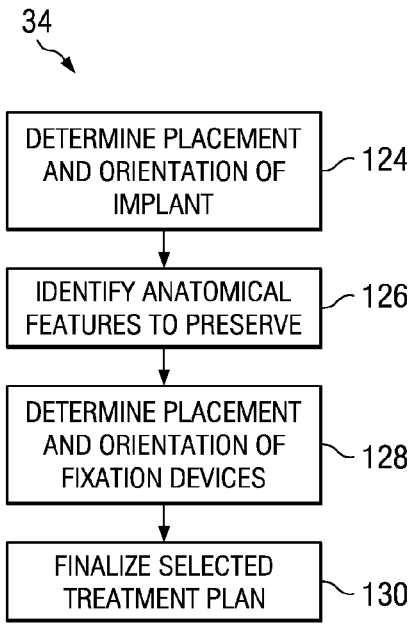
FIG. 13 is a flow chart illustrating the planning step of the method of FIG. 2 according to one embodiment of the present disclosure.

Referring to FIGS. 2 and 13, after selection of the treatment option at step 32, the method 20 continues with step 34 in which the execution of the selected treatment option is planned. In this regard, a majority and/or all of step 34 is included in the optimization of the treatment plans in step 30. However, not all of the details of executing the treatment plan are necessarily addressed in step 30. Further and as noted previously, in some embodiments step 30 is not included and, therefore, planning the execution of the treatment option is completed in step 34. In some embodiments, planning the treatment option comprises planning the surgical procedure utilized to insert the implant. For example, referring more particularly to FIG. 13, shown therein is a flow chart illustrating the planning step 34 of the method 20 according to one embodiment of the present disclosure where the selected treatment option is a surgical procedure. The planning step 34 begins with determining the desired placement and orientation of the implant at step 124. The planning step 34 continues by identifying any anatomical features that need to be preserved through the surgical procedure at step 126. Further, the desired fixation positions and orientations for any fixation devices are established and marked on a model at step 128. These fixation positions and orientations are saved for future reference during the actual surgical procedure. With respect to the planned placement and orientation of the implant and/or fixation devices, an error field is established that identifies the expected range of accuracy within which the implant and/or fixation devices should be implanted. Based on this expected range of accuracy, a corresponding expected range of performances is established for the treatment plan. Image guided surgery techniques are utilized in some embodiments to ensure that the treatment plan is executed according to the desired positions and orientations. Further, the position of the patient during each step of the treatment plan is determined in some instances. For some treatment plans the patient is moved between different positions for various steps of the treatment plan. Accordingly, in some embodiments the selected treatment option is planned in accordance with use of a dynamic surgical table as described in U.S. Pat. No. 7,234,180, filed Dec. 10, 2004 and titled "Dynamic Surgical Table System," hereby incorporated by reference in its entirety. Taking these various factors into consideration planning the execution of the selected treatment option is finalized at step 130.

Figure 14:
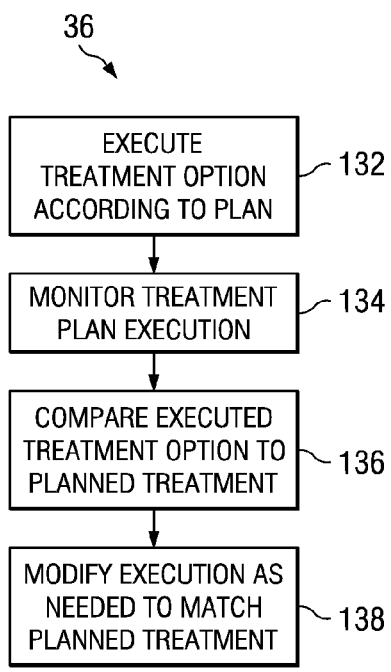
FIG. 14 is a flow chart illustrating the performance step of the method of FIG. 2 according to one embodiment of the present disclosure.

Referring to FIGS. 2 and 14, after planning the execution of the treatment plan at step 34, the method 20 continues with step 36 in which the treatment plan is executed. Referring more particularly to FIG. 14, shown therein is a flow chart illustrating the performance step 36 of the method 20 according to one embodiment of the present disclosure. At step 132, the treatment plan is executed in accordance with the planning that has occurred in the previous steps. In that regard, in the context of a surgical procedure the procedure is monitored intra-operatively at step 134. The actual surgical procedure, as monitored, is compared in real-time, or approximately real-time, to the planned treatment at step 136. Thus, the actual placement of the implant and fixation devices is compared to the intended placement and/or associated error fields. In this manner, an analysis of the placement of the surgical components is performed before the patient leaves the operating room. At step 138, the actual surgical procedure is modified as needed to ensure that it coincides with the error fields of the planned treatment. Thus, any initial adjustments that need to be made can be accomplished without the need for a revision surgery or a return to the operating room. In some embodiments, the position of the implant and/or fixation devices is established using implantable sensors located within the implant, fixation devices, and/or insertion instruments. For example, in some instances the implant and/or fixation devices include sensors such as those described in U.S. patent application Ser. No. 10/985,108 filed Nov. 10, 2004; U.S. patent application Ser. No. 11/118,170 filed Apr. 29, 2005; U.S. patent application Ser. No. 11/344,667 filed Feb. 1, 2006; U.S. patent application Ser. No. 11/344,999 filed Feb. 1, 2006; U.S. patent application Ser. No. 11/356,687 filed Feb. 17, 2006; U.S. patent application Ser. No. 11/344,459 filed Jan. 31, 2006; U.S. patent application Ser. No. 11/344,668 filed Feb. 1, 2006; each of which is hereby incorporated by reference in its entirety. In some embodiments, the surgery and/or other treatment plans are performed using computer-guided surgical techniques that are based on the selected treatment option.

Figure 15:
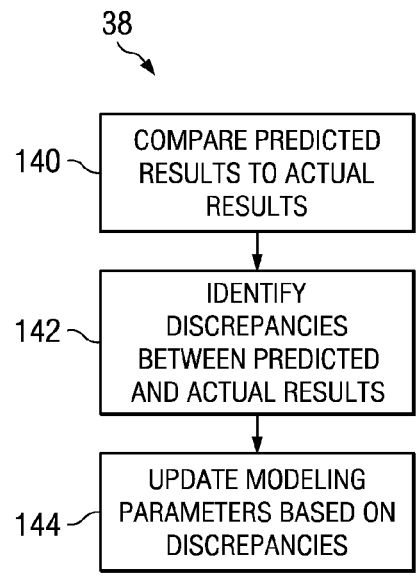
FIG. 15 is a flow chart illustrating the post-treatment analysis step of the method of FIG. 2 according to one embodiment of the present disclosure.

Referring to FIGS. 2 and 15, after executing the treatment plan or a part thereof at step 36, the method continues with step 38 in which a post-treatment analysis is performed. In some embodiments, the post-treatment analysis is substantially similar to steps 22, 24, and/or 26 described above. Referring more specifically to FIG. 15, shown therein is a flow chart illustrating the post-treatment analysis step 38 of the method 20 according to one embodiment of the present disclosure. In that regard, the post-treatment analysis step 38 includes comparing the predicted results of the modeling of step 30 to the actual results of the treatment at step 140. Any discrepancies between the model and the actual results are identified at step 142. At step 144, the discrepancies are utilized to improve the correlation between the model and actual results. In that regard, the parameters utilized for creating the models are updated and modified based on the identified discrepancies. Ideally, the predicted results provided by the model are substantially similar to the actual results of the treatment plan. In some embodiments, the post-treatment analysis is performed at set intervals after the surgical procedure. In one particular embodiment, the patient goes through post-treatment analysis at least at 2 weeks, 6 weeks, and 3 months after the surgical procedure. In some embodiments, sensors located within the implant and/or fixation devices are utilized in the post-treatment analysis to obtain data related to the patient's motion sequence(s).

By monitoring the resultant data from each patient for each treatment plan, a statistical correlation between medical conditions and treatment options is established. This statistical correlation is utilized in selecting the treatment plans for subsequent patients. For example, in some instances the method includes step 39 that comprises a feedback loop to an earlier step in the method, such as step 30 for example. In that regard, modeling of the treatment options at step 30 can be updated to correspond with the outcomes as observed in the post-treatment analysis of step 38. In that regard, in some instances the current patient's resultant data is routed and stored as a part of a study and/or other collection of data into a database for future access by the system 10. Generally, the data will need to be de-identified from the particular patient, so as to preserve confidentiality and impartiality of the data and to comply with applicable laws. For example, the patient's name, social security number, address, and/or other sensitive information are removed from the data, while the patient's physical characteristics, selected treatment plan, and outcome are maintained. In some embodiments, the data is entered into the databases by a medical professional as part of the post-treatment analysis of step 38 of the method 20. This data related to current patient's outcome is the feedback that provides confirmation of prior information and/or new information from which the medical professionals can modify the treatment plans and/or medical device manufacturers can modify the implants or devices.

Further, in some instances the database includes information regarding whether the patient's treatment plan was an on-label or off-label use of a medical product. In that regard, in some embodiments the database and/or software interface includes a field that allows the treating physician or medical personnel to describe the particular use of the medical product. Accordingly, a later physician can evaluate the possibility of such a use for his or her patient. The database or system can highlight off-label uses so that treatment plans for later patients are not adversely affected by previous off-label uses that skew the data results. In some embodiments, the database includes information regarding reimbursement procedures. In that regard, the database includes the various requirements for obtaining reimbursement from various insurance companies in some embodiments. Further, the database keeps track of the success of previous reimbursement requests based on the associated patient data in some instances. Accordingly, a treating physician is able to evaluate the likelihood of being reimbursed from a particular insurance company for a selected treatment plan.

Referring again to FIGS. 1 and 2, the system 10 and, in particular, the modules 12, 14, 16, and 18 may provide a platform for executing some or all of the steps of the method 20 described above. Accordingly, aspects of the system 10 will now be described in connection with the method 20. The diagnosis module 12 is adapted to execute some or all portions of steps 22, 24, and 38. In that regard, the diagnosis module 12 prompts a user to answer a series of diagnostic questions and/or provide one or more menus for selecting items indicative of the patient's medical condition. The exemplary screen shot 40 of the software interface shown in FIG. 3 is utilized in some embodiments. The diagnosis module 12 is also configured to process patient diagnosis data in addition to, or in lieu of, the diagnostic questions. In some embodiments, imaging techniques are utilized to evaluate the patient and the diagnosis module may be adapted to receive, store, and/or process the images. For example, in some embodiments radiographic images of the patient's anatomy are obtained, transferred to the diagnosis module 12, and stored in a database accessible by the diagnosis module 12. The radiographic images are then analyzed by the diagnosis module 12 and/or the physician to identify any medical conditions afflicting the patient. In some embodiments, the patient is put through a series of movements appropriate to determine the patient's motion sequence and/or range of motion for one or more anatomical areas. The patient's motion sequence and/or range of motion in each area are captured, transferred to the diagnosis module 12, and utilized by the diagnosis module in evaluating the patient. The diagnosis module 12 is configured to receive other data sets or information and take such data into account during the evaluation of the patient in some embodiments.

For example, the diagnosis module 12 is adapted to receive patient data related to an imaging study in some embodiments. The imaging study includes patient images obtained through the use of magnetic resonance imaging ("MRI"), computed tomography ("CT"), video fluoroscopy, and/or other imaging techniques. In some embodiments, the imaging study includes techniques as described in commonly owned U.S. patent application Ser. No. 11/697,426 filed Apr. 6, 2007 and titled "System and Method for Patient Balance and Position Analysis", herein incorporated by reference in its entirety. In some embodiments, the imaging study of step 24 includes tracking the movement of anatomical features of the patient using sensors. The imaging data is stored in a database accessible by the diagnosis module 12.

Based on the response to the diagnostic questions and/or other types of patient analysis data obtained, the diagnosis module 12 groups the patient into a particular classification of patient. In some embodiments, the classification is by type of injury or medical condition. In other embodiments, the classification is based on other patient factors such as height, weight, age, or otherwise. In some embodiments, the classification is at least partially based on a treating physician or other medical personnel's preferences that are selected or otherwise defined within the diagnosis module 12. It is contemplated that in some instances each classification is further subdivided into groups based on factors such as the severity of the condition, age, health, and/or other factors. In some embodiments, the classifications and groupings are based on factors identified in clinical studies and/or past patient treatments as being indicators of success for the available treatment options. In that regard, the diagnosis module 12 is in communication with a database containing information regarding past clinical studies and/or patient treatments that may be utilized in diagnosing the current patient.

The modeling module 14 is adapted to execute some or all portions of steps 26, 30, 32, 34, and 36 of the method 20. In that regard, the modeling module 14 synthesizes the information obtained by the diagnosis module 12 during steps 22 and 24 to identify the abnormal medical conditions afflicting the patient. In that regard, the modeling module 14 creates a 3-D and/or 2-D animated model of the patient's anatomy. The animated model is based substantially on the imaging data obtained by the diagnosis module 12. In some embodiments, the modeling module 14 is used to highlight the problem areas and/or times in the patient's anatomical motion sequence. In that regard, the modeling module 14 allows selection of particular layers of anatomical features. For example, in one embodiment the patient's motion anatomy is grouped into layers according to types of anatomical tissue, such as bones, cartilage, ligaments, tendons, muscles, and/or combinations thereof. The modeling module 14 provides a user interface allowing medical personnel to select the layers of anatomical tissue to be considered in modeling the patient's motion. The modeling module 14 analyzes the motion according to the selected grouping of anatomical tissue and the interactions therebetween.

In some embodiments, the modeling module 14 is configured to combine diagnostic tests with the imaging study in creating the animated model. For example, in some embodiments the modeling module 14 combines muscle monitoring with the imaging study to identify muscle contractions and tensions during a particular motion sequence or protocol. In other embodiments, the modeling module 14 utilizes center-of-balance and/or center-of-gravity data for the patient obtained by the diagnosis module 12. In some embodiments, devices and methods as described in commonly owned U.S. Pat. No. 7,361,150 filed Jun. 25, 2004 and titled "Method and Device for Evaluating the Balance Forces of the Skeleton," herein incorporated by reference in its entirety, are utilized. Muscle monitoring and center-of-balance data are merely examples of the types of additional data that are used with the imaging data by the modeling module 14 in forming the animated model. In other embodiments, the modeling module 14 is adapted to utilize other types of the patient data as well.

The modeling module 14 includes additional features to allow medical personnel and/or a computer system to analyze the patient. In that regard, in some embodiments the modeling module 14 creates a stress grid overlay that highlights potential areas of increased stress or strain on the patient's anatomy, such increased muscle activity; overstretching of muscles, ligaments, and/or tendons; friction between bones; and/or other areas of stress/strain. In some embodiments, the module 14 provides a user interface that allows for zooming, panning, or otherwise changing the orientation of the view of the patient's anatomy. A user adjusts the orientation to better observe or isolate a potential problem area. Similarly, in some embodiments the module 14 provides a user interface that allows a user to pause, rewind, slow down, and/or speed up simulation of a motion sequence to better observe a potential problem. Further, the modeling module 14 allows 3-D and/or 2D tracking of specific anatomical features through the motion sequences in some instances. In some embodiments, the modeling module 14 highlights potential problem areas for the patient based on a comparison to a standardized model associated with the patient. In that regard, the modeling module 14 is in communication with a database containing a plurality of standardized models for such use. In some embodiments, the problem areas are identified by the modeling module 14 by identifying an abnormal motion pattern.

The modeling module 14 is also utilized in modeling the selected treatment options. Modeling of the treatment options builds upon the animated model of the patient used during the patient diagnosis and analysis. Thus, in many aspects the module 14 utilizes the same features described above in modeling the treatment options. However, in modeling the treatment options the modeling module 14 modifies the model by replacing a damaged portion of the patient's anatomy with an implant. The module 14 then utilizes the characteristics of the implant in modeling the patient's anatomical motion sequences. Further, in some embodiments the modeling module 14 further modifies the model by taking into consideration the surgical approach that will be used and any corresponding anatomy that will be sacrificed by the surgical approach. In this manner, the modeling module 14 provides an estimation of the outcome of the treatment plan taking into account these additional factors. In that regard, the treating physician may optimize each treatment plan by utilizing the modeling module 14 to modify such factors as the size, placement, orientation, and material properties of a particular implant and/or modifying the surgical procedure to adjust the tissues that will be compromised.

The modeling module 14 is also utilized in planning the selected treatment option in some instances. In some embodiments, the planning includes determining an optimized surgical procedure for inserting the implant. In that regard, the modeling module 14 takes into account such factors as the desired placement and orientation of the implant and/or the need to preserve certain anatomical features in determining the appropriate surgical procedure. Further, in some embodiments desired fixation positions and orientations for the fixation devices are established and marked on the model created by the modeling module 14. These fixation positions are saved for future reference during the actual surgical procedure. With respect to the planned placement and orientation of the implant and/or fixation devices, the modeling module 14 establishes an error field that identifies the expected range of accuracy in which the implant and/or fixation devices will be implanted. Based on this expected range of accuracy, a corresponding range of performances are established for the treatment plan and modeled by the modeling module 14. For each of the selected treatment plans and/or implants, the treating physician may save one or more optimized plans in a database or other memory accessible by the modeling module 14.

Subsequently, the optimized plans of the modeling module 14 are utilized in the execution of the treatment plans. For example, the optimized plans of the modeling module 14 are used during a surgical procedure to guide the physician to the appropriate placement of an implant and/or fixation device. The surgical procedure is monitored intra-operatively and compared in real-time, or approximately thereto, to the planned treatment. Thus, the actual placement of the implant and fixation devices is compared to the intended placement and/or the associated error fields. In some embodiments, the position of the implant and/or fixation devices is established using implantable sensors located within the implant, fixation devices, and/or insertion instruments. In some embodiments, the surgery or other treatment plan is performed using computer-guided surgical techniques that are based on the optimized treatment option created with the modeling module 14.

The treatment module 16 is adapted to execute some or all portions of steps 28, 30, 32, 34, and 36 of the method 20. In that regard, the treatment module 16 identifies the available treatment options for a particular patient. The treatment module 16 will identify the available treatment options based upon the patient analysis performed by the diagnosis module 12 and the modeling module 14. Thus, in some embodiments the treatment options may be determined by looking at the results of the patient analysis, identifying the patient's medical condition(s), and proposing treatment plans based on the patient's medical condition(s). The treatment module 16 may propose treatment plans that include surgical procedures, non-invasive treatments, and/or medicinal treatments. In some embodiments, the treatment module 16 facilitates sorting and/or screening of the treatment options. In some embodiments, the treatment options are sorted and/or screened based on physician preference. For example, if a physician prefers surgical procedures that utilize a posterior approach, then the available treatment options are limited to those implants and surgical procedures that may be implanted using a posterior approach. The treatment module 16 also provides a user interface for selecting the physician's preferences. As another example, in some instances the treatment options are sorted based on the success of the treatment plan for previous patients having a similar profile to the current patient. Similarly, the treatment options are sorted based on the previous procedures performed by the treating physician/surgeon and the relative success of those procedures in some instances. In each of these examples, the treatment module 16 is in communication with a database containing the relevant information for sorting and/or screening the treatment options. For example, in at least one embodiment the physician's preferences are stored in a database that is accessible by the treatment module 16 when the physician logs into the system using a username and password. Similarly, a database maintaining the results of the previous treatment options and the patient details for these treatment options is accessible by the treatment module 16 in some embodiments.

The post-treatment feedback module 18 is adapted to execute some or all portions of step 38 of the method 20. In some aspects the post-treatment feedback module 18 is substantially similar to the diagnosis module 12. In that regard, in some embodiments the system 10 does not include a separate post-feedback module 18. Rather, the diagnosis module 12 and the post-feedback module comprises a single module. The post-treatment feedback module 18 is utilized to compare the predicted results of the modeling module 14 to the actual results of the treatment plan. Any discrepancies between the model and the actual results are identified by the post-treatment feedback module 18 and utilized to improve the correlation between the model and actual results. Ideally, the predicted results provided by the model are substantially similar to the actual results of the treatment plan. In some embodiments, sensors located within the implant and/or fixation devices are utilized by the post-treatment feedback module 18 to obtain data related to the patient's motion sequence(s). By monitoring the resultant data from each patient for each treatment plan, a statistical correlation between medical conditions and treatment options is established. This statistical correlation and/or underlying data are stored in a database accessible by the diagnosis module 12, modeling module 14, and/or the treatment module 16 and are utilized in conjunction with subsequent patients for diagnosing, modeling, and/or selecting appropriate treatment plans.

It is understood that while each of the modules 12, 14, 16, and 18 have been described as having particular functions no limitations are intended thereby. In that regard, the functions described above with respect to a particular module may be performed by other modules and/or multiple modules. In some embodiments the functions of two or more of the modules may be performed by a single module. In other embodiments, the function(s) of a single module may be distributed across multiple modules. It is understood that the term module may include software, hardware, and/or combinations of hardware and software.

Figure 16:
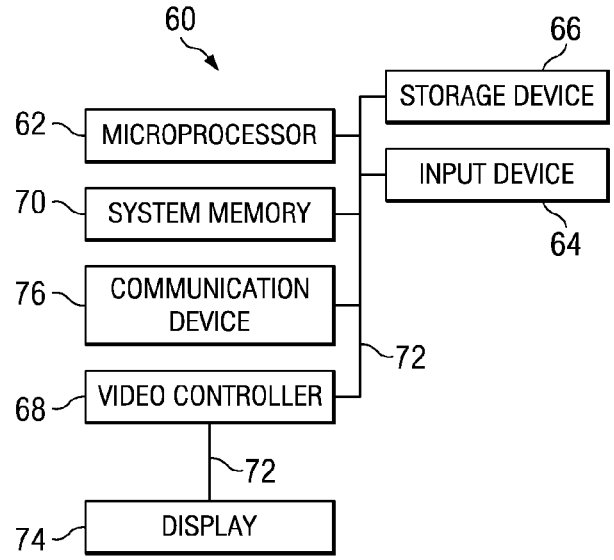
FIG. 16 is a diagrammatic schematic view of a node for implementing the systems and methods of the present disclosure according to one embodiment of the present disclosure.

Referring now to FIG. 16, shown therein is an illustrative node 60 for implementing embodiments of the systems and methods described above. Node 60 includes a microprocessor 62, an input device 64, a storage device 66, a video controller 68, a system memory 70, and a display 74, and a communication device 76 all interconnected by one or more buses 72. The storage device 66 could be a floppy drive, hard drive, CD-ROM, optical drive, or any other form of storage device. In addition, the storage device 66 may be capable of receiving a floppy disk, CD-ROM, DVD-ROM, or any other form of computer-readable medium that may contain computer-executable instructions. Further communication device 76 could be a modem, network card, or any other device to enable the node to communicate with other nodes. It is understood that any node could represent a plurality of interconnected (whether by intranet or Internet) computer systems, including without limitation, personal computers, mainframes, PDAs, and cell phones.

A computer system typically includes at least hardware capable of executing machine readable instructions, as well as the software for executing acts (typically machine-readable instructions) that produce a desired result. In addition, a computer system may include hybrids of hardware and software, as well as computer sub-systems.

Hardware generally includes at least processor-capable platforms, such as client-machines (also known as personal computers or servers), and hand-held processing devices (such as smart phones, personal digital assistants (PDAs), or personal computing devices (PCDs), for example). Further, hardware may include any physical device that is capable of storing machine-readable instructions, such as memory or other data storage devices. Other forms of hardware include hardware sub-systems, including transfer devices such as modems, modem cards, ports, and port cards, for example.

Software includes any machine code stored in any memory medium, such as RAM or ROM, and machine code stored on other devices (such as floppy disks, flash memory, or a CD ROM, for example). Software may include source or object code, for example. In addition, software encompasses any set of instructions capable of being executed in a client machine or server.

Combinations of software and hardware could also be used for providing enhanced functionality and performance for certain embodiments of the present disclosure. One example is to directly manufacture software functions into a silicon chip. Accordingly, it should be understood that combinations of hardware and software are also included within the definition of a computer system and are thus envisioned by the present disclosure as possible equivalent structures and equivalent methods.

Computer-readable mediums include passive data storage, such as a random access memory (RAM) as well as semi-permanent data storage such as a compact disk read only memory (CD-ROM). In addition, an embodiment of the present disclosure may be embodied in the RAM of a computer to transform a standard computer into a new specific computing machine.

Data structures are defined organizations of data that may enable an embodiment of the present disclosure. For example, a data structure may provide an organization of data, or an organization of executable code. Data signals could be carried across transmission mediums and store and transport various data structures, and, thus, may be used to transport an embodiment of the present disclosure.

The system may be designed to work on any specific architecture. For example, the system may be executed on a single computer, local area networks, client-server networks, wide area networks, internets, hand-held and other portable and wireless devices and networks. In that regard, it is understood that the network may be a secure network to comply with patient confidentiality requirements and otherwise protect patient data and/or proprietary information.

A database may be any standard or proprietary database software, such as Oracle, Microsoft Access, SyBase, or DBase II, for example. The database may have fields, records, data, and other database elements that may be associated through database specific software. Additionally, data may be mapped. Mapping is the process of associating one data entry with another data entry. For example, the data contained in the location of a character file can be mapped to a field in a second table. The physical location of the database is not limiting, and the database may be distributed. For example, the database may exist remotely from the server, and run on a separate platform. Further, the database may be accessible across the Internet. Note that more than one database may be implemented.

When a surgeon has performed an orthopedic spinal treatment, the data from that treatment is commonly retained by the surgeon and, in many cases, is submitted to studies of various types for assimilation. The data may be gathered and stored in a database accessible by the modules of the system 10 for future access and analysis. The data may be sorted and organized in various hierarchies. For example, a first level may include generally all received data without limiting the outcomes or patient pathology by type of outcome, anatomical area of treatment, or other specific category. A second level, for example, may filter the general data down to data or studies obtained by various study groups. For example, a spine trauma study group (STSG) may focus on injury to spinal region such as the vertebrae and associated tissue. A third level, may filter data within each of the various study groups. For example, continuing the STSG example, the spinal data may be filtered down to data or studies to a particular region of the spine, such as a lumbar spine study group (LSSG), which may focus on treatments and outcomes in solely the lower back (e.g. lumbar and sacral vertebrae and associated tissue). Similarly, another grouping may filter the spinal data down to data or studies by a cervical spine study group (CSSG), which may concentrate on outcomes and treatments in the upper vertebral region, including the neck and occiput. Yet another grouping may filter the spinal data down to data or studies by a spinal deformity study group (SDSG), which may study and report data concerning treatment of scoliosis and other deformative conditions. Numerous other groupings and divisions may be created to further subdivide the data and studies of the various study groups. The data collected by the surgeon or his or her team at each level may include a variety of numerical, language, image (e.g. radiographic) or other data, and can include data sufficient to perform the related surgical operations. Instructions or training as to the data to be provided by the surgeon or his or her team may be provided by a user interface and/or personal training.

The data from these studies can be provided to one or more software applications in order to derive further information or new views of the data. Examples of such software include the Montreal 3D Radiographic Modeling, Measurement and Surgery Simulation software ("Montreal software"); the TruBalance patient measurement software ("TruBalance software"); and the DRPro radiographic measurement software offered by PhDx eSystems, Inc. of Albuquerque. Other brands or types of software for obtaining, analyzing, or otherwise handling patient data may be used in addition to or instead of one or more of the software applications mentioned above for one or more of the data categories. Also, multiple software applications may be applied to a given set of data. It is understood that data from each study can be assembled together prior to submission to such software, or each study can be treated individually.

Output from the software applications may be routed to one or more databases for storage. These databases may be physically distant from each other, but may be connected via electronic connections, such as hard-wired connections, internet or other network connections, and/or satellite connections. In that regard, in some embodiments the databases may be directly accessible by the modules 12, 14, 16, and 18 of the system 10 for use in the patient diagnosis, analysis, and treatment planning. In other instances, data from these databases and other sources may be compiled to create a master database. It is understood the data need not necessarily reside on a single server or hard-drive system to form the master database. Rather, the databases containing data from each of the studies may feed data into or be accessible via the master database. Further, it is understood that data may be passed to other databases or outputs. Data or other outputs from the database(s) may be output in the form of a report. The report may be in a computer readable form and/or in human intelligible form. In that regard, the report may be utilized by the system 10 and/or a treating physician in determining appropriate treatment options for a patient.

Medical professionals, for example spinal surgeons, may access the database(s) via a software interface or computer network. This assessment, treatment and outcomes modeling software of the system 10 allows entry of data of a current patient for which a diagnosis and/or treatment options and analysis is desired. That data may then be compared to the data available in or through the accessible database(s). If necessary, the data obtained from or through database(s) may be buffered or otherwise copied and transformed, e.g. via mathematical or other algorithm, so that it can be more efficiently compared to the current patient data via human or machine review. The comparisons and/or transformations may be made using the IRT models or equations, in certain embodiments. Such a comparison can be used to obtain records of previous medical cases in which patients having similar characteristics (e.g. gender, height, weight, age or affliction) were treated with various treatments, and their corresponding outcomes. In this way, the medical professional can quickly obtain a view of outcomes of one or more treatments for his or her current patient, and/or the likelihood of a positive outcome for a given treatment. With this information and his or her personal knowledge and experience, the professional can come to a treatment decision or recommendation more quickly, more efficiently, and with greater likelihood of successful treatment outcome.

Other uses can also be made of the outputs of the database(s). In addition to medical professionals studying previous outcomes for guidance on a current patient's case, bioengineers can study outcomes having to do with particular products or afflictions toward improving existing implants or other devices and/or creating new devices and treatment plans. Further, as a repository of clinical and treatment information, the database(s) may also be used by historians, epidemiologists, or others with an interest in such data.

In addition to data communication between medical personnel (physicians, surgeons, medical assistants, etc.), patients, and/or medical device manufacturers, the system 10 may also provide a communication link to a treatment facility. In one embodiment, the system 10 is in communication with a physical therapy treatment facility such that the treating physical therapist may. In other embodiments, the system 10 may be in communication with other treatment facilities or rehab centers. As post-operative therapies can play a significant role in the overall effectiveness of a surgical procedure, in some embodiments post-operative therapies may be a component of the available treatment plans for the patient. In other embodiments, the system 10 may include a separate module for determination of appropriate post-operative therapies based on the treatment plan selected for the patient and/or other factors.

Among other things, there is disclosed a system for use by medical professionals and other experts for assisting them in making decisions on treatments aimed at the desired clinical outcome for the patient. Such systems may include methods for coordinating a number of sources of data and assimilating relevant data to provide actionable information for the professional. Using such information with the appropriate confidence intervals, a surgeon (for example) can come to a clinical decision on treatment based on data of actual patient outcomes relating to identical or similar treatments. In particular embodiments, the data analysis can take the form of an item response theory (IRT) modelization technique that allows a professional to compare his or her patient's data to actual previous patient outcomes data that have been conditioned with a probabilistic treatment result. The system may perform in a methodical and predictable way one or more of the variable or "trade-off" decisions among possible treatment options normally made by skilled professionals.

The methods and systems disclosed herein were originally developed for use with orthopedic surgery cases, and in particular with orthopedic treatments of the spine. Accordingly, the following description will use the context of spinal orthopedic medicine and treatments used therein. It is to be understood that identical or similar methods or systems could be used in other medical fields, such as cardiology or oncology.

Figure 17:
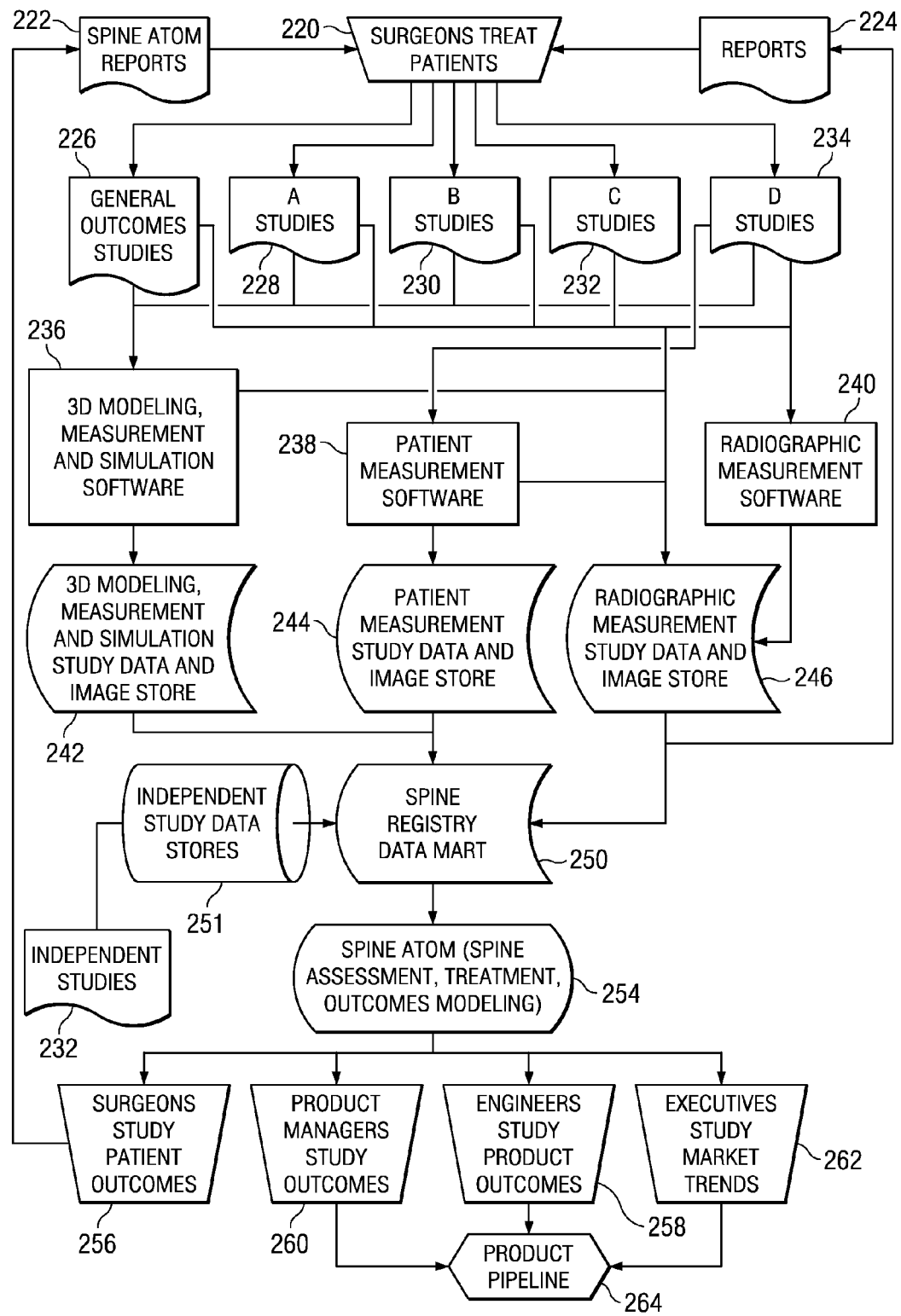
FIG. 17 is a flow chart of a data flow method according to another aspect of the present disclosure.

Referring generally to FIG. 17, shown therein is a flow chart of an embodiment of a data flow method according to another aspect of the present disclosure. As indicated, this embodiment reflects storage, movement and usage of data obtained from treatment of patients. Block 220 reflects that treatment, which in the spinal orthopedic field may include open or minimally-invasive surgery, stabilization through implantation of rods, plates and/or disc prostheses, fusion of one or more vertebral levels via intervertebral cages, placement of osteogenic materials, or many other procedures. The decision as to what treatment to use may come from a surgeon's fundamental knowledge of biology, particularly anatomy, and current and past basic research in the field. The decision may also be influenced via reports or other information of results from other surgeries or treatments, as indicated at blocks 222 and 224, and further discussed below.

When a surgeon has performed an orthopedic spinal treatment, the data from that treatment is commonly retained by the surgeon and, in many cases, is submitted to studies of various types for assimilation. Blocks 226, 228, 230, 232, and 234 indicate such gathering by entities into a repository of outcomes for access and analysis. Block 226 reflects a gathering of outcomes generally, without necessarily limiting outcomes or patient pathology by type of outcome, anatomical area of treatment, or other specific category. Block 228 reflects studies by a study group A. In one exemplary embodiment, study group A is a spine trauma study group (STSG) that focuses on injuries to vertebrae and associated tissue. Block 230 reflects studies by a study group B. In one exemplary embodiment, study group B is a lumbar spine study group (LSSG), which focuses on treatments and/or outcomes in the lower back, (e.g. lumbar and sacral vertebrae and associated tissue). Block 232 reflects a collection of data by a study group C. In one exemplary embodiment, study group C is a cervical spine study group (CSSG), which concentrates on outcomes and treatments in the upper vertebral region, including the neck and occiput. Block 234 shows data collection by a study group D, which in one exemplary embodiment is a spinal deformity study group (SDSG) that focuses on the treatment of scoliosis and other deformative conditions. The data collected by the study groups A, B, C, and D can include a variety of numerical, language, image (e.g. radiographic) or other data, and can include data sufficient to perform the operations noted below. Instructions or training as to the data to be collected by a surgeon or his or her team working within each of the study groups A, B, C, and D is provided in some instances to ensure that all or at least a majority of the pertinent information is collected.

The data from these studies can be provided to one or more software applications in order to derive further information or new views of the data. Examples of such software are indicated in blocks, 236, 238, and 240. Block 236 shows a 3D modeling, measurement, and simulation software. In some instances, the 3D modeling, measurement, and simulation software is the Montreal 3D Radiographic Modeling, Measurement, and Surgery Simulation software ("Montreal software"). The Montreal software takes provided data and provides outputs with radiographic models or other images, provides measurements relevant to the anatomy and procedure, and can create a simulation of surgical procedure(s). Block 238 shows a patient measurement software. In some instances, the patient measurement software is configured to obtain patient balance information, including center-of-balance information. In some embodiments, TruBalance patient measurement software ("TruBalance software") is utilized. Block 140 shows a radiographic measurement software that is utilized to obtain measurements of the patient's anatomical features from a radiographic image. In some instances, DRPro radiographic measurement software offered by PhDx eSystems, Inc. of Albuquerque is utilized. The DRPro software can be used to measure and otherwise obtain data from radiographs or other images. Other brands or types of software for obtaining, analyzing, or otherwise handling patient data could be used in addition to or instead of one or more of the software applications described above one or more data categories. Also, multiple software applications may be applied to a given set of data. In the embodiment of FIG. 17, as one example, output or data from any of the study groups of blocks 226, 228, 230, 232, and 234 can be routed for handling by the radiographic measurement software of block 240. It will be seen that data from each study can be assembled together prior to submission to such software, or each study can be treated individually.

As seen in embodiment of FIG. 17, output from blocks 236, 238, and 240 may be routed to databases for storage. Block 242 indicates a 3-D Modeling, Measurement, and Simulation Study Data and Image Store that includes output of models, measurements, simulations and other images or information from the 3-D modeling, measurement, and simulation software (block 236). Block 244 indicates a Patient Measurement Study Data and Image Store that includes output of the information from the patient measurement software (block 238). Block 246 indicated a Radiographic Measurement Study Data and Image Store that includes radiograph information, study data, and/or other information from the radiographic measurement software (block 240) and/or from studies, such as those indicated in blocks 226, 228, 230, 232, and 234. These databases may be physically distant from each other, but may be connected via electronic connections, such as hard-wired connections, internet or other network connections (wired or wireless), and/or satellite connections.

Data from these databases and other sources can be brought together to a master database, shown in block 250 and labeled "Spine Registry Data Mart." Block 250 brings together data from blocks 242, 244, and 246. The data from the blocks 242, 244, and 246 is aggregated into the database of block 250 in some instances. In other instances, the data from blocks 242, 244, and 246 is accessible from the database of block 250, but not necessarily part of the database of block 250. In the illustrated embodiment, one or more independent databases shown in block 251 are included in or accessible by the master database of block 250. As shown the independent databases 251 are available to the master database via one or more Independent Study Data Stores, shown in block 252. It will be seen that other databases, e.g. databases dedicated to data from other studies noted above, could also feed data into or be accessible via the database in block 250. In some instances, the independent databases include the Scolisoft database or the Spine Tango database. Further, it will also be seen that data can be passed to other databases or outputs. As shown in FIG. 17, data or other output from block 246 may be output in the form of reports, shown generally at block 224. As indicated above, physicians in the course of considering or giving treatment (block 220) may consult such reports.

Medical professionals, for example spinal surgeons, can access this database in block 250 via the software in block 254, labeled "Spine ATOM." This assessment, treatment and outcomes modeling software allows entry of data of a current patient for which a diagnosis and/or treatment options and analysis is desired. That data is then compared to the data available in or through database 250. If necessary, the data obtained from or through database 250 may be buffered or otherwise copied and transformed, e.g. via mathematical or other algorithm, so that it can be more efficiently compared to the current patient data via human or machine review. The comparisons and/or transformations may be made using the IRT models or equations, in certain embodiments. Such a comparison can be used to obtain records of previous medical cases in which patients having similar characteristics (e.g. gender, height, weight, age or affliction) were treated with various treatments, and their outcomes. In this way, the medical professional can quickly obtain a view of outcomes of one or more treatments for his or her current patient, and/or the likelihood of a positive outcome for a given treatment (block 256). With this information and his or her personal knowledge and experience, the professional can come to a treatment decision or recommendation more quickly, more efficiently, and with greater likelihood of successful treatment outcome.

As indicated in FIG. 17, the study of outcomes (block 256) can translate into reports of other information (block 222) that assist the physician in considering options or planning treatment.

Other uses can also be made of the output of the ATOM analysis. In addition to medical professionals studying previous outcomes for guidance on a current patient's case, bioengineers can study outcomes having to do with particular products or afflictions toward improving existing implants or other devices or creating new devices and treatments (block 258). Blocks 260 and 262 represent uses by management to review outcomes for market, treatment and other trends. The data based on blocks 258, 260, and 262 and/or the decisions resulting therefrom are utilized in developing new products and modifying existing products in the product pipeline shown in block 264. As a repository of clinical and treatment information, a database such as that shown in block 250 could also be used by historians, epidemiologists, or others with an interest in such data.

Figure 18:
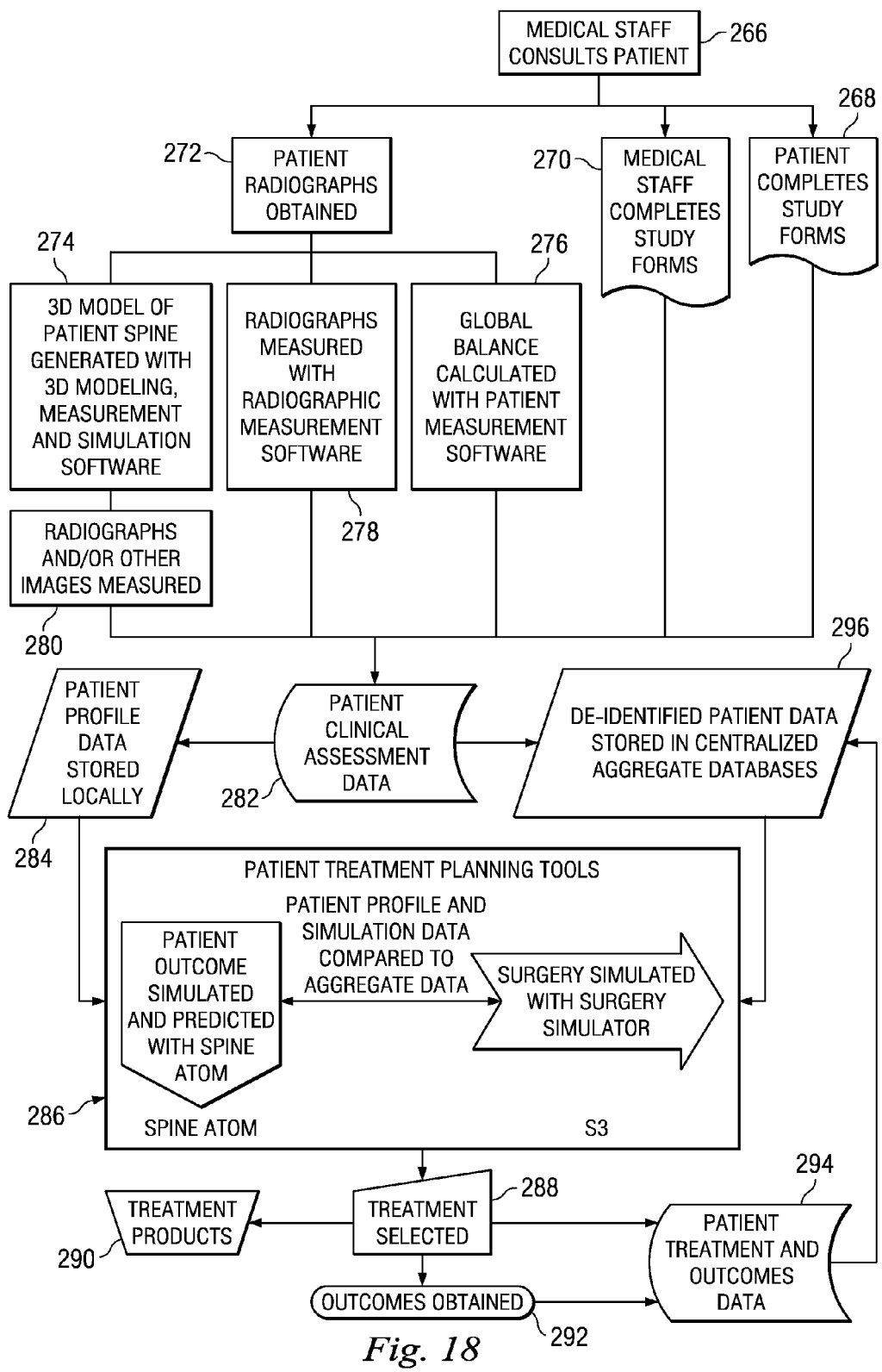
FIG. 18 is a flow chart illustrating a patient diagnostic modeling method according to another aspect of the present disclosure

Referring now generally to FIG. 18, shown therein is an embodiment of a patient diagnostic model according to another aspect of the present disclosure. The model begins generally when medical professional(s) consult with a patient (block 266), either as an initial appointment or through a referral. Again using the context of spinal surgery solely for illustration, at or after such consultation both the patient (block 268) and the professional(s) (block 270) provide information on study forms or in other ways. Such information may include standard information on the physical characteristics and condition of the patient. In a particular embodiment, such information may also include a series of options for the patient and/or the medical professional to select. Such options are geared toward helping to determine and appropriate treatment, as disclosed herein, and could include goals as to post-operative mobility, activity or relative deformity, pre-operative condition, prior surgeries or other treatments, or other factors. The information may also include weighting or come or all factors so as to emphasize one or more factors as the analysis of potential treatments is performed.

In addition, radiographs (e.g. x-rays, MRI images, CT scans) or other images can be taken of the current patient (block 272). Data from these images are taken via software, and in the illustrated embodiment 3-D modeling, measurement, and simulation software is used to generate a three-dimensional model of the patient's spine (block 274), patient measurement software is used to calculate a global balance (block 276), and radiographic measurement software is used to measure the images (block 278). An additional step that can be used is to measure the radiographs and/or the 3-D images generated by the software at block 274 with additional measurement software (block 280). In some instances, software known as Clindexia is utilized at block 280. Generally, these software applications of blocks 274, 276, 278, and 280 transform the raw images into mathematical or other forms that can easily be compared via a computer or similar machine to images or other data from a database (e.g. database 250 of FIG. 17) that have been similarly transformed.

The information from the radiographs or other images and the information from the patient's and medical professional's study forms are combined into a file or database (block 282) in the illustrated embodiment. That patient's clinical assessment data then be used to help the medical professional(s) to select an appropriate treatment, as described above. For example, some or all of the data can be stored in a local file, disc or server (block 284), so that it can be accessed easily by a computer or other processor that is also able to access the information available in or through database 250. Block 286 reflects the analytical process. Two subprocesses are shown in block 286, the first of which is the ATOM process of comparing the current patient's data to aggregate data of other patients and their treatments and outcomes. The second subprocess shown in block 286 is a simulation of surgery based on the current patient's data, including weighted factors concerning the patient's characteristics or desired outcome. This surgical simulation is performed with a software application in some instances. In one particular embodiment, software known as S3 Spine Surgery Simulator is utilized. Using these subprocesses, a professional can select a possible treatment based on the comparison of his or her patient's characteristics and weighted factors to previous patients, treatments and outcomes, and simulate that treatment to calculate the likelihood of a successful outcome (as suggested by the data collected in blocks 270 and 272).

One or both subprocesses shown in block 286 may be used, and either or both may be used multiple times as the surgeon or other medical professional may desire, so that the professional can evaluate as many treatment scenarios as he or she deems appropriate. Once the subprocesses have been run, the professional can select a treatment (block 288) that best meets the patient's characteristics, affliction and stated goals or weighted outcome factors, and appears to be most likely to achieve the desired outcome. That selection is used in choosing implants, devices, compositions, and other products for the treatment (block 290), in preparing for an implementing the treatment and obtaining an outcome (block 292), and in developing data from the treatment and the outcome (block 294).

Block 296 in the embodiment of FIG. 18 indicates the routing and storage of the current patient's data as a part of studies and/or other collection of data into databases such as those noted above with respect to FIG. 17. Once that data is appropriately de-identified with the particular patient, so as to preserve confidentiality and impartially of the data, and to comply with applicable laws, it can optionally be entered into such databases, e.g. following block 282. As discussed above, data from those databases is used in at least the comparison(s) performed at block 286. Additionally, the data obtained in block 294 of the outcome of the current patient's procedure can be transferred to such databases, again after being appropriately de-identified. This new data is the feedback to the databases that provides confirmation of prior information and/or new information from which professionals can learn in the future.

Figure 19:
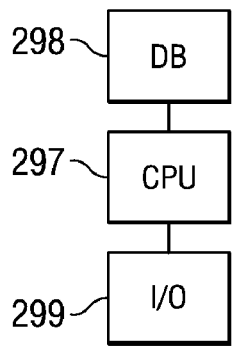
FIG. 19 is a diagrammatic schematic view of a system for performing the methods disclosed herein according to one aspect of the present disclosure

FIG. 19 shows schematically an embodiment of a system that is used to perform the methods disclosed herein according to one aspect of the present disclosure. A processor or central processing unit 297 is shown electronically linked to one or more databases 298 and to one or more input/output devices 299. More than one processor may be used, in the form of one or more computers or other devices, or a single processor may be programmed to accomplish tasks discussed herein. Processor 297 may be a part of a network, such as the internet. Databases such as those described above may be individually linked to processor 297, as the line between blocks 297 and 298 suggests, or may be physically or electronically combined so that a single electronic link exists between processor 297 and database(s) 298. Input/output devices 299 may be physically proximate or remote items such as disc drives, monitors, printers, or other devices for inputting and outputting information from processor(s) 297. Thus, current patient information may be inputted via input/output device(s) 299 to processor(s) 297, which can compare that information (as discussed herein) to data from database(s) 298. An output of the comparison(s) may be received via input/output device(s) 299. Processor(s) 297 may also be programmed to perform treatment simulations (as discussed herein), again with output being received via input/output device(s) 299.

The methods described above can be performed in any of a variety of ways. In one embodiment, the data are transferred to electronic media, is they are not taken or recorded immediately in that form, and are similarly stored in such media. The various databases and software discussed above may be available at a single geographic location, or may be linked together electronically or simply accessible by appropriate electronic devices. As one example, the databases may be accessible to a particular computer via a network, such as intranet, a dedicated network, or the internet, and the particular computer may have the software necessary to access the data and make the comparisons and analyses noted above.

With the above described embodiments, an algorithm, or expert system to provide medical personnel involved with patient care a modelization technique for optimizing the treatment of the patient. Such optimization is created through assessment factors (e.g. characteristics of the patient and desired goals), treatment factors (e.g. efficacy or invasiveness), and outcome factors (e.g. desired post-operative condition) relative to a pathology of a patient's condition. Such a treatment algorithm can be derived from a compilation of aggregated study data to which weighted factors selected by medical professionals are applied. The weighted factors are provided as options in answering questions in one or more study questionnaires. From those weighted factors and the aggregated data, it is contemplated that medical professionals may identify a representative or simulated patient from within the aggregated data set. Once that particular patient or data simulating a particular patient is found, the professional may model a variety of clinical outcomes parameters based on a set of initial conditions and proposed treatment alternatives. Each proposed treatment alternative will provide a likely outcome or a range of likely outcomes, and the medical professional can evaluate the treatment alternatives and their risks and rewards. With the clinical outcomes modeled and the results displayed with respective confidence intervals or levels for each outcome related to the particular treatment options, the medical personnel can make the appropriate decisions for treating the patient with a balanced trade-off of parameters important to them. Importantly, the medical personnel's decision can be made from actual patient data relative to a similar condition that represents their particular patient's problem.

Figure 20:
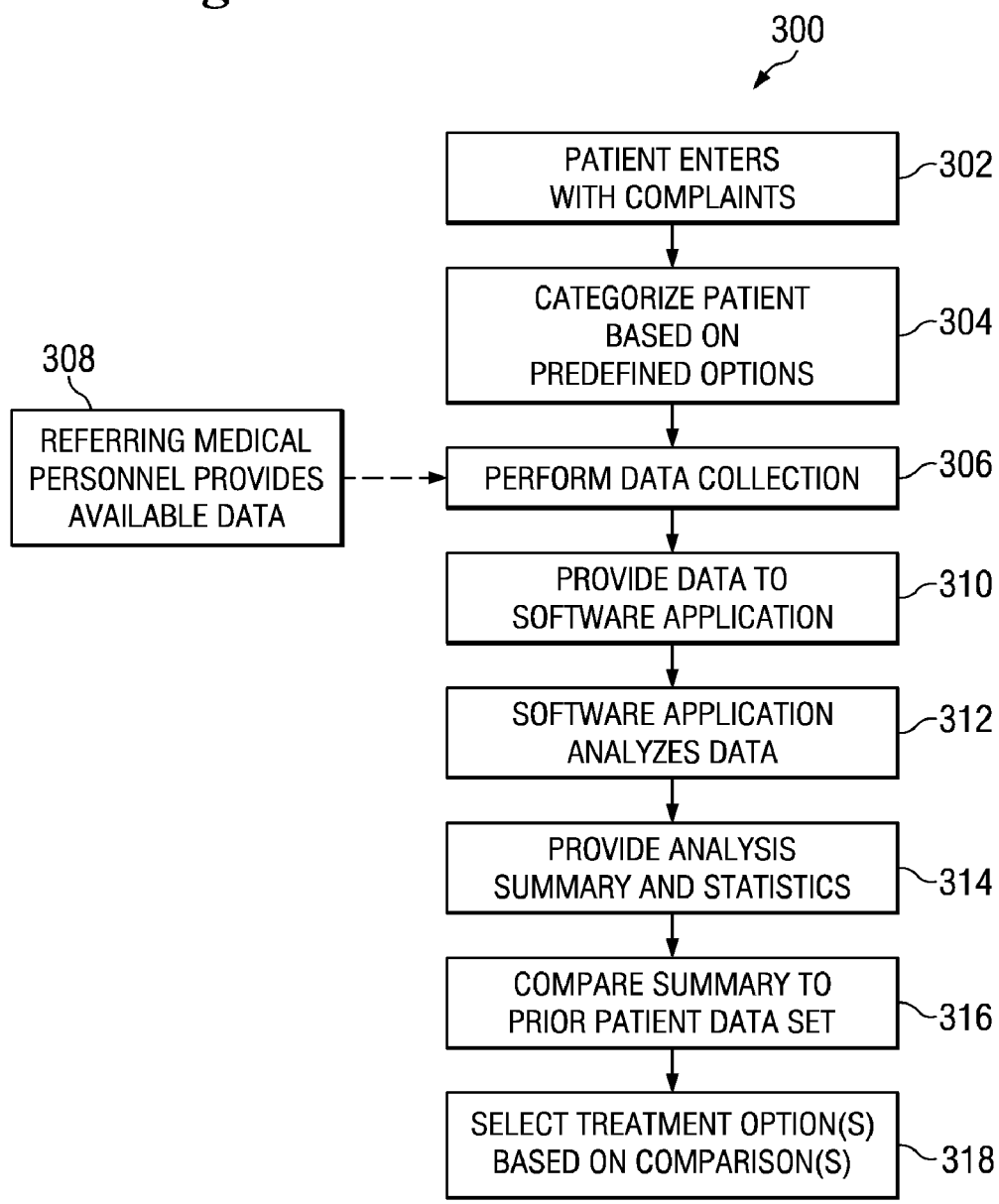
FIG. 20 is a flow chart illustrating a method of collecting and assessing data associated with a method for diagnosing a patient and selecting available treatment options for the patient according to another embodiment of the present disclosure.
Figure 21:
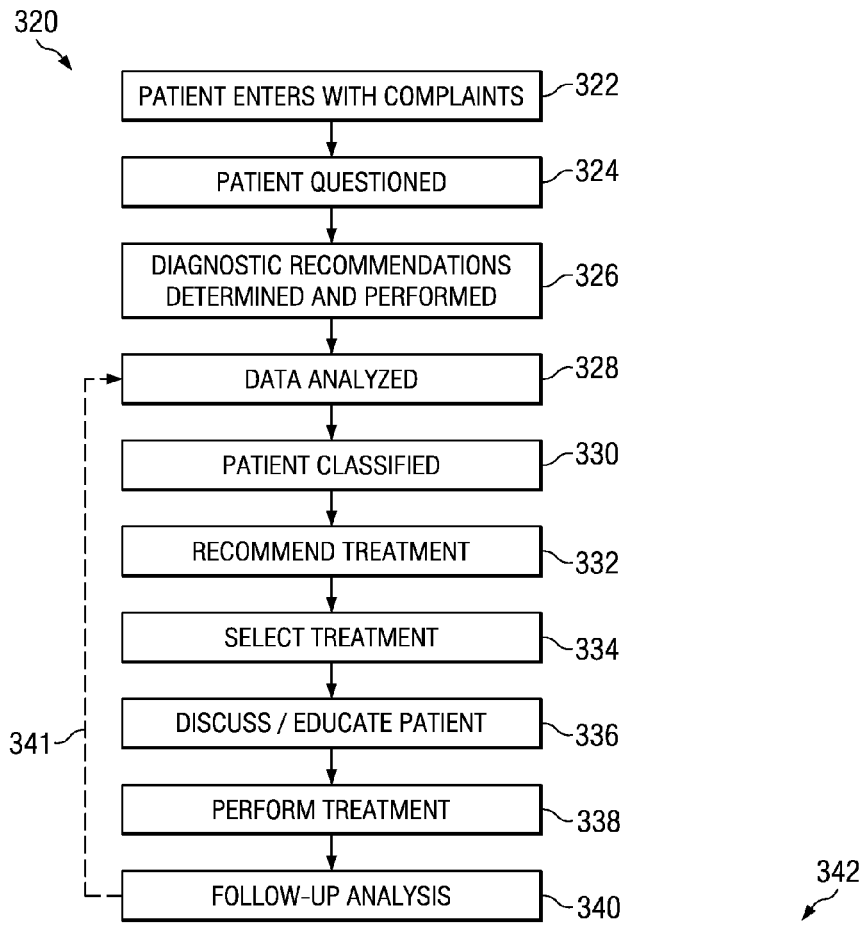
FIG. 21 is a flow chart illustrating a method for diagnosing a patient, identifying available treatment options for the patient, selecting a treatment option for the patient, and performing the selected treatment option according to another embodiment of the present disclosure.
Figure 22:
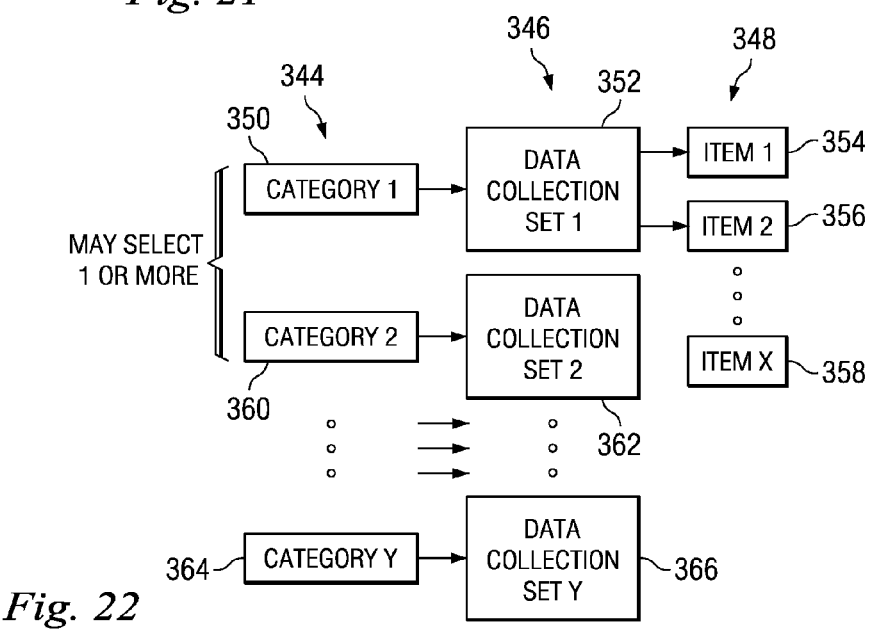
FIG. 22 is a diagrammatic schematic view of a data structure for use with the methods of FIGS. 20 and 21 according to one embodiment of the present disclosure.

Referring now to FIGS. 20-22, shown therein is are methods for obtaining and analyzing patient information for diagnosing and treating a patient according to another embodiment of the present disclosure. Referring more specifically to FIG. 20, shown therein is a flow chart illustrating a method of collecting and assessing data associated with diagnosing a patient and selecting available treatment options for the patient according to another embodiment of the present disclosure.

Referring more specifically to FIG. 20, shown therein is a flow chart illustrating a method 300 for diagnosing a patient, identifying available treatment options for the patient, selecting a treatment option for the patient, and performing the selected treatment option according to another embodiment of the present disclosure. The method 300 begins at step 302 when the patient enters with complaints indicative of a medical condition. Based on the types of complaints the patient has, the method 300 continues at step 304 by categorizing the patient. In that regard, in some embodiments categorizing the patient comprises identifying one or more predetermined categories that are associated with the symptoms or complaints indicated by the patient. The predetermined categories are provided to the treating physician in some instances. In other instances, the treating physician or other medical personnel at least partially defines the categories. In some embodiments, the categories are at least partially defined or organized as set forth in FIG. 22 discussed in greater detail below. Generally, each category defines a series or set of data points that are useful in evaluating the patient. For example, in some embodiments where a patient complains of pain in a bony region, the data set defined by the category includes obtaining an x-ray of the problem area. Similar correlations between the patient's symptoms and the desired medical information and/or tests associated with that symptom are defined for each category.

After categorizing the patient at step 304, the method 300 continues at step 306 with collecting the data associated with each category in which the patient has been categorized. Accordingly, the extent of the data collection will vary depending on the categorization of the patient at step 304. In some instances, at least some of the data collection is provided by the patient's primary care physician or referring physician as indicated by step 308. In that regard, the patient has often previously undergone testing and/or imaging included in the categorization data. In some instances, this information is provided from the prior medical personnel to the current medical personnel over a telecommunications network, such as the internet, phone system, fax, or otherwise. In one particular embodiment, the data is stored in a database accessible by the current medical personnel.

In addition to any data that is available from previous medical personnel, the remaining data that is suggested to be collected for each category is obtained from the patient. The data may include standard information on the current physical characteristics (e.g., height, weight, mobility, etc.) and condition of the patient. Further, the data may include goals as to post-treatment mobility, activity, or relative deformity of the patient. At least some of the data is obtained by determining the answers to a series of diagnostic questions defined by each category. In one particular category, the diagnostic questions include questions such as: How far can the patient walk without pain? Does the patient have pain lying down? Does the patient have pain sitting? Does the patient have pain standing? Does the patient have back pain with leg pain? If yes, is the leg pain localized or radiating? These are exemplary questions and are not to be considered limiting. Numerous other questions may be utilized depending on the categorization of the patient. In addition, the questions within each category may be nested such that subsequent questions depend on the answers to previous questions. Further, some or all of the questions may be weighted so as to emphasize one or more factors associated with a category. That is, particular questions and the resultant information provided by the answers to those questions are given more importance than other questions and answers. In that regard, some questions and/or data will be optional for a particular category. In some instances, the treating physician or medical personnel may determine the questions and/or data to be included in each category. In some embodiments, the questions of associated with each category are provided to the patient and/or medical personnel in an interactive computer program.

In addition to or in lieu of the diagnostic questions for each category, the data collection step 306 may include other types of patient analysis depending on the category. For example, in some embodiments imaging techniques are utilized to obtain additional data regarding the patient. For example, in some embodiments radiographic images of the patient's anatomy are obtained. The radiographic images are then analyzed to identify the relevant data associated with the categorization of the patient. In some embodiments, the patient's motion sequence and/or range of motion in one or more anatomical areas is a data point to be considered in evaluating the patient. Accordingly, in some embodiments the patient is put through a series movements appropriate to determine the patient's motion sequence and/or range of motion in the one or more anatomical areas.

In other embodiments, the imaging study includes obtaining patient images through the use of magnetic resonance imaging ("MRI"), computed tomography ("CT"), video fluoroscopy, and/or other imaging techniques. In some embodiments, the imaging study includes techniques as described in commonly owned U.S. patent application Ser. No. 11/697,426 filed Apr. 6, 2007 and titled "System and Method for Patient Balance and Position Analysis", herein incorporated by reference in its entirety. In general, the imaging study obtains images of the patient's anatomy that are utilized to obtain data points as suggested by the categorization of the patient in step 304.

In some embodiments, the imaging study includes tracking the movement of anatomical features of the patient using sensors. In some embodiments the sensors are implantable and are placed in direct contact with and/or within the relevant anatomical feature(s) of the patient. In other embodiments, the sensors remain outside of the patient's body, but are positioned in close proximity to the anatomical feature(s) of interest. For example, in some embodiments the imaging study tracks the position of at least some of a patient's vertebrae. In one embodiment, a sensor is implanted into each vertebra and the location of the vertebra is tracked using the sensor. In another embodiment, a sensor is placed outside the patient's body adjacent the spinous process. The location of the spinous process and, in turn, the vertebra are tracked using the sensor. In some embodiments, the position of the sensors and anatomical features are tracked while the patient is put through a particular motion sequence or protocol. For example, in one embodiment the patient is asked to walk on a treadmill. The position of the sensors and anatomical features are tracked and correlated to the patient's gait cycle. It is understood that these described uses of sensors are merely exemplary and should not be considered limiting. Sensors, implantable or otherwise, may be utilized in numerous other combinations and ways to track the position of anatomical features during the imaging study.

Additional questions, imaging, and/or tests are utilized to obtain data regarding the patient during step 306 as determined by the treating physician or other medical personnel.

After the relevant data has been collected at step 306, the method 300 continues at step 310 by providing the data to one or more software applications. In some embodiments, the answers to any questions prompted by the categorizations are input directly into the relevant software application. With respect to the imaging data, in some embodiments the data from the imaging study is provided to one or more software applications in order to derive further information and/or new views of the imaging data. Various brands or types of software for obtaining, analyzing, or otherwise handling patient data may be used for one or more of the data categories. Also, multiple software applications may be applied to a given set of data. It is understood that data from each study can be assembled together prior to submission to such software, or each study can be treated individually. In some embodiments, the Montreal software is used to generate a three-dimensional model of the patient's spine, the TruBalance software is used to calculate a global balance for the patient, and the DRPro software is used to measure the images. In some embodiments, the images are provided to software known as Clindexia for measuring the images. These software applications can transform the raw images into mathematical or other forms that can be utilized by other software applications and/or manipulated via a computer system and compared to other images and/or other data sets.

After the data has been provided to the respective software application(s) at step 310, the method 300 continues with step 312 in which the software application(s) analyzes the data. Generally, the software application synthesizes the information obtained in step 306 to identify any abnormal medical conditions afflicting the patient. In some embodiments, the analysis of the data includes creating a 3-D and/or 2-D animated model of the patient's anatomy. This model may be visually represented, such as on a computer screen or otherwise, in some embodiments. Generally, the animated model is substantially based on the data obtained in step 306. In some embodiments, the animated model is used to highlight the problem areas and/or times in the patient's anatomical motion sequence. In that regard, in some instances the model includes layers of anatomical features that are selectively included or removed. For example, in one embodiment the patient's motion anatomy is grouped into layers according to the various types of anatomical tissue, such as bones, cartilage, ligaments, tendons, muscles, and/or combinations thereof. The animated model then analyzes motion according to each grouping of anatomical tissue and the interactions therebetween.

In some embodiments, the animated model combines diagnostic tests with the imaging study. For example, in some embodiments the animated model combines muscle monitoring with the imaging study to identify muscle contractions and tensions during a motion sequence or protocol. The results of the muscle monitoring are combined with the other imaging data to provide additional details and/or realism to the animated model. In other embodiments, the animated model utilizes center-of-balance or center-of-gravity data for the patient obtained during the motion sequence or protocol. Muscle monitoring and center-of-balance data are merely examples of the types of additional data that may be combined with the imaging data in forming the animated model. Other types of the patient data may also be utilized. In that regard, in some embodiments the treating physician or medical personnel selects the types of patient data to be used in formulating the animated model.

The animated model includes additional features to allow medical personnel and/or a computer system to analyze the patient. In that regard, in some embodiments the animated model includes a stress grid overlay that indicates potential areas of increased stress or strain on the patient's anatomy, such increased muscle activity; overstretching of muscles, ligaments, and/or tendons; friction between bones; and/or other areas of stress/strain. In some embodiments the model allows for zooming, panning, or otherwise changing the orientation of the view of the patient's anatomy. Users can adjust the orientation of the model relative to particular anatomical features to better observe or isolate a potential problem area. Similarly, the animated model allows a user to pause, rewind, slow down, and/or speed up simulation of a motion sequence to better observe a potential problem. Further, the animated model allows 3-D and/or 2D tracking of specific anatomical features through the motion sequences. In some embodiments, the software application that creates the animated model also highlights potential problem areas automatically based on a comparison to a standardized model. In other embodiments, the treating physician or medical personnel notes the potential problem areas based on their own observations. In some embodiments, the problem areas are identified by the software application and/or medical personnel by recognizing an abnormal motion pattern(s). In some embodiments, the model is utilized internally by the software application to identify the patient's potential medical problems, but no visual representation of the model is created.

After the software application analyzes the data at step 312, the method 300 continues with step 314 where an analysis summary and accompanying statistics are provided. Generally, the summary provides information important to the diagnosis and subsequent treatment of the patient's medical condition. In some embodiments, the summary identifies such things as damaged anatomical features or areas, limited ranges of motion, and/or other data related to the patient's medical condition. The information provided by the summary is at least partially determined by categorization of the patient in step 304 and may be further defined by the medical personnel. For example, in some embodiments the medical personnel selects or otherwise accesses the particular information or data sets they deem to be most important in diagnosing and treating the patient. The statistical summary also provides a list of possible causes for the medical condition and/or identifies possible relationships between abnormal motion patterns in some embodiments.

After the analysis summary has been provided at step 314, the method 300 continues with step 316 where the analysis summary is compared to a prior patient data set. In that regard, there are multiple types of prior patient data sets that may be used. The particular prior patient data set utilized is determined by the availability of the data sets and/or physician preference. In some embodiments, the multiple prior patient data sets are groupings within a single larger data set. In other embodiments, the prior patient data sets are unrelated, individual data sets. Examples of the different types of prior patient data sets include a particular physician's own prior patients; an aggregated collection of patients from multiple physicians, hospitals, and/or studies; patients from specific medical personnel, such as a renowned physician, a mentor, a consultant, or other medical personnel; and/or a patient wizard using a probabilistic matching system (i.e., grouping of patients with similar attributes to the current patient). In some embodiments, the treating physician or other medical personnel at least partially defines or selects the parameters of the prior patient data set to be used. In some embodiments, the prior patient data set is a collection of prior patients having similar medical conditions, medical histories, and/or patient profiles to the current patient. The prior patient data sets include the selected treatment plans and relative success of those plans for the prior patients. Accordingly, the current patient's physical characteristics and attributes can be compared to prior patients with similar characteristics and attributes. Then, the one or more treatment options that have been successful for prior patients with characteristics and attributes similar to the current patient may be identified.

After the patient analysis summary has been compared to the prior patient data set(s) at step 316, the method 300 continues with the selection of a appropriate treatment option(s) at step 318. In some embodiments, the comparison of the patient analysis summary and the prior patient data will identify a single treatment plan that is clearly considered best for the patient. However, in other embodiments a plurality of treatment plans are identified by the comparison as possible treatment plans for the current patient. In such embodiments, the plurality of treatment options are sorted and/or screened to further narrow the treatment options. In some instances, the treatment options are screened based on physician preference. For example, if a physician prefers a particular surgical procedures or approach, then the available treatment options are limited to those that utilize the preferred procedure or approach. As another example, the treatment options are sorted or ranked based on the likelihood of success of the treatment plan based on the data for previous patients having a similar profile to the current patient. Similarly, in some embodiments the treatment options are sorted or ranked based on the previous procedures performed by the treating physician/surgeon and the relative success of those procedures. Based on the comparisons to prior patient data, physician preferences, and likelihood of success a specific treatment plan is selected for the patient.

Referring more specifically to FIG. 21, shown therein is a flow chart illustrating a method 320 for data collection and analysis according to another embodiment of the present disclosure that is used in conjunction with a method of diagnosing a patient, identifying available treatment options for the patient, selecting a treatment option for the patient, and performing the selected treatment option, such as method 300 described above. In that regard, some of the steps of the method 320 are substantially similar to some of the steps of the method 300 where the steps of the method 300 are focused on data collection and/or data analysis.

The method 320 begins at step 322 when the patient enters with complaints indicative of a medical condition. The method 320 continues at step 324 where the patient is asked a series of questions and/or is otherwise assessed. Generally, the questions and/or assessment will be focused around the physical symptoms associated with the patient's complaints. These initial questions are focused on identifying potential medical problems of the patient. Additional questions and information will be obtained based on the answers to the questions of step 324. For example, in the current embodiment the method 320 continues at step 326 where the appropriate diagnostic recommendations are determined. The diagnostic recommendations comprise the medical tests, imaging, and/or additional questions that the patient should be put through based on the answers to the initial questions/assessment of step 324.

In some embodiments, the diagnostic recommendations are based on grouping the patient into categories based on the responses of step 324. In that regard, in some embodiments categorizing the patient comprises identifying one or more predetermined categories that are associated with the symptoms or complaints indicated by the patient. The predetermined categories are provided to the treating physician in some instances. In other instances, the treating physician or other medical personnel at least partially define the categories. In some embodiments, the categories are at least partially defined or organized as set forth in FIG. 22.

Referring more specifically to FIG. 22, shown therein is a diagrammatic schematic view of a data structure 342 for use with the methods 300, 320 according to one embodiment of the present disclosure. Generally, the data structure 342 comprises a series of categories 344 that each define a corresponding data set 346. Each data set 346, in turn, comprises a plurality of data points or items 348. The items 348 represent the specific data, images, answers to questions, etc. that are recommended to be obtained for each category 344. In that regard, the categories 344 may each be associated with a particular patient symptom or complaint. For example, Category 1 (block 350) may represent a particular patient symptom such as lower back pain. In turn, the Data Collection Set 1 (block 352) comprises a plurality of items, namely Item 1 (block 354), Item 2 (block 356), and so on to Item X (block 358). Each Item 1, 2, and X (354, 356, 358) represents a specific data point, image, answer to a question, or other information that is recognized as being beneficial in diagnosing the medical condition of a patient having lower back pain. The items in each category represent data or information that may be useful in evaluating and diagnosing the patient. For example, in some embodiments where a patient complains of pain in a bony region, the data collection set defined by the category includes an item that requires obtaining an x-ray of the problem area. Similar correlations between the patient's symptoms and the desired medical information and/or tests associated with that symptom are defined for each of the categories of the data structure 342.

In some instances, some of the Items 1-X of the Data Collection Set 1 (block 352) are optional. That is, some of the items included in the Data Collection Set 1 (block 352) are not necessary for diagnosing the patient, but may be beneficial in some instances. Similarly, some of the items included in the Data Collection Set 1 (block 352) are necessary for a proper diagnoses of the patient and, therefore, should always be obtained. In some embodiments, the required and optional items are predetermined and stored within a software application for each category. In some embodiments, the treating physician or medical personnel determines and/or modifies what items are required and/or optional for a specific category. In some embodiments, the items are weighted by importance for each category. That is, items may not be given a required or optional label, but rather will be rated based on the relative importance and/or benefit of the item to the diagnosis of the patient. As shown, the data structure 342 includes a plurality of categories each with its own data collection set. For example, the current data structure 342 includes Category 1 (block 350) and its corresponding Data Collection Set 1 (block 352); Category 2 (block 360) and its corresponding Data Collection Set 2 (block 362); through Category Y (block 364) and its corresponding Data Collection Set Y (block 366).

Referring again to FIG. 21, step 326 also includes obtaining the diagnostic recommendations. For example, after grouping the patient into one or more of the categories 344, the items 348 associated with each of the categories are obtained. Accordingly, the extent of the data collection/diagnostic recommendations will vary depending on the categorization of the patient. In some instances, at least some of the data collection is provided by the patient's primary care physician or referring physician. In that regard, the patient has often previously undergone testing and/or imaging that are included in the item lists of the categories. In some instances, this information is provided from the prior medical personnel to the current medical personnel over a telecommunications network, such as the internet, phone system, fax, or otherwise. In one particular embodiment, the data is stored in a database accessible by the current medical personnel. In addition to any data that is available from previous medical personnel, the remaining items that are suggested to be collected for each category are obtained from the patient. These items may include standard information on the current physical characteristics (e.g., height, weight, mobility, etc.) and condition of the patient. Further, the items may include goals as to post-treatment mobility, activity, or relative deformity of the patient. At least some of the items are obtained by determining the answers to a series of diagnostic questions associated with a particular category. In that regard, the questions within each category may be nested such that subsequent questions depend on the answers to previous questions. Further, some or all of the items may be weighted so as to emphasize one or more factors associated with a particular category. That is, particular items and the resultant information provided thereby are given more importance than diagnostic items.

The data collection sets include various types of items depending on the category. For example, in some embodiments imaging techniques are utilized to obtain additional data regarding the patient. In particular, in some embodiments radiographic images of the patient's anatomy are obtained. The radiographic images are then analyzed to identify the relevant data associated with a particular item. In some instances, the radiographic or other images comprise the item to be collected. In some embodiments, the patient's motion sequence and/or range of motion in one or more anatomical areas is an item to be obtained in evaluating the patient. Accordingly, in some embodiments the patient is put through a series movements appropriate to determine the patient's motion sequence and/or range of motion in the one or more anatomical areas. In other embodiments, the items include obtaining patient images through the use of magnetic resonance imaging ("MRI"), computed tomography ("CT"), video fluoroscopy, and/or other imaging techniques. In general, the imaging obtains images of the patient's anatomy that are utilized to obtain data points or items as set forth in the data collection set for each category associated with the patient.

After the relevant informational items have been determined and collected at step 326, the method 320 continues at step 328 where the data is analyzed. In some embodiments, the data is provided to one or more software applications for analysis. In that regard, in some embodiments the answers to questions included in the item list for categorizations are input directly into the relevant software application. With respect to the imaging data, in some embodiments the data from the imaging is provided to one or more software applications in order to derive further information and/or new views of the imaging data. Various brands or types of software for obtaining, analyzing, or otherwise handling patient data may be used for one or more of the data categories. Also, multiple software applications may be applied to a given set of item data. It is understood that data from each study can be assembled together prior to submission to such software, or each study can be treated individually. In some embodiments, these software applications transform the raw images into mathematical or other forms that can be utilized by other software applications and/or manipulated via a computer system and compared to other images and/or other data sets.

Generally, the software applications synthesize the information to identify any abnormal medical conditions afflicting the patient. In some embodiments, the analysis of the data includes creating a 3-D and/or 2-D animated model of the patient's anatomy. This model may be visually represented, such as on a computer screen or otherwise, in some embodiments. Generally, the animated model is substantially based on the data obtained in step 306. In some embodiments, the animated model is used to highlight the problem areas and/or times in the patient's anatomical motion sequence. In that regard, in some instances the model includes layers of anatomical features that are selectively included or removed. For example, in one embodiment the patient's motion anatomy is grouped into layers according to the various types of anatomical tissue, such as bones, cartilage, ligaments, tendons, muscles, and/or combinations thereof. The animated model then analyzes motion according to each grouping of anatomical tissue and the interactions therebetween.

In some embodiments, the animated model combines diagnostic tests with the imaging study. For example, in some embodiments the animated model combines muscle monitoring with the imaging study to identify muscle contractions and tensions during a motion sequence or protocol. The results of the muscle monitoring are combined with the other imaging data to provide additional details and/or realism to the animated model. In other embodiments, the animated model utilizes center-of-balance or center-of-gravity data for the patient obtained during the motion sequence or protocol. Muscle monitoring and center-of-balance data are merely examples of the types of additional data that may be combined with the imaging data in forming the animated model. Other types of the patient data may also be utilized. In that regard, in some embodiments the treating physician or medical personnel selects the types of patient data to be used in formulating the animated model.

The animated model includes additional features to allow medical personnel and/or a computer system to analyze the patient. In that regard, in some embodiments the animated model includes a stress grid overlay that indicates potential areas of increased stress or strain on the patient's anatomy, such increased muscle activity; overstretching of muscles, ligaments, and/or tendons; friction between bones; and/or other areas of stress/strain. In some embodiments the model allows for zooming, panning, or otherwise changing the orientation of the view of the patient's anatomy. Users can adjust the orientation of the model relative to particular anatomical features to better observe or isolate a potential problem area. Similarly, the animated model allows a user to pause, rewind, slow down, and/or speed up simulation of a motion sequence to better observe a potential problem. Further, the animated model allows 3-D and/or 2D tracking of specific anatomical features through the motion sequences. In some embodiments, the software application that creates the animated model also highlights potential problem areas automatically based on a comparison to a standardized model. In other embodiments, the treating physician or medical personnel notes the potential problem areas based on their own observations. In some embodiments, the problem areas are identified by the software application and/or medical personnel by recognizing an abnormal motion pattern(s). In some embodiments, the model is utilized internally by the software application to identify the patient's potential medical problems, but no visual representation of the model is created.

After the data has been analyzed at step 328, the method 320 continues with step 330 where the patient is classified based on the identified medical conditions. In that regard, the patient is classified based on the data/results provided in response to the items obtained in the data collection sets. Generally, the patient is classified based on information that is important to the diagnosis and subsequent treatment of the patient's medical condition. In some embodiments, the patient is classified based on such things as the damaged anatomical features or areas, extent of limited range of motion, and/or other data related to the patient's medical condition.

After the classification of the patient at step 330, the method 320 continues with step 322 where a treatment plan is recommended for the patient. In some instances, the patient's data is compared to a prior patient data set for determining an appropriate treatment plan. In that regard, there are multiple types of prior patient data sets that may be used. The particular prior patient data set utilized is determined by the availability of the data sets and/or physician preference. In some embodiments, the multiple prior patient data sets are groupings within a single larger data set. In other embodiments, the prior patient data sets are unrelated, individual data sets. Examples of the different types of prior patient data sets include a particular physician's own prior patients; an aggregated collection of patients from multiple physicians, hospitals, and/or studies; patients from specific medical personnel, such as a renowned physician, a mentor, a consultant, or other medical personnel; and/or a patient wizard using a probabilistic matching system (i.e., grouping of patients with similar attributes to the current patient). In some embodiments, the treating physician or other medical personnel at least partially defines or selects the parameters of the prior patient data set to be used. In some embodiments, the prior patient data set is a collection of prior patients having similar medical conditions, medical histories, and/or patient profiles to the current patient. The prior patient data sets include the selected treatment plans and relative success of those plans for the prior patients. Accordingly, the current patient's physical characteristics and attributes can be compared to prior patients with similar characteristics and attributes. Then, the one or more treatment options that have been successful for prior patients with characteristics and attributes similar to the current patient may be identified.

After a treatment plan has been recommended at step 332, the method 320 continues with the selection of a appropriate treatment plan at step 334. In some embodiments, the comparison of the patient analysis summary and the prior patient data will identify a single treatment plan that is clearly considered best for the patient. In such instances, the single treatment plan will be selected at step 334. However, in other embodiments a plurality of treatment plans are identified by the comparison as possible treatment plans for the current patient. In such embodiments, the plurality of treatment options are sorted and/or screened to further narrow the treatment options. In some instances, the treatment options are screened based on physician preference. For example, if a physician prefers a particular surgical procedures or approach, then the available treatment options are limited to those that utilize the preferred procedure or approach. As another example, the treatment options are sorted or ranked based on the likelihood of success of the treatment plan based on the data for previous patients having a similar profile to the current patient. Similarly, in some embodiments the treatment options are sorted or ranked based on the previous procedures performed by the treating physician/surgeon and the relative success of those procedures. Based on the comparisons to prior patient data, physician preferences, and likelihood of success a specific treatment plan is selected for the patient.

After selecting a treatment plan at step 334, the method 320 continues at step 336 by discussing and/or educating the patient about the selected treatment option. In that regard, the results of the analyses and modeling (if performed) are shown and/or explained to the patient to support the decision to go with a particular treatment plan. Further, in the case of a treatment plan that includes inserting an implant or otherwise employing a medical device, the patient may be given access to additional product information regarding the medical device. In some embodiments, discussing the treatment option with the patient is accomplished over the internet, an intranet, computer network, telecommunications network, or other type of remote connection. In that regard, the link between the patient and the medical professional may be a secure link or secured communication channel so as to protect the patient's confidentiality. In some instances, the treatment options are provided over a secure website. The patient is provided access to the secure website via a username and password associated with the patient. In addition to providing the patient information regarding the selected treatment option(s), the patient interface also provides the patient with the ability to ask questions. In some embodiments, the interface includes a query box that is filled out and submitted by the patient, which a medical professional replies to. In other embodiments, the interface is in the form of a chat or instant messaging session. The patient may ask questions over the chat session and the medical personnel can provide answers to these questions immediately or seek answers to the questions and reply to the patient at a later time. In yet other embodiments, the patient interface may be combined with video-conferencing or telephonic-conferencing to provide additional information and opportunities for questions to the patient.

After selection of the treatment option at step 334 and education of the patient at step 336, the method 320 continues with step 338 in selected treatment plan is executed. The treatment plan is executed in accordance with the planning that has occurred in the previous steps or as part of step 338. In that regard, in some instances of a surgical procedure the procedure is monitored intra-operatively to ensure compliance with the planned procedure. The actual surgical procedure, as monitored, is compared in real-time, or approximately real-time, to the planned treatment. Thus, the actual placement of an implant and/or fixation devices is compared to the intended placement and/or associated error fields as defined in the treatment plan. In this manner, an analysis of the placement of the surgical components is performed before the patient leaves the operating room. In that regard, the actual surgical procedure is modified as needed to ensure that it coincides with the error fields of the planned treatment. Any adjustments that need to be made to comply with the treatment plan can be accomplished without the need for a revision surgery or a return to the operating room.

After executing the treatment plan or at least a part thereof at step 338, the method 320 continues with step 340 in which a post-treatment, follow-up analysis is performed. In some embodiments, the post-treatment analysis is substantially similar to steps 324, 326, and/or 328 described above. In some embodiments, the post-treatment analysis step 340 includes comparing the predicted results of the treatment plan to the actual results of the treatment. Any discrepancies are identified and utilized to improve the correlation between the predicted results and the actual results of the treatment plan, as indicated by the feedback loop of step 341. In that regard, in some embodiments the parameters utilized for creating the models are updated and modified based on the identified discrepancies. Ideally, the predicted results are substantially similar to the actual results of the treatment plan. In some embodiments, the post-treatment analysis is performed at set intervals after the initial treatment. In one particular embodiment, the patient goes through post-treatment analysis at least at 2 weeks, 6 weeks, and 3 month intervals after the initial treatment.

By monitoring the resultant data from each patient for each treatment plan, a statistical correlation between medical conditions and treatment options is established. This statistical correlation is utilized in selecting the treatment plans for subsequent patients. The current patient's resultant data is routed and stored as a part of a study and/or other collection of data into a database for future access. Generally, the data will be de-identified from the particular patient, so as to preserve confidentiality and impartially of the data and to comply with applicable privacy laws. For example, the patient's name, social security number, address, and/or other sensitive information are removed from the data, while the patient's physical characteristics, selected treatment plan, and outcome are maintained. In some embodiments, the data is entered into the database(s) by a medical professional as part of the post-treatment analysis. The data related to current patient's outcome creates a feedback loop that provides confirmation of prior information and/or new information from which the medical professionals can modify the treatment plans and/or medical device manufacturers can modify the implants or devices.

In some instances, the patient data, images, models, simulations, and/or other information of the present disclosure are processed, compiled, or otherwise manipulated. In that regard, the methods, systems, and concepts described in the following references are utilized in connection with the patient data, images, models, simulations, and/or other information in some instances: U.S. Pat. No. 5,970,499 filed Apr. 11, 1997 and titled "Method and Apparatus for Producing and Accessing Composite Data"; U.S. Pat. No. 6,009,212 filed Jul. 10, 1996 and titled "Method and Apparatus for Image Registration"; U.S. Pat. No. 6,226,418 filed Nov. 5, 1998 and titled "Rapid Convolution Based Large Deformation Image Matching Via Landmark and Volume Imagery"; U.S. Pat. No. 6,253,210 filed Aug. 25, 1999 and titled "Method and Apparatus for Producing and Accessing Composite Data"; U.S. Pat. No. 6,408,107 filed Nov. 14, 2000 and titled "Rapid Convolution Based Large Deformation Image Matching Via Landmark and Volume Imagery"; U.S. Pat. No. 6,526,415 filed Jun. 11, 2001 and titled "Method and Apparatus for Producing an Accessing Composite Data"; U.S. Pat. No. 6,553,152 filed Apr. 27, 1999 and titled "Method and Apparatus for Image Registration"; U.S. Pat. No. 6,611,630 filed Jun. 7, 1999 and titled "Method and Apparatus for Automatic Shape Characterization"; U.S. Pat. No. 6,633,686 filed Sep. 20, 2000 and titled "Method and Apparatus for Image Registration Using Large Deformation Diffeomorphisms on a Sphere"; U.S. Pat. No. 6,694,057 filed Jan. 27, 2000 and titled "Method and Apparatus for Processing Images with Curves"; U.S. Pat. No. 6,708,184 filed May 4, 2001 and titled "Method and Apparatus for Producing and Accessing Composite Data Using a Device Having a Distributed Communication Controller Interface"; U.S. Pat. No. 6,754,374 filed Dec. 16, 1999 and titled "Method and Apparatus for Processing Images with Regions Representing Target Objects"; each of which is hereby incorporated by reference in its entirety.

Figure 23:
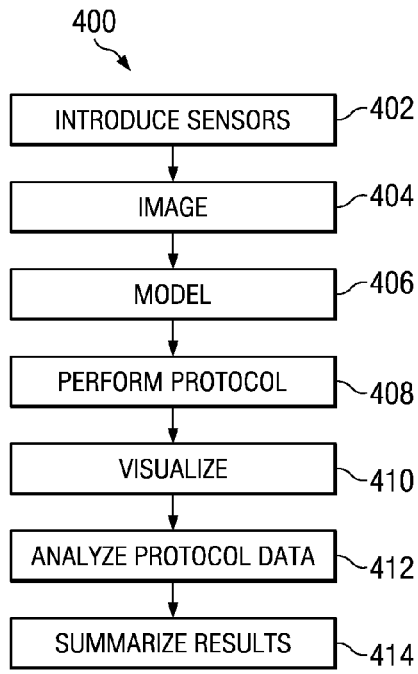
FIG. 23 is a flow chart illustrating a method for visualizing and analyzing anatomical motion according to one embodiment of the present disclosure.

Referring now to FIG. 23, shown therein a method 400 for visualizing and analyzing anatomical motion according to one embodiment of the present disclosure. Generally, the method 400 utilizes sensors, wireless telemetry or other communication means, and 3-D or 2-D reconstructions of the anatomy to visualize and analyze the anatomical motion. As described in greater detail below, the method 400 is for use in patient treatment. For example, in various embodiments the method 400 is used for diagnosing and/or categorizing a patient's medical problems, creating a patient treatment plan (e.g., surgical procedures, physical therapy, chemical therapy (e.g., pharmaceuticals or other drug therapies), and combinations thereof), monitoring the progress of a patient treatment plan, comparing the effectiveness of different treatment plans for patients with similar medical problems, and numerous other medical applications. Further, the method 400 is particularly well suited for use in orthopedic applications. For example, in one particular embodiment the method 400 is used in the analysis and treatment of spinal disorders. As another example, the method 400 is also used in the analysis and treatment of patients likely to receive prosthetic joint replacements (e.g., hip, knee, vertebrae, and ankle) in other embodiments. In such embodiments, the method 400 is configured to provide information useful in determining the appropriate prosthetic implant for a patient (e.g., shape, size, design, material, etc.) and is further configured to monitor the effectiveness of the prosthetic after implantation in some instances.

The method 400 begins at step 402 in which one or more sensors are introduced. In some embodiments, the sensors are accelerometer and/or gyroscopes. In particular, in some embodiments the sensors comprise a micro-accelerometer. In some aspects, the micro-accelerometer is either MEMS-based or piezoelectric-based. MEMS-based micro-accelerometers are preferred in some instances because there is no need for motion to obtain useable data. Generally, the sensors are placed in close proximity to an anatomical structure of interest. In this manner, the sensors are utilized to correlate the position of the anatomical structure based on the motion data obtained from the sensor. In some instances, a plurality of sensors may be utilized adjacent to a single anatomical feature to provide more accurate position data for the anatomical structure and/or provide redundancy. In some instances, position information is extrapolated using secondary systems in the sensor device. For example, in some instances a wireless communications interface used for sending data between the sensors and a processing unit can be used to detect the relative distances between the sensors and the processing unit through ping-response time measurements. The sensors may be implanted into the patient's body adjacent to the anatomical feature of interest, placed on the skin of the patient adjacent to the anatomical feature(s) of interest, and/or placed on clothing of the patient adjacent to the anatomical feature(s). In some embodiments, implantable sensors are preferred. In some instances, sensors are used both inside and outside of the patient's body. Implantable sensors facilitate direct contact with the anatomical feature(s) of interest or at least provide substantially closer placement to the anatomical features than sensors that remain outside the patient's body. In that regard, implantable sensors facilitate the accurate detection of the position of internal anatomical features that cannot be accurately determined with external sensors alone.

In some embodiments, the implantable sensors are configured for engagement with bone. In that regard, the implantable sensors are part of a bone screw or other bone fixation device in some embodiments. In other embodiments, the implantable sensors are secured to the bone via a biocompatible adhesive, a structural fixation device (screw, staple, etc.), combinations thereof, and/or other otherwise secured to the bone. Generally, engaging the implantable sensors with bone provides a fixed orientation between the sensor and the bone, which allows a good correlation between the position of the sensor and the position of the bone. In other embodiments, the sensors are configured for engagement with softer tissues. In such embodiments, the sensors include features to prevent unwanted movement of the sensors relative to the tissue. Where the sensors are implanted inside the body, the sensors are introduced via a guidewire, needle, catheter, tube, and/or other suitable implantation means. Preferably, the sensors are implanted using a minimally invasive procedure and in some instances are implanted percutaneously. In some embodiments, systems and methods may be used as described in U.S. patent application Ser. No. 10/985,108 filed Nov. 10, 2004 and titled "Method and Apparatus for Expert System to Track and Manipulate Patients," herein incorporated by reference in its entirety.

The sensors are utilized for tracking the position of one or more anatomical features. In that regard, one or more sensors are placed adjacent each anatomical feature of interest. In some embodiments the sensors are configured for identifying the location of one or more of the following anatomical features or parts thereof: heels, ankles, knees, hips, iliac crests, sacrum, pelvis, spinal column, spinal column regions, vertebrae, transverse processes, spinal processes, clavicles, and other anatomical features. In one particular embodiment, the sensors are placed on a plurality of vertebrae. As will be described in greater detail below, the relative motion of the sensors placed on each of the plurality of vertebrae are utilized to obtain relative orientation and motion information for the vertebrae. The actual anatomical features for which sensors are located adjacent to depends on numerous factors including physician preference, patient condition, treatment plans, surgical procedures, and other factors. In some embodiments, the anatomical feature(s) of interest may be selected by the treating physician or technician.

After the sensors have been introduced at step 402, the method 400 continues at step 404 in which an imaging protocol is performed. In orthopedic applications, the imaging focuses on the relevant skeletal structures of the patient. Generally speaking, the imaging of step 404 may include x-ray, fluoroscopy, and/or CT scans. X-ray machines may be utilized to obtain snap-shot images of the patient's skeletal structure. Fluoroscopy machines may be utilized to obtain real-time images of the patient's skeletal structure. In some embodiments, the imaging step 404 is utilized to obtain images of the patient's spinal column, pelvis, iliac crest, sacrum, hips, shoulders, clavicles, skull, arms, legs, knees, ankles, feet, and/or combinations thereof. In some embodiments, the imaging protocol is utilized to obtain at least sagittal and frontal images of the patient's anatomy. In some embodiments, the patient simply turns to obtain the desired perspective view for the radiograph. In that regard, the patient may be asked to physically turn herself or himself or, in some embodiments, a moveable platform rotates the patient between the desired positions such that the patient can remain substantially stationary between positions. In some embodiments the imaging step 404 simultaneously obtains the sagittal and frontal images of the patient's anatomy. In addition to the sagittal and frontal views, the other views of the patient's anatomy that would be advantageous to patient analysis are obtained.

After imaging protocol has been performed at step 404, the method 400 continues at step 406 in which a model of the patient's relevant anatomical features is created. Generally, the data from the imaging protocol is utilized to create the model. In one particular embodiment, the data from the imaging protocol is utilized to segment the model into the individual bones of the patient. In that regard, a joint is modeled by the combination of individual bones that come together to form the joint. In some embodiments, the dimensions of the implanted sensor are known and utilized to correlate bone position to the sensor position. Further, the orientation of the sensor to the bone is established by an asymmetry in the structure of the sensor that is identifiable through the imaging protocol. Accordingly, in some embodiments the known dimensions and features of the implanted sensors are utilized in creating the model of the patient's anatomical features. The model is either a 3-D or 2-D representation of the patient's anatomy. In some embodiments, the model is animated to illustrate a motion sequence of the patient's anatomy. The animated model is particular beneficial in the diagnosis and treatment of orthopedic joints. One particular method for modeling the patient's anatomy is to provide or develop a highly accurate model of a generic skeleton, and then map a model of the specific patient derived from an imaging study to the generic skeleton. In some instances this is accomplished through identifying key landmarks on each bone, and then growing or shrinking the original master model according to the measured distances of these landmarks on the patient. Through this method, a useful 3D model of a patient is created that can then undergo kinematics and/or finite element analysis. In some instances, the modeling is performed in a manner similar to that described by Rajamani, K. T.; Joshi, S. C.; Styner, M. A., "Bone model morphing for enhanced surgical visualization," Biomedical Imaging: Nano to Macro, 2004. IEEE International Symposium on, vol., no., pp. 1255-1258 Vol. 2, 15-18 Apr. 2004, hereby incorporated by reference in its entirety.

After creation of the model at step 406, the method 400 continues at step 408 with the performance of a diagnostic protocol. Generally, the diagnostic protocol is performed to measure joint motion and/or relative motion between anatomical features. In a first aspect, the diagnostic protocol utilizes the relative motion between the implanted sensors to monitor joint motion. That is, the movement of each sensor with respect to the other sensors is tracked and utilized to determine the relative motion between the anatomical features associated with each sensor. In a second aspect, the diagnostic protocol utilizes the absolute positions of the sensors to correlate to the motion of the anatomical features. That is, the positions of the sensors are tracked with respect to a reference point (e.g., a signal receiver), which can in turn be utilized to determine the motion of the anatomical features. In some embodiments, the positions of the sensors are monitored using wireless telemetry to measure the distances between each sensor. For example, in some instances each sensor is registered with a signal receiver and the position of the sensor is tracked using wireless telemetry. Based on the communication of the sensor with the signal receiver a time of flight calculation can be made to triangulate the position of the sensor with respect to the signal receiver over time. The positions of each of the sensors can then be compiled to identify the relative motion sequence of the anatomical features with respect to one another. Taken together, the motion of the anatomical features with respect to one another define the joint motion.

In either case, the relative orientations of the sensors are initially determined at a static point or a reference point. In some instances, the relative orientations of the sensors at the static point are determined by the direction of gravity as measured by each of the accelerometer sensors. In other instances, the relative orientations of the sensors are determined by the positions of the sensors obtained from the telemetry communication of the sensors with the signal receiver. Once the relative orientations and/or positions of the sensors have been determined, the patient is moved through a diagnostic protocol comprising a series of movements. During the series of movements the acceleration and/or positional data from the sensors is obtained. The actual series of movements the patient is put through depends upon the specific medical condition of the patient. In some embodiments, the diagnostic protocol comprises having the patient walk on a treadmill. In some instances, a reference point or time=0 point is established. In that regard, the reference point is a starting point for identifying the motion sequence of the patient's anatomical features. Accordingly, in some embodiments the reference point is established based on an image obtained during the imaging step 404.

In some embodiments, an electromagnetic measurement system is utilized to track the positions of the implantable sensors. For example, the electromagnetic measurement system can detect the presence of sensors excitable by an electromagnetic field to determine the position of the anatomical features associated with the sensor. As described above, the sensors may be external or implantable. The electromagnetic measurement system may utilize a computer system to calculate the 3-D position of the anatomical feature(s) based on the position of the sensors. In some embodiments, the electromagnetic measurement system is configured to detect the position of sensors in a fixed volume of space. In that regard, in some embodiments the fixed volume of the electromagnetic measurement system is sufficient to obtain the position of all relevant anatomical features of a patient. In other embodiments, however, the fixed volume may be sufficient to obtain 3-D positions of only some anatomical features of a patient. Where the fixed volume is sufficient to obtain 3-D positions of some, but not all of the patient's anatomical features, a portion of the electromagnetic measure system (e.g., the electromagnetic field generator) may be moveable such that the 3-D positions of the anatomical features of most interest can be obtained. In lieu of or in addition to the electromagnetic measurement system, an infrared system and/or a video system are utilized for determining the 3-D position of the sensors in some embodiments. The video system may be a single camera or multi-camera system. In that regard, a multi-camera video system may take the resulting video triangulate the positions of anatomical features of interest using a computer system. Video system in this context is understood to include still photography in addition to moving video.

After the diagnostic protocol of step 408 has been performed, the method 400 continues at step 410 in which the model of step 406 is updated and/or a new 3-D and/or 2-D animated model of the patient's anatomy is created to visualize the patient's anatomy. Generally, the animated model is based on the data obtained from the imaging of step 404 and the diagnostic protocol of step 408. In some embodiments, the animated model is used to highlight the problem areas and/or times in the patient's anatomical motion sequence. In that regard, the model includes layers of anatomical features that are selectively included or removed. For example, in one embodiment the patient's motion anatomy is grouped into layers according to types of anatomical tissue, such as bones, cartilage, ligaments, tendons, muscles, and/or combinations thereof. The animated model then analyzes motion according to each grouping of anatomical tissue and the interactions therebetween.

In some embodiments, the animated model combines diagnostic tests with the imaging study. For example, in some embodiments the animated model combines muscle monitoring with the imaging study to identify muscle contractions and tensions during a motion sequence or protocol. The muscle monitoring is accomplished through the use of additional sensors in some embodiments. In other embodiments, the muscle monitoring is accomplished through the use of external sensing systems. The results of the muscle monitoring are combined with the other imaging data to provide additional details and/or realism to the animated model. In other embodiments, the animated model utilizes center-of-balance or center-of-gravity data for the patient obtained during the motion sequence or diagnostic protocol. Muscle monitoring and center-of-balance data are merely examples of the types of additional data that may be combined with the imaging data in forming the animated model. Other types of the patient data may also be utilized. In that regard, in some embodiments the treating physician or medical personnel selects the types of patient data to be used in formulating the animated model.

The method 400 continues with step 412 in which the data obtained from the diagnostic protocol of step 408 is analyzed. In some embodiments, the animated model includes features to allow medical personnel and/or a computer system to analyze the patient's motion sequence. In that regard, in some embodiments the animated model includes a stress grid overlay that indicates potential areas of increased stress or strain on the patient's anatomy, such increased muscle activity; overstretching of muscles, ligaments, and/or tendons; friction between bones; and/or other areas of stress/strain. In some embodiments the model allows for zooming, panning, or otherwise changing the orientation of the view of the patient's anatomy. A user adjusts the orientation to better observe or isolate a potential problem area. Similarly, the animated model allows a user to pause, rewind, slow down, and/or speed up simulation of a motion sequence to better observe a potential problem. Further, the animated model allows 3-D and/or 2D tracking of specific anatomical features through the motion sequences. In some embodiments, the animated model highlights potential problem areas automatically based on a comparison to a standardized model. For example, the system may identify anatomical features with a motion sequence outside of a predetermined range. In that regard, the standardized model and/or predetermined range of normal motion are at least partially defined by a general patient population. In some embodiments, the treating physician or medical personnel highlights potential problem areas based on their observations of the patient's motion sequence. In some embodiments, the problem areas are identified by a computer system and/or medical personnel by recognizing an abnormal motion pattern(s). In some instances, the abnormal motion patterns are grouped into motion signatures that are indicative of a medical condition. Each of the motion signatures, in turn, are associated with appropriate medical treatment options for correcting the medical condition(s) associated with the motion signature. The method 400 concludes at step 414 by summarizing the results of the analysis of step 412.

Figure 24:
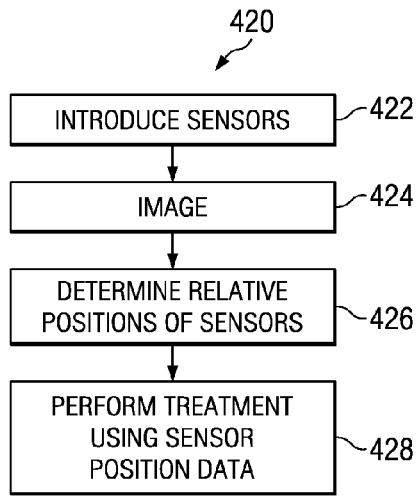
FIG. 24 is a flow chart illustrating a method for using implantable sensors in an image-guided treatment according to one embodiment of the present disclosure.

Referring now to FIG. 24, shown therein a method 420 for using implantable sensors in an image-guided treatment according to one embodiment of the present disclosure. Generally, the method 420 utilizes implantable sensors as fiducial markers for use during the image-guided procedure. In this context a fiducial marker provides a reference point for orientation of implants and surgical instruments during the image-guided treatment. In some instances, the sensors are configured to be affixed to portions of a patient's body, especially the bony anatomy, and are configured to show up in an x-ray or other imaging so that succeeding scans or pictures may be registered or correlated to one another. In accordance with the present disclosure, the implantable sensors are capable of being mapped in three-dimensional format relative to one another as described above. Generally, the relative motion of the sensors between one another may be utilized to track the motion of the anatomical features of the patient and/or the positions of the sensors relative to a reference point or receiver may be utilized to track the motion of the anatomical features. The method 420 is particularly well suited for use in orthopedic surgical procedures, such as spinal surgeries, joint replacements, and other orthopedic procedures. In that regard, the method 420 is configured to provide positional information useful in ensuring the appropriate placement and orientation of any implants and/or fixation devices during the surgical procedure. Further, the implantable sensors are used to monitor the placement and orientations of the implant and/or fixation devices after implantation in some instances.

The method 420 begins at step 422 in which one or more sensors are introduced. In some embodiments, the sensors are accelerometer and/or gyroscopes. In particular, in some embodiments the sensors comprise a micro-accelerometer. Generally, the sensors are placed in close proximity to an anatomical structure of interest. In this manner, the sensors are utilized to correlate the position of the anatomical structure based on the position of the sensor. In some instances, a plurality of sensors may be utilized adjacent to a single anatomical feature to provide more accurate position data for the anatomical structure. The sensors may be implanted into the patient's body adjacent to the anatomical feature of interest and/or placed on the skin of the patient adjacent to the anatomical feature(s) of interest. For most procedures, implantable sensors are preferred. In some instances, sensors are used both inside and outside of the patient's body. Implantable sensors facilitate direct contact with the anatomical feature(s) of interest or at least provide substantially closer placement to the anatomical features than sensors that remain outside the patient's body. In that regard, implantable sensors facilitate the accurate detection of the position of internal anatomical features that cannot be accurately determined with external sensors alone.

Figure 25:
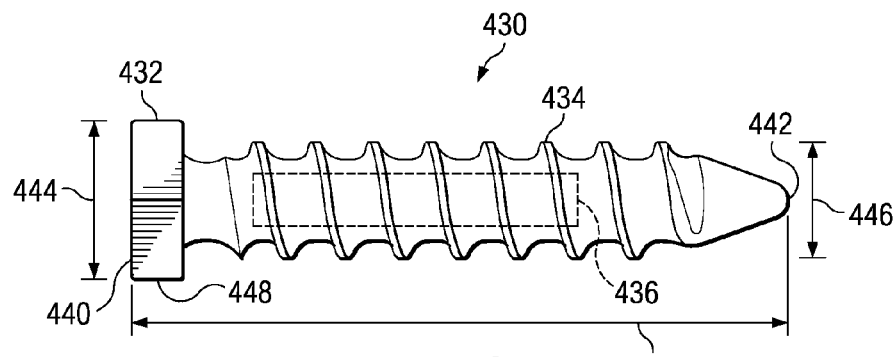
FIG. 25 is a diagrammatic partial cross-sectional side view of a bone screw in accordance with one embodiment of the present disclosure.
Figure 26:
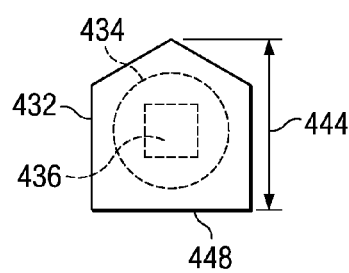
FIG. 26 is a diagrammatic top view of the bone screw of FIG. 25.

In some embodiments, the implantable sensors are configured for engagement with bone. In that regard, the sensors may be secured to the surface of a bone (e.g., using an epoxy or other biocompatible adhesive), inserted into a void in the bone, press-fit into the bone, cemented into the bone, and/or imbedded in a housing or device that is secured to the bone. In some embodiments, the implantable sensors are part of a bone screw or other bone fixation device. For example, referring more particularly to FIGS. 25 and 26, shown therein is a bone screw 430 in accordance with one embodiment of the present disclosure. The bone screw 430 comprises a head portion 432 and a body portion 434. In the current embodiment, the body portion 434 is threaded such that it may be screwed into a bone of a patient. In other embodiments, the bone screw is secured to the bone via a biocompatible adhesive, surface coatings or treatments (e.g. chemical etching, bead-blasting, sanding, grinding, serrating, diamond-cutting, coating with a biocompatible and osteoconductive material (such as hydroxyapatite (HA), tricalcium phosphate (TCP), or calcium carbonate), or coating with osteoinductive materials (such as proteins from the transforming growth factor (TGF) beta superfamily or bone-morphogenic proteins, such as BMP2 or BMP7)), other structural fixation devices (e.g., staple, nail, etc.), and/or combinations thereof. Further, in some instances the bone screw incorporates one or more biologic materials. As shown, the body portion 434 also contains a sensor housing 436 therein. The sensor housing 436 contains all of the electronics and associated elements of the sensor. Depending on the type of sensor utilized the housing 436 contain different elements. While the sensor housing 436 is shown as being positioned substantially centrally within the body portion 436, in other embodiments the sensor is positioned off-center, adjacent an end or surface of the body, and/or within the head portion of the bone screw 430. The illustrated position of the housing 436 is for exemplary purposes only and should not be considered limiting.

The bone screw 430 can be utilized to create a model of the patient's anatomy. In that regard, in some embodiments the bone screw 430 is identified in imaging studies in relation to anatomical features of the patient. In some embodiments, the size of the bone screw 430 is well defined such that the relative size of the bone screw to the anatomical features is utilized in creating the model of the anatomical features. To that end, the bone screw 430 has a length 438 extending between a proximal end 440 and a distal end 442. Further, the head portion 432 of the bone screw has a height or thickness 444 extending between its uppermost portion and its lowermost portion. The body portion 434 of the bone screw 430 has a height or thickness 446 as measured from the outer portion of the bone screw threads. In other embodiments, such as a nail embodiment, the body portion 434 has a substantially constant height 446. In the current embodiment, the height 444 of the head portion 432 is larger than the height 446 of the body portion 434. In other embodiments, the height of the head portion is substantially equal to or less than the height of the body portion.

Figure 27:
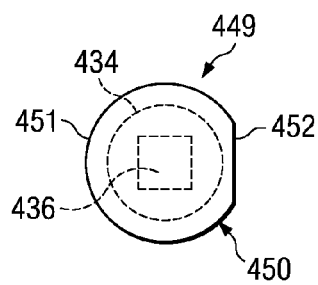
FIG. 27 is a diagrammatic top view of a bone screw similar to that shown in FIG. 26 but illustrating an alternative embodiment of the present disclosure.

The head portion 432 is configured for engagement with a driving tool such that the driving tool may be utilized to secure the bone screw 430 into a bone. In the current embodiment, a majority of the head portion 432 is configured for engagement with a hex-shaped driver. Accordingly, the bone screw 430 may be secured into the bone by rotatingly driving the body portion 434 into the bone with a hex-shaped driver (not shown). As best seen in FIG. 26, the head portion 432 also includes a portion 448 that provides the bone screw 430 with an asymmetric profile. That is, the portion 448 provides the bone screw 430 with a distinguishing feature such that the orientation of the bone screw can be determined when viewed in a image. Accordingly, the bone screw is not asymmetric in all embodiments. Rather, in some embodiments the bone screw comprises a substantially symmetrical profile, but includes one or more features that allow the orientation of the bone screw to be determined. Referring to FIG. 27, shown therein is a bone screw 449 according to another aspect of the present invention. The bone screw 449 is substantially similar to bone screw 430 in many respects, however, the bone screw 449 includes a head portion 450 illustrating an alternate profile. In particular, the head portion 450 includes a majority portion 451 having a substantially circular profile and a minority portion 452 having a substantially planar profile. Accordingly, the orientation of the head portion 450 and, in turn, the bone screw 449 is determined by the position of the minority portion 452 relative to the majority portion 451.

Generally, engaging the implantable sensors with bone provides a fixed orientation between the sensor and the bone, which allows a good correlation between the position of the sensor and the position of the bone. In other embodiments, the sensors are configured for engagement with softer tissues. In such embodiments, the sensors include features to prevent unwanted movement of the sensors relative to the tissue. Where the sensors are implanted—temporarily or permanently—inside the body, the sensors are introduced via a guidewire, needle, catheter, tube, and/or other suitable implantation means. Preferably, the sensors are implanted using a minimally invasive procedure and in some instances are implanted percutaneously.

One or more sensors are placed adjacent to or within each anatomical feature of interest. In some embodiments the sensors are positioned adjacent to one or more of the following anatomical features or parts thereof: heels, ankles, knees, hips, iliac crests, sacrum, pelvis, spinal column, spinal column regions, vertebrae, transverse processes, spinal processes, clavicles, and other anatomical features. In one particular embodiment, the sensors are placed on a portion of a plurality of vertebrae. In one specific embodiment, the sensors are placed on the spinous processes of at least two adjacent vertebrae. The actual anatomical features for which sensors are located adjacent to depends on numerous factors including physician preference, patient condition, treatment plans, surgical procedures, and other factors. In some embodiments, the anatomical feature(s) of interest are selected by the treating physician or technician.

After the sensors have been introduced at step 422, the method 420 continues at step 424 in which an imaging technique is utilized to obtain an image of the patient with the sensors attached to the pertinent anatomical features. In orthopedic applications, the imaging focuses on the relevant skeletal structures of the patient to which the bone screw 430 or other sensor has been attached. Generally speaking, the imaging of step 424 may include x-ray, fluoroscopy, and/or CT scans. X-ray machines may be utilized to obtain snap-shot images of the patient's skeletal structure. Fluoroscopy machines may be utilized to obtain real-time images of the patient's skeletal structure. In some embodiments, the imaging step 424 is utilized to obtain images of the patient's spinal column, pelvis, iliac crest, sacrum, hips, shoulders, clavicles, skull, arms, legs, knees, ankles, feet, and/or combinations thereof. In some embodiments, the imaging technique is utilized to obtain at least sagittal and frontal images of the patient's anatomy. In addition to the sagittal and frontal views, other views of the patient's anatomy that are advantageous to patient analysis are obtained in some instances.

The method 420 also includes step 426 in which the relative positions of the sensors is determined. In that regard, the relative positions of the sensors are determined with respect to the anatomical features of the patient and/or the other sensors. Generally, the implanted sensors include features that allow them to be visualized on the images obtained using the imaging technique. In some instances, the sensors or the housing of the sensors (such as bone screw 430) are substantially radiopaque so as to be visible on x-ray and/or fluoroscopy imaging. In that regard, in some embodiments the sensors or the housing of the sensors (such as bone screw 430) include features, such as asymmetric profiles or otherwise, that allow the orientation of the sensor/housing relative to the anatomical features to be determined from the images.

From the images a 3-D or 2-D model of the patient's anatomy can be created. In some embodiments, the model is animated to illustrate and/or track a motion sequence of the patient's anatomy. In some embodiments, the model can be updated in approximately real-time based on the position of the sensors and/or accelerometer information provided by the sensors to provide the surgeon or other medical personnel with the relative locations of the anatomical features with respect to one another. In some embodiments, the model utilizes the relative motion between the implanted sensors to monitor and update anatomical positioning. The movement of each sensor with respect to the other sensors is tracked and utilized to determine the relative motion between the anatomical features associated with each sensor. The relative positions of the anatomical features is determined therefrom. In some embodiments, the model utilizes the absolute positions of the sensors to correlate to the position of the anatomical features. That is, the positions of the sensors are tracked with respect to one or more reference points (e.g., a signal receivers), which can in turn be utilized to determine the position of the anatomical features. In some embodiments, the positions of the sensors are monitored using wireless telemetry to measure the distances between each sensor. For example, in some instances each sensor is registered with the one or more signal receivers and the position of the sensor is tracked using wireless telemetry. Based on the communication of the sensor with the signal receiver a time of flight calculation can be made to triangulate the position of the sensor with respect to the signal receiver. Triangulation can be done either by lateration (i.e., determining distance measurements to the sensors from the receivers) or by angulation (i.e., determining angles between the sensors and the receivers and computing the location of the sensors based on the fixed dimensions between the receivers).

The method 420 continues with step 428 in which a treatment is performed utilizing positional data provided by the sensors. In that regard, a detailed treatment plan may have been established and modeled as described above with respect to other embodiments. Accordingly, the implanted sensors and resulting data may be utilized in step 428 to ensure compliance with the planned treatment and/or ensure that the treatment is performed within a predetermined error field.

Figure 28:
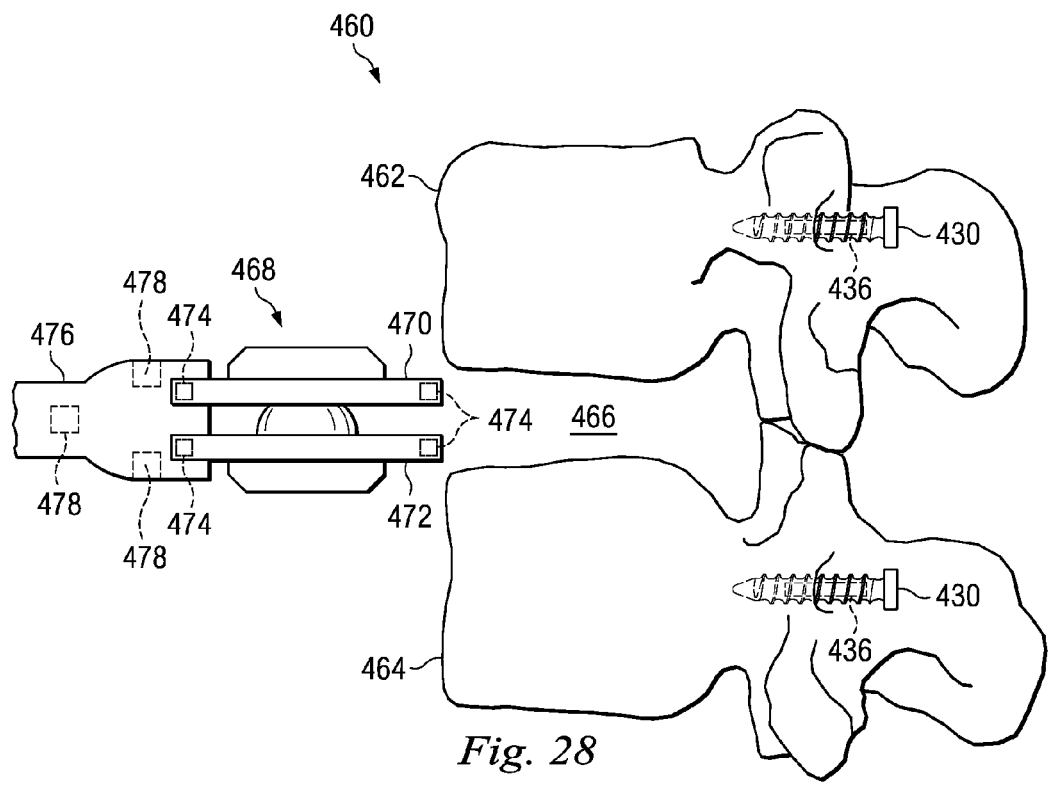
FIG. 28 is a diagrammatic side view of a system according to another embodiment of the present disclosure for using sensors in an image-guided treatment.

Referring more particularly to FIG. 28, shown therein is a system 460 illustrating step 428 of method 420 according to one particular embodiment of the present disclosure. In that regard, the system 460 shows an upper vertebra 462, a lower vertebra 464, and an intervertebral disc space 466. A bone screw 430, including sensor 436 therein, has been secured to each of the upper and lower vertebrae 462, 464. In the illustrated embodiment, the natural disc has been removed such that the intervertebral disc space 466 and the vertebrae 462, 464 are configured to receive an artificial disc prosthesis 468. In the illustrated embodiment, the prosthesis 468 comprises an upper portion 470 configured for engaging with the upper vertebra 462 and a lower portion 472 configured for engaging with the lower vertebra 464. The upper portion 470 articulatingly engages the lower portion 472. Each of the upper and lower portions 470, 472 include sensors 474 therein. In the illustrated embodiment, the sensors are positioned adjacent the anterior and posterior portions of the prosthesis 468. These positions are for exemplary purposes only and should not be considered limiting. In particular, it is contemplated that one or more sensors 474 may be positioned within and/or attached to the disc prosthesis 468. The one or more sensors 474 are utilized to track the placement of the disc prosthesis within the intervertebral disc space as it is implanted and, in some embodiments, after implantation. In that regard, the position of the sensors 474 are compared to the positions of the sensors 436 to determine the relative position of the prosthesis 468 within the disc space 466 in some embodiments. In that regard, in some embodiments the sensors 474 communicate directly with the sensors 436 to determine relative position of the prosthesis 468. In other embodiments, a centralized receiver or imaging device determines the position of the sensors 436 and 474 to determine the relative position of the prosthesis 468. Where the prosthesis 468 includes one or more sensors 436 the tool utilized for inserting the prosthesis need not necessarily have sensors because the position of the prosthesis can be determined from the sensors therein. However, in the illustrated embodiment the system 460 includes an insertion tool 476 having a plurality of sensors 478.

Similar to the sensors 474 within the prosthesis 468, the sensors 478 of the insertion tool 476 are utilized to track the placement of the disc prosthesis within the intervertebral disc space 466 as it is implanted. To ensure proper orientation between the insertion tool 476 and the prosthesis 468 to allow a correlation between the position of the tool and the position of the prosthesis, the prosthesis 468 includes apertures (not shown) for receiving an engagement portion of the insertion tool in some embodiments. The position of the sensors 478 are compared to the positions of the sensors 436 to determine the relative position of the prosthesis 468 within the disc space 466 in some embodiments. In that regard, in some embodiments the sensors 478 communicate directly with the sensors 436 to determine relative position of the prosthesis 468. In other embodiments, a centralized receiver or imaging device determines the position of the sensors 436 and 478 to determine the relative position of the prosthesis 468. In some embodiments, both sets of sensors 474 and 478 within the prosthesis and the insertion tool 476 are utilized to monitor positioning of the prosthesis 468.

In some embodiments, the model of the patient's anatomical features is updated in approximately real-time to illustrate the position of the prosthesis 468 and/or insertion tool 476 relative to the vertebrae 462, 464 and the sensors 436. In some embodiments, an image guided surgery system utilizes the positional data from the sensors 436, 474, and/or 478 to ensure proper placement and orientation of the prosthesis within the disc space 466. In that regard, in some embodiments the insertion tool 476 is part of the image guided surgery system. Further, in some embodiments the image guided surgery system is communication with the model and/or the model is a component of the image guided surgery system such that a visualization of the prosthesis and associated anatomical features of the patient is provided to confirm proper placement of the prosthesis within the disc space. In some embodiments, the image guided surgery system utilizes the model in monitoring the placement of the prosthesis. It is understood that the procedure described above is exemplary and that numerous other treatment procedures may be performed using the concepts described.

Figure 29:
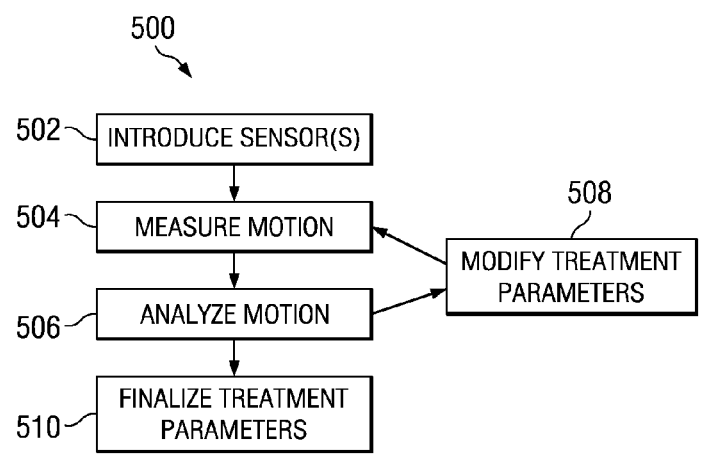
FIG. 29 is flow chart illustrating a method for selecting and modifying implant parameters using implanted sensors according to one embodiment of the present disclosure

Referring now to FIG. 29, shown therein is a method 500 for selecting and modifying implant parameters using implanted sensors according to one embodiment of the present disclosure. The method 500 begins with step 502 in which one or more sensors are introduced. In that regard, the particular type of sensors that are introduced will depend on the patient anatomy to be monitored. In some embodiments, the pertinent anatomical features of the patient comprise a joint. In such embodiments, accelerometers and/or gyroscopes are utilized as the sensors. Use of the accelerometers and/or gyroscopes allows the sensors to track the motion of the joint and thereby monitor the performance of the joint and any implants or other medical treatments associated therewith. Generally, the sensors are placed in close proximity to an anatomical structure of interest. In that regard, in some instances the sensors are placed on an implant, prosthesis, fixation device, or other device that is part of a treatment plan. In other instances, the sensors are stand alone units placed adjacent to the anatomical structure of interest and any associated devices if present.

In this manner, the sensors are utilized to correlate the position of the anatomical structure based on the position of the sensor. In some instances, a plurality of sensors are utilized adjacent to a single anatomical feature to provide more accurate position data for the anatomical structure. Depending on the anatomical features of interest, the sensors may be implanted into the patient's body adjacent to the anatomical feature of interest, placed on the skin of the patient adjacent to the anatomical feature(s) of interest, and/or placed on clothing of the patient adjacent to the anatomical feature(s). In some embodiments, implantable sensors are preferred. In some instances, sensors are used both inside and outside of the patient's body. Implantable sensors facilitate direct contact with the anatomical feature(s) of interest or at least provide substantially closer placement to the anatomical features than sensors that remain outside the patient's body. In that regard, implantable sensors facilitate the accurate detection of the position of internal anatomical features that cannot be accurately determined with external sensors alone. The remaining description of the present method 500 will be described with respect to implanted sensors, however, no limitation is intended thereby.

In some embodiments, the implantable sensors are configured for engagement with bone. In that regard, the implantable sensors are part of a bone screw or other bone fixation device in some embodiments. In other embodiments, the implantable sensors are secured to the bone via a biocompatible adhesive or epoxy, a structural fixation device (screw, staple, etc.), combinations thereof, and/or other otherwise secured to the bone. Generally, engaging the implantable sensors with bone provides a fixed orientation between the sensor and the bone, which allows a good correlation between the position of the sensor and the position of the bone. In other embodiments, the sensors are configured for engagement with softer tissues. In such embodiments, the sensors include features to prevent unwanted movement of the sensors relative to the tissue. The sensors are introduced via a guidewire, needle, catheter, tube, and/or other suitable implantation means. Preferably, the sensors are implanted using a minimally invasive procedure and in some instances are implanted percutaneously. In other embodiments, the sensors are implanted as part of a larger surgical procedure and, therefore, are implanted through non-minimally invasive means.

The sensors are utilized for tracking the position of one or more anatomical features. In that regard, one or more sensors are placed adjacent each anatomical feature of interest. In some embodiments the sensors are configured for identifying the location and tracking the motion of one or more of the following anatomical features or parts thereof: heels, ankles, knees, hips, iliac crests, sacrum, pelvis, spinal column, spinal column regions, vertebrae, transverse processes, spinal processes, clavicles, and other anatomical features. In one particular embodiment, the sensors are placed on a plurality of vertebrae along the spine. The relative motion of the sensors placed on each of the plurality of vertebrae are utilized to obtain relative orientation and motion information for the sensors, which in turn can be extrapolated to the vertebrae. The actual anatomical features for which sensors are located adjacent to depends on numerous factors including physician preference, patient condition, treatment plans, surgical procedures, and other factors. In some embodiments, the anatomical feature(s) of interest are selected by the treating physician or technician.

After the sensors have been introduced at step 502, the method 500 continues at step 504 in which the motion profile of the anatomical features is tracked or measured. In some embodiments, the motion profile is tracked by creating a model of the patient's anatomy and simulating the patient's motion profile based on the sensor data. In that regard, an imaging step is performed in some embodiments as part of creating the model. In orthopedic applications, the imaging focuses on the relevant skeletal structures of the patient, which are typically the anatomical features of interest as well. Generally speaking, the imaging may include x-ray, fluoroscopy, and/or CT scans. X-ray machines may be utilized to obtain snap-shot images of the patient's skeletal structure. Fluoroscopy machines may be utilized to obtain real-time images of the patient's skeletal structure, which may be beneficial in correlating the model to the motion profile in some instances.

Generally, the data from the imaging protocol is utilized to create the model. In one particular embodiment, the data from the imaging protocol is utilized to segment the model into the individual anatomical features of the patient. In that regard, a motion joint is modeled by the combination of individual bones that come together to form the joint. In some embodiments, the dimensions of the implanted sensor are known and utilized to correlate bone position to the sensor position. Further, the orientation of the sensor to the bone is established by an asymmetry in the structure of the sensor that is identifiable through the imaging protocol. Accordingly, in some embodiments the known dimensions and features of the implanted sensors are utilized in creating the model of the patient's anatomical features. The model is either a 3-D or 2-D representation of the patient's anatomy. In some embodiments, the model is animated to illustrate the motion profile of the patient's anatomy. In other embodiments, the model is simply a statistical representation of the patient's anatomy and does not provide a visualization. In that regard, a computer system is utilized to analyze the patient's motion sequence and associated data to provide suggested implant parameters and modifications thereto.

In some embodiments, the motion profile of the patient's anatomical features is determined by putting the patient through a diagnostic protocol. In that regard, the diagnostic protocol is a series of movements that the patient is put through that utilizes the anatomical features of interest. In some embodiments, the diagnostic protocol is performed to measure joint motion and/or relative motion between the anatomical features. Accordingly, the diagnostic protocol often comprises a natural movement such as walking, sitting, standing, lying down, or other common movements. However, in other embodiments the diagnostic protocol comprises a specific series of movements that include at least some movements that are not performed on a regular basis. The precise movements or structure of the diagnostic protocol depends on the anatomical features of interest and/or the treating physician's preference.

The implanted sensors are utilized to track the motion profile of the patient's anatomy through the diagnostic protocol. In some embodiments, the relative motion between the implanted sensors are utilized to monitor the patient's motion profile. That is, the movement of each sensor with respect to the other sensors is tracked and utilized to determine the relative motion between the anatomical features associated with each sensor. In some embodiments, the absolute positions of the sensors are tracked and correlated to the motion of the anatomical features. That is, the positions of the sensors are tracked with respect to a reference point(s) (e.g., signal receiver(s)), which can in turn be utilized to determine the motion of the anatomical features. In some embodiments, the positions of the sensors are monitored using wireless telemetry to measure the distances between each sensor. For example, in some instances each sensor is registered with one or more signal receivers and the position of the sensor is tracked using wireless telemetry. Based on the communication of the sensor with the signal receiver a time of flight calculation can be made to triangulate the position of the sensor with respect to the signal receivers over time. The positions of each of the sensors can then be compiled to identify the relative motion sequence of the anatomical features with respect to one another. Taken together, the motion sequence of the anatomical features of interest is established.

In other embodiments, an electromagnetic measurement system is utilized to track the positions of the implantable sensors during the diagnostic protocol. For example, the electromagnetic measurement system can detect the presence of sensors excitable by an electromagnetic field to determine the position of the anatomical features associated with the sensor. The electromagnetic measurement system utilizes a computer system to calculate the 3-D position of the anatomical feature(s) based on the position of the sensors. In some embodiments, the electromagnetic measurement system is configured to detect the position of sensors in a fixed volume of space. In that regard, in some embodiments the fixed volume of the electromagnetic measurement system is sufficient to obtain the position of all relevant anatomical features of a patient. In other embodiments, however, the fixed volume may be sufficient to obtain 3-D positions of only some anatomical features of a patient. Where the fixed volume is sufficient to obtain 3-D positions of some, but not all of the patient's anatomical features, a portion of the electromagnetic measure system is moveable such that the 3-D positions of all the anatomical features of most interest can be obtained.

In some instances, the sensor systems of the present disclosure are self-calibrating. In that regard, the relative orientation and/or position of the sensors is determined by the sensors and associated components without need of manual input from a user or medical personnel. For example, in one embodiment, the implantable sensors interface with a software suite for tracking the positioning of the sensors. Each of the sensors provides an initial coordinate position. In some instances the initial coordinate position will be an arbitrary coordinate. In other instances, the initial coordinate position will be relative to a known point of reference (e.g., a main sensor, a reference point in the room, an anatomical reference point of the patient, or otherwise). Based on the initial coordinate position the software suite will reset or zero out the location of each of the sensors to this starting point. Accordingly, subsequent movements can be compared to this initial starting position.

After the motion profile of the anatomical features has been tracked at step 504, the method 500 continues at step 506 in which the motion profile is analyzed. In some embodiments, the motion profile is analyzed by updating the model and/or creating a model to simulate the detected motion profile. As described above the model is a 3-D and/or 2-D animated model of the patient's anatomy for visualizing the patient's anatomy in some instances. In other instances, the model is simply a numerical or statistical representation of the patient's motion profile that is utilized by a computer system to analyze the patient's anatomical motion profile. In some embodiments, the animated model is used to highlight the problem areas and/or times in the patient's anatomical motion sequence. In that regard, the model includes layers of anatomical features that are selectively included or removed. For example, in one embodiment the patient's motion anatomy is grouped into layers according to types of anatomical tissue, such as bones, cartilage, ligaments, tendons, muscles, and/or combinations thereof. The animated model then simulates the motion according to each grouping of anatomical tissue and the interactions therebetween.

The motion sequence of the patient is analyzed by a computer system and/or medical personnel. In some embodiments, the model itself includes features to allow medical personnel and/or a computer system to analyze the patient's motion sequence. In other embodiments, a separate software suite or program is utilized to analyze the patient's motion sequence. In that regard, in some embodiments the model includes a stress grid overlay that indicates potential areas of increased stress or strain on the patient's anatomy, such increased muscle activity; overstretching of muscles, ligaments, and/or tendons; friction between bones; and/or other areas of stress/strain. In some embodiments the model allows for zooming, panning, or otherwise changing the orientation of the view of the patient's anatomy. A user adjusts the orientation to better observe or isolate potential problem areas. Similarly, the animated model allows a user to pause, rewind, slow down, and/or speed up simulation of a motion sequence to better observe a potential problem. Further, the model allows 3-D and/or 2D tracking of specific anatomical features through the motion sequences. In some embodiments, the animated model highlights potential problem areas automatically based on a comparison to a standardized model. For example, the system identifies anatomical features with a motion sequence outside of a predetermined range in some instances. In that regard, the standardized model and/or predetermined range of normal motion are at least partially defined by a general patient population.

In some embodiments, the treating physician or medical personnel highlights potential problem areas based on their observations of the patient's motion sequence. In some embodiments, the problem areas are identified by a computer system and/or medical personnel by recognizing an abnormal motion pattern(s). In some instances, the abnormal motion patterns are grouped into motion signatures that are indicative of a specific type or grouping of medical conditions. Each of the motion signatures, in turn, is associated with appropriate medical treatment options for correcting the medical condition(s) associated with the motion signature.

Based on the analysis of the patient's motion profile at step 506, the method 500 continues at step 508 in which the treatment parameters are modified or defined in an effort to correct any problems in the motion profile. In some embodiments, the treatment parameters comprise the placement, orientation, stiffness, and/or other aspects of an implant. In that regard, in some embodiments the diagnostic protocol is performed during the surgical procedure such that the implant parameters are modified without need for a subsequent medical procedure. For example, in one embodiment the method 500 is utilized to balance a knee arthroplasty. In other embodiments, the diagnostic protocol is performed post-surgery in an effort to maintain and/or improve the effectiveness of the treatment. In that regard, when modifications to the implant parameters are suggested, a revision surgery may be required. However, in some embodiments, the implant includes features that allow non-invasive adjustment of the implant. For example, in some embodiments the implant includes one or more actuators to adjust the position of the implant relative to a fixation device. In other embodiments, the implant includes one or more actuators to adjust the relative stiffness of the implant. In some embodiments, the implanted sensors are utilized with a dynamic fixation system such as that described in U.S. patent application Ser. No. 11/356,687 filed Feb. 17, 2006 and titled "Sensor and Method for Spinal Monitoring," herein incorporated by reference in its entirety. In that regard, in such embodiments the dynamic actuators that control the dampening force of the implant are adjusted based on the parameters as indicated by the feedback of the sensors. The sensors are utilized to adjust other adjustable implants. In other embodiments, the treatment plan does not include an implant and, therefore, the modified parameters are not related to the implant.

After the treatment parameters have been modified and/or defined in step 508, the method 500 returns to step 504 where the motion profile is again monitored and then analyzed at step 506. If the analysis again detects problems in the motion profile, then the method returns to step 508 for additional modification of the treatment parameters. Accordingly, steps 504, 506, and 508 are iterated until a satisfactory motion profile is established with selected the treatment parameters. When the treatment parameters have been defined to achieve the desired motion profile, then the method 500 concludes with step 510 in which the treatment parameters are finalized. The finalized treatment parameters are then implemented. In some embodiments, steps 504, 506, and 508 are repeated at various intervals after an initial treatment to maintain the desired motion profile of the patient's anatomy.

Figure 30:
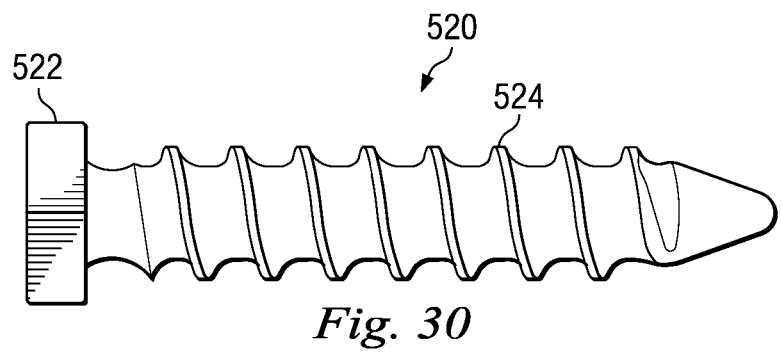
FIG. 30 is a diagrammatic side view of a bone anchor having a plurality of sensors therein according to one embodiment of the present disclosure.
Figure 31:
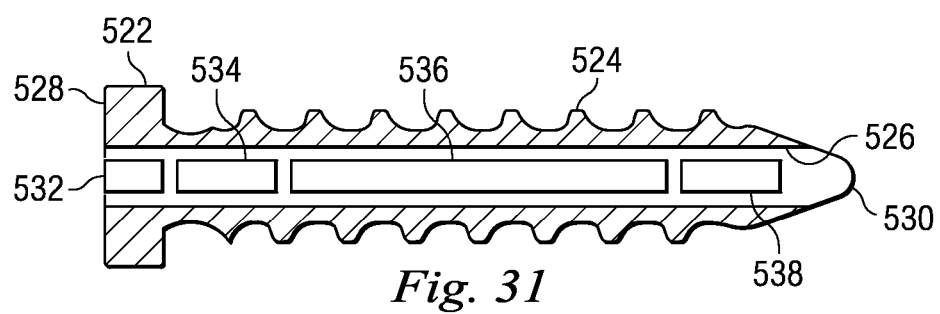
FIG. 31 is a diagrammatic side cross-sectional view of the bone anchor of FIG. 31.

In some embodiments, an implant, prosthesis, fixation element, or other device is instrumented with a plurality of sensing elements to monitor various conditions within a patient. For example, referring more specifically to FIGS. 30 and 31 shown therein is a device 520 according to one aspect of the present disclosure. In the illustrated embodiment, the device 520 comprises a bone anchor or screw configured for engagement with a bony structure of a patient. This illustrated embodiment is merely for exemplary purposes and numerous other types of implants may be similarly fitted with multiple sensors in other embodiments. Generally, the device 520 includes a head portion 522 and a body portion 524. The head portion 522 is configured for engagement with an insertion instrument and, in some embodiments, has a substantially hex-shaped profiled for mating with a hex-shaped driver. In other embodiments, the head portion 522 has other profiles and/or includes recessed portions for engaging with an insertion instrument or driver. The body portion 524 comprises a series of threads for engaging with a bone. The device 520 also includes a opening 526 for housing the sensors extending along its length from a proximal portion 528 to a distal portion 530. In other embodiments, the opening 526 may extend along only a portion of the device 520. For example, in some embodiments the opening is completely contained within the body portion 524 of the device 520. In some embodiments, the device does not include a single opening for housing the sensors, but contains multiple openings for housing the sensors. In some embodiments, the sensors are positioned on the outer surfaces of the device. In some instances an implant is instrumented or fitted with various sensors capable of detecting physical parameters.

A plurality of sensors are positioned within the opening 526. In the illustrated embodiment, a chemical sensor 532, a multi-purpose sensor 534, an accelerometer 536, and a pressure sensor 538 are included within the opening 526. In the current embodiment, if the device 520 was secured to a vertebra the sensors 532, 534, 536, and 538 could be utilized to monitor vertebral motion, load/stress, and/or the existence or quantity of particular proteins adjacent to the site. In that regard, the position, order, or orientation of the sensors with respect to the device 520 may also affect the parameters that are monitored. For example, in some embodiments the pressure sensor is positioned substantially in the head portion 522 of the device. In such embodiments, the pressure sensor is utilized to monitor the patient's heart rate, swelling, and/or other pressure related parameters external to the vertebral joint. Accordingly, the placement and orientation of the sensors relative to one another, the device, and/or anatomical features is selected based on the parameters to be monitored.

Generally, the sensors 532, 534, 536, and 538 are selected from sensors that are able to monitor various physical parameters associated with the patient's anatomical features and/or treatment device, such as pressure, linear displacement, angular displacement, torque, velocity, acceleration, temperature, or pH. In some instances the sensor may be a multi-purpose sensor in that it can be programmed or modified to monitor various parameters. A pressure sensor may, for example, use Wheatstone bridge based strain gauge technology. Alternative pressure sensors may include inductive or capacitive measurement systems. A linear displacement sensor may, for example, use linear variable differential transformer (LVDT) technology to measure linear displacements. Likewise, an angular displacement may, for example, use rotational variable differential transformer (RVDT) technology to measure angular displacement. An acceleration sensor may, for example, include an accelerometer. It is understood that multiple sensors of various types may be used in a single implant to measure different physical parameters. The particular types of sensors to be included within the device 520 depends on the selected treatment, the anatomical feature(s) being treated, physician preference, and/or other factors. In some instances, the device is fully assembled with a predetermined collection of sensors pre-operatively. In other instances, the device is modular such that sensors having the desired parameters are selected from a kit comprised of a plurality of sensors and are inserted into the device pre-operatively or intra-operatively.

In some embodiments, the sensors are utilized to measure anatomical and/or physiological data that is then transferred externally. Accordingly, in embodiments where multiple sensors are utilized it can be necessary to distinguish between the various sensors. In one embodiment, the communication frequencies of the sensors are differentiated to decrease airwave clutter and/or prevent data from being mixed up. In some embodiments, the sensors are coded to automatically establish sensor-to-sensor relationships. Accordingly, a network of sensors can be created by the sensor-to-sensor relationships. The sensor-to-sensor communications are utilized to increase efficiency and/or improve processing times in some instances. In some embodiments each sensor includes a unique identification that is associated with it. In some embodiments, each sensor is assigned a unique serial number or identification number. The serial number or identification number is then transferred along to the external device with any data. Accordingly, any data received from the sensors is associated with a particular sensor. This allows for easy association of the received data to the sensors by checking the serial number accompanying the data.

Further, in some instance the serial number of each sensor is further associated with the patient. Accordingly, even the raw data received from the sensors can be associated with the correct patient. In that regard, the serial number is used to access patient data in some embodiments. For example, patient data such as prior diagnoses, prior treatments, height, weight, blood pressure, etc. can be provided to the medical personnel treating the patient. In other instances, previous diagnostic studies and/or data sets from the sensors can be provided to the medical personnel treating the patient. In that regard, the prior data sets are compared to the current data sets in some instances. In some instances, the serial number is associated with a patient, but all private information regarding the patient is disassociated from the serial number. For example, the serial number may be associated with the general characteristics of the patient (such as age, height, weight, medical condition, treatment plan, etc.), but private information (such as the patient's name, address, social security number, etc.) are not associated with the serial number. Accordingly, the sensors are utilized in some embodiments for providing data without any personal information to a database for later use. Such a system could be utilized to streamline referrals, reduce costs, and/or generally improve patient care. In some embodiments, the sensors are utilized in an ER or other situation where the treating medical personnel knows nothing or very little about the patient and the patient's primary care physician is unavailable. The data associated with the sensor can be utilized to provide additional information to the medical personnel that may be crucial in determining the appropriate treatment options for the patient in the emergency.

Generally, the data collected from the various sensors is used to monitor the effectiveness (or lack thereof) of the treatment, modify the treatment plan, monitor the position of an implanted device, and/or otherwise monitor the anatomical area of interest. The data from the sensors can be stored in a database for analysis and consideration in later patient treatments. In some instances the data is utilized to refine the design of the device or implant. For example, understanding forces exerted on a device and the resulting pressure concentrations within the device may permit design changes that can reduce the weight of the implant and/or localize material strength though material selection or material thickness.

In some instances, one or more of the sensors positioned within the device 520 are selectively activated and de-activated. In some embodiments, the device 520 is reprogrammable such that the active sensors can be changed or modified. In that regard, allowing the device 520 to be reprogrammed multiple times can extend sensor life, improve data exchange efficiency, and/or minimize power consumption.

Figure 32:
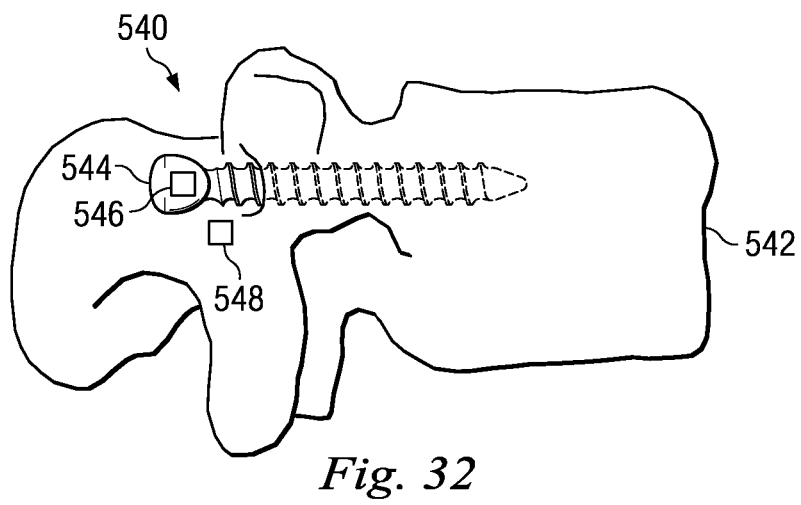
FIG. 32 is a diagrammatic side view of a system for monitoring implant loosening according to one embodiment of the present disclosure.

Referring now to FIG. 32, shown therein is a system 540 for monitoring implant loosening according to one embodiment of the present disclosure. A vertebra 542 has been engaged by a bone fixation device 544, as shown. A sensor 546 is positioned within or on the bone fixation device 544. In some instances, the bone fixation device 544 is part of a larger treatment system (not shown). For example, in some instances the bone fixation device 544 is part of a rod and screw system for limiting the motion of vertebrae. In other embodiments, the bone fixation device 544 is utilized as part of a dynamic fixation system. A sensor 548 is positioned adjacent to the bone fixation device 544 and the sensor 546. In some embodiments, the sensor 548 is fixed with respect to the vertebra 542. In that regard, the sensor 548 may itself engage the bone and/or the sensor 548 may be attached or imbedded within a housing that engages to the bone. The sensors 546 and 548 are utilized to monitor and/or detect any loosening of the bone fixation device 544 relative to the vertebra 542.

In that regard, the sensors 546 and 548 are accelerometers in some embodiments. The relative motion of the sensors 546 and 548 with respect to one another is detected. If the motion patterns of the sensors 546 and 548 are substantially similar, then the bone fixation device 544 is substantially fixed with respect to the vertebra. This is because the sensor 546 is fixed with respect to the bone fixation device and the sensor 548 is fixed with respect to the vertebra 542. However, if the motion patterns of the sensors 546 and 548 are divergent, then this can be an indication of loosening of the bone fixation device 544 relative to the vertebra. In that regard, the magnitude of the divergence between the motion patterns of the sensors 546 and 548 can be indicative of the amount or degree of loosening of the bone fixation device 544. In other embodiments, the relative angles of the sensors with respect to one another is monitored. If the fixation device 544 remains substantially fixed to the vertebra 542, then relative angles of the sensors 546 and 548 remains substantially fixed as well. However, if the fixation device 544 has loosened, then the fixation device may toggle with respect to the vertebra 542 and the relative angles of the sensors 546 and 548 will change. Accordingly, the relative angles of the sensors 546 and 548 are utilized in some embodiments to detect loosening. In some instances, the degree of loosening is monitored over time. The loosening information may be utilized to determine the need for additional treatment and/or revision surgery to correct the loosening. In some embodiments, more than one sensor is fixed relative to the vertebra 542 and/or the fixation device 544. Use of multiple sensors can prevent a false detection of loosening where the sensor itself has become loose for some reason.

Figure 33:
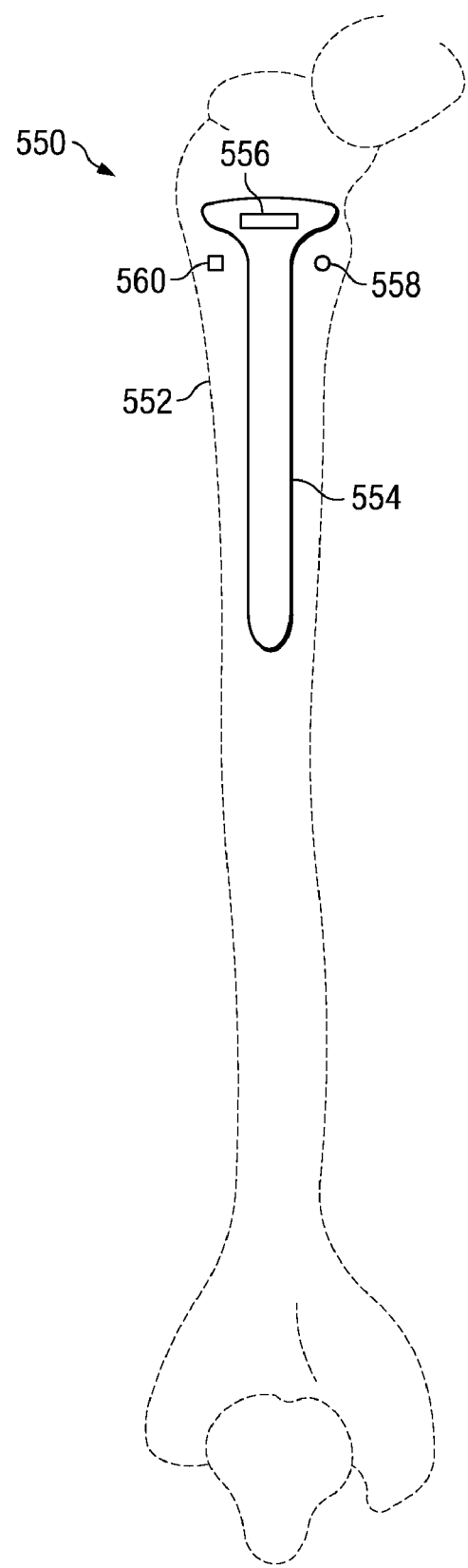
FIG. 33 is a diagrammatic cross-sectional view of a system for monitoring implant loosening according to another embodiment of the present disclosure.

While the detection of loosening has been described with respect to a bone fixation device, similar concepts are utilized for monitoring loosening of other implants, including other fixation devices, prosthetic device, and/or sensors. Further, the detection of loosening is not limited to the spinal region, but is utilized throughout the body where implants are fixed with respect to anatomical features. For example, referring now to FIG. 33, shown therein is a system 550 for monitoring implant loosening according to another embodiment of the present disclosure. In particular, the system 550 illustrates a long bone 552 that has received an implant 554, as shown. In some instances, the implant 554 comprises an intramedullary rod or nail. The implant 554 includes a sensor 556 therein. The bone 552 includes a pair of sensors 558 and 560. As discussed above, the use of multiple sensors—such as sensors 558 and 560—provides a redundancy that helps prevent false detection of implant loosening. In other embodiments, the implant 554 also includes multiple sensors. In some embodiments, the implant 554 includes a sensor proximal to each end of the implant. Generally, the sensors 556, 558, and 560 are utilized to detect loosening of the implant 554 with respect to the bone 552 in a similar manner as described above.

In some instances, the implantable sensors and/or implants including the sensors are in communication with a device or system for remotely communicating data obtained by the sensors to a medical facility or medical personnel. For example, in some instances the implantable sensors and/or implants are configured for communication with a system such as the CARELINK system from Medtronic. In some instances, data from the sensors is transferred to the medical facility or personnel at a regular interval (e.g., once a day, week, or otherwise). In other instances, data from the sensors is transferred to the medical facility or personnel upon the sensors sensing an abnormality or change in one or more of the conditions monitored by the sensors. In some instances, the sensors and/or implants are associated with reservoirs of pharmaceuticals for controlled dispensing depending on the sensed conditions. Such reservoirs are utilized for pain management, to encourage healing, promote tissue growth, or otherwise in some instances. In some instances, one or more devices or methods as described in U.S. patent application Ser. No. 11/217,693 filed Sep. 8, 2006 entitled "Controlled Release Systems and Methods for Osteal Growth," U.S. patent application Ser. No. 11/517,771 filed Sep. 8, 2006 entitled "Controlled Release Devices for Fusion of Osteal Structures," and/or U.S. patent application Ser. No. 11/410,216 filed Sep. 8, 2006 entitled "Controlled Release Systems and Methods for Intervertebral Discs," each of which is incorporated by reference herein in its entirety. In other instances, the implants are adjustable based on the sensed conditions. For example, in some instances the stiffness and/or dampening of an implant is adjusted based on the sensed conditions. In some instances, devices as described in U.S. patent application Ser. No. 12/048,627, filed Mar. 14, 2008 entitled "Intervertebral Implant and Methods of Implantation and Treatment," hereby incorporated by reference in its entirety, are utilized. In some instances, devices similar to those described in PCT/US2005/020116 filed Jun. 8, 2005 entitled "Prosthetic Intervertebral Spinal Disc With Integral Microprocessor," hereby incorporated by reference in its entirety, are utilized.

In one embodiment, a method of patient assessment and outcome modeling comprises: obtaining patient characteristic information from a current patient; defining a plurality of therapeutic factors based on the characteristic information of the current patient; weighting the therapeutic factors; accessing at least one database having medical records of prior patients, the medical records including at least prior patient characteristic information, prior patient treatment plan, and prior patient outcome; comparing the weighted factors of the current patient to the medical records of the prior patients to identify one or more relevant prior patient records; retrieving at least a portion of the relevant prior patient records, the portion including at least the prior patient treatment plan and the prior patient outcome; and performing a simulation of at least one of the prior patient treatment plans based on the current patient's characteristic information.

In some instances, the method further comprises identifying at least one available treatment plan for the current patient. In some instances, the database includes information collected from one or more treatment studies. In some instances, the steps of accessing at least one database, comparing the weighted factors of the current patient to the medical records of the prior patients, retrieving at least a portion of the relevant prior patient records, and performing the simulation are executed electronically. In some instances, the steps of accessing at least one database, comparing the weighted factors of the current patient to the medical records of the prior patients, retrieving at least a portion of the relevant prior patient records, and performing the simulation are executed over a computer network. In some instances, at least one of the steps of accessing at least one database, comparing the weighted factors of the current patient to the medical records of the prior patients, retrieving at least a portion of the relevant prior patient records, and performing the simulation is executed remotely over a computer network. In some instances, at least two available treatment plans are identified and further comprising ranking the at least two available treatment plans. In some instances, the method further comprises performing a simulation of the at least two available treatment plans, where the ranking is at least partially based on the simulations. In some instances, the ranking is at least partially based on the success of the available treatment plans for the one or more relevant prior patient records. In some instances, the prior treatments and the administered treatments include a spinal surgical procedure. In some instances, the patient characteristic information includes patient characteristic information obtained from diagnostic tests.

In one embodiment, a system for pathology assessment, treatment, and outcome modeling comprises: a database having a plurality of records of prior patients, the records including patient characteristic information, treatment information, and outcome information; and at least one processing system operatively connected to the database, the at least one processing system comprising a diagnosis module, a modeling module, and a treatment module; where the diagnosis module is configured to receive and weight current patient information, compare the current patient information to the plurality of records of the database, and retrieve records of prior patients with similar characteristic information from the database, the treatment module is configured to identify available treatment options for the current patient, and the modeling module is configured to simulate the available treatment options for the current patient, wherein the simulation is at least partially based on the outcome information from the records of prior patients. In some instances, the diagnosis module is configured to monitor the outcome of a treatment of the current patient. In some instances, the database is remote from at least one of the diagnosis module, the modeling module, and the treatment module.

In one embodiment, a method for patient assessment and outcome prediction comprises: obtaining a plurality of therapeutic factors from a current patient, said factors based at least partially on the current patient's physical characteristics, pathology, and desired therapeutic outcomes; weighting the therapeutic factors; accessing at least one database having records of prior patient treatments, including prior patient therapeutic factors, treatment plans, and treatment outcomes; comparing the therapeutic factors of the current patient with the prior patient therapeutic factors in the records of the database to identify prior patients with similar therapeutic factors; retrieving from the database at least a portion of one or more records of prior patients with similar therapeutic factors; identifying one or more available treatment plans for the current patient based at least in part on the records of the prior patients with similar therapeutic factors; and predicting a likelihood of success for each of the one or more available treatment plans for the current patient.

In some instances, the available treatment plans are identified based on the success of the treatment plans with prior patients with similar therapeutic factors. In some instances, method further comprises simulating the one or more available treatment plans based on the current patient's physical characteristics, pathology, and desired therapeutic outcomes. In some instances, the method further comprises selecting a treatment plan at least partially based on the simulating of the one or more available treatment plans. In some instances, selecting a treatment plan is at least partially based on the treatment outcomes of the prior patients with similar therapeutic factors. In some instances, accessing the at least one database includes accessing the at least one database from a remote location.

In one embodiment, a method for identifying available treatment options for a patient having an increased likelihood of success, comprising: obtaining a plurality of therapeutic factors from a current patient, said factors based at least partially on the current patient's physical characteristics, pathology, and desired therapeutic outcomes; weighting the therapeutic factors; accessing at least one database having records of prior patient treatments, including prior patient therapeutic factors, treatment plans, and treatment outcomes; comparing the therapeutic factors of the current patient with the prior patient therapeutic factors in the records of the database to identify prior patients with similar therapeutic factors; retrieving from the database at least a portion of one or more records of prior patients with similar therapeutic factors; and identifying available treatment options for the current patient based at least in part on the records of the prior patients with similar therapeutic factors.

In some instances, the available treatment options are identified based on the success of the treatment options with prior patients with similar therapeutic factors. In some instances, the method further comprises simulating the one or more available treatment options based on the current patient's physical characteristics, pathology, and desired therapeutic outcomes. In some instances, a specific treatment option is selected from the one or more available treatment options at least partially based on the simulating of the one or more treatment plans. In some instances, the specific treatment option is selected at least partially based on the treatment outcomes of the prior patients with similar therapeutic factors. In some instances, the accessing the at least one database includes accessing from a remote location. In some instances, accessing the at least one database is executed remotely over a computer network. In some instances, the method further comprises ranking the available treatment options. In some instances, the ranking is at least partially based on simulating the available treatment options. In some instances, the ranking is at least partially based on the prior patient outcomes. In some instances, the patient characteristic information includes patient characteristic information obtained from diagnostic tests. In some instances, the diagnostic tests include imaging.

In one embodiment, a system for identifying available treatment options for a current patient having an increased likelihood of success comprises: at least one local database having a plurality of records of prior local patients, the records including patient characteristic information, treatment information, and outcome information; at least one remote database having a plurality of records of prior remote patients, the records including patient characteristic information, treatment information, and outcome information; at least one processing system operatively connected to the local and remote databases, the at least one processing system comprising a diagnostic module, a modeling module, and a treatment module; where the diagnostic module is configured to receive and weight current patient information, compare the current patient information to the plurality of records of in the local and remote databases, and retrieve records of prior patients with similar characteristic information from the local and remote databases, the treatment module is configured to identify available treatment options for the current patient based at least partially on the records retrieved from the local and remote databases by the diagnostic module, and the modeling module is configured to simulate the available treatment options for the current patient identified by the treatment module, wherein the simulation is at least partially based on the outcome information from the records of prior patients retrieved from the local and remote databases. In some instances, the treatment information stored in the local and remote databases includes medical products used in the treatment. In some instances, the processing system is operatively connected to the local database in order to store current patient information in the local database. In some instances, the local database is at least partially accessible by a remote processing system. In some instances, private information stored in the local database is not accessible by a remote processing system.

In one embodiment, a method for identifying available treatment options comprises: accessing at least one database having records of prior patients, including prior patient treatment plans and treatment outcomes; identifying prior patients with similar characteristics to a current patient; retrieving from the database at least a portion of the records of prior patients with similar characteristics to the current patient, the portion of the records including the treatment plans and treatment outcomes; and identifying successful treatment plans of prior patients based on the treatment outcomes. In some instances, the method further comprises modeling the successful treatment plans identified based on the current patient's characteristics. In some instances, the method further comprises ranking the successful treatment plans at least partially based on the modeling.

In one embodiment, a method of obtaining and analyzing patient information for diagnosis and treatment comprises: identifying at least one patient symptom; selecting at least one patient category associated with the at least one patient symptom; obtaining data corresponding to the at least one patient category; providing the obtained data to a software application; analyzing the obtained data with the software application; and providing a summary of the software application analysis for use in diagnosing the patient's medical condition and identifying available treatment options.

In some instances, selecting the at least one patient category comprises selecting a patient category from a predefined set of patient categories. In some instances, each patient category of the predefined set of patient categories includes an associated data collection set that defines a plurality of data items corresponding to the patient category. In some instances, obtaining data corresponding to the at least one patient category comprises performing a diagnostic test. In some instances, obtaining data corresponding to the at least one patient category comprises asking the patient a series of questions. In some instances, obtaining data corresponding to the at least one patient category comprises obtaining data from a previous medical exam. In some instances, the data from the previous medical exam is provided by a referring medical institution. In some instances, the method further comprises comparing the summary to a prior patient data set to identify previously successful treatment plans of prior patients in a similar patient category. In some instances, the method further comprises modeling the previously successful treatment plans based on the at least one patient symptom. In some instances, the method further comprises selecting a treatment plan for the current patient based at least partially the comparison. In some instances, the selected treatment plan is a previously successful treatment plan of a prior patient in a similar patient category.

In one embodiment, a method of obtaining and analyzing patient information for diagnosis and treatment comprises: submitting a patient to diagnostic testing; obtaining results from the diagnostic testing; categorizing the patient based on the results from the diagnostic testing; obtaining additional data regarding the patient, the data being associated with the categorization of the patient; providing the obtained data and the results from the diagnostic testing to a software application; analyzing the obtained data and results from the diagnostic testing with the software application; and identifying at least one available treatment option for the patient based on the analysis.

In some instances, submitting the patient to diagnostic testing includes imaging. In some instances, analyzing the data and results comprises creating a model of a portion of the patient's anatomy. In some instances, identifying at least one available treatment option comprises simulating the at least one treatment option within the model. In some instances, identifying at least one available treatment option further comprises identifying successful treatment options of previous patients with a similar categorization. In some instances, categorizing the patient comprises selecting a category from a predefined set of categories. In some instances, categorizing the patient is performed by a computer system based on the results of the diagnostic testing. In some instances, obtaining additional data regarding the patient comprises performing additional diagnostic tests. In some instances, providing the obtained data and the results from the diagnostic testing to the software application comprises sending the data and results over a computer network.

In one embodiment, a method of visualizing and analyzing anatomical motion comprises: providing a plurality of implantable sensors, each sensor configured for implantation adjacent to an anatomical feature of a patient; tracking the positions of the implantable sensors as the patient is put through a diagnostic motion protocol; correlating the positions of the implantable sensors to the positions of the anatomical features of the patient adjacent to the sensors; visualizing a motion sequence of the anatomical features according to the positions of the anatomical features from the diagnostic motion protocol; and analyzing the motion sequence of the anatomical features to identify a medical problem.

In some instances, tracking the positions of the implantable sensors comprises using wireless telemetry communication between the sensors and at least one receiver. In some instances, the positions of the implantable sensors are determined by triangulation. In some instances, tracking the positions of the implantable sensors comprises monitoring the relative movement between the sensors. In some instances, the relative movement between the sensors is monitored by comparing accelerometer data from the sensors. In some instances, the method further comprises securely attaching each of the implantable sensors to a portion of the adjacent anatomical feature. In some instances, securely attaching the implantable sensor comprises threadingly engaging a housing of the sensor with a bone. In some instances, visualizing the motion sequence of the anatomical features comprises creating an animated model of the anatomical features. In some instances, analyzing the motion sequence comprises comparing the animated model to a standardized model to identify an abnormality in the motion sequence. In some instances, the method further comprises correlating the abnormality in the motion sequence to identify the medical problem. In some instances, the method further comprises imaging the patient with the sensors implanted. In some instances, the method further comprises determining a relative orientation between each of the implantable sensors and each of the adjacent anatomical features based on the imaging. In some instances, the method further comprises using the imaging and relative orientations to create an initial model of the patient's anatomical features. In some instances, the method further comprises updating the model based on the positions of the anatomical features from the diagnostic motion protocol.

In one embodiment, a system for visualizing and analyzing anatomical motion comprises: a plurality of implantable sensors, each sensor configured for implantation adjacent to an anatomical feature of a patient; a monitoring system in communication with the implantable sensors, the monitoring system configured to track the positions of the sensors within the patient during a diagnostic motion protocol; at least one processing system in communication with the monitoring system, the at least one processing system comprising a modeling module configured to create an animated model of the patient's anatomical features based at least partially on the positions of the sensors as tracked by the monitoring system during the diagnostic motion protocol.

In some instances, each of the plurality of implantable sensors are configured for engagement with a bone structure. In some instances, the system further comprises an imaging device in communication with the at least one processing system, wherein the animated model is at least partially based on data obtained by the imaging device. In some instances, each of the plurality of sensors comprises an asymmetrical profile such that an orientation of the sensor with respect to the adjacent anatomical feature is detectable by the imaging device. In some instances, the monitoring system comprises a wireless telemetry receiver system configured for communication with the plurality of implantable sensors. In some instances, the monitoring system comprises a plurality of receivers and is configured to determine the positions of the sensors via triangulation.

In one embodiment, a method of performing a surgical procedure using implantable sensors comprises: providing one or more implantable sensors, each sensor configured for implantation adjacent to an anatomical feature of a patient; imaging the patient to determine the relative positions of the one or more implantable sensors relative to the anatomical features of the patient; inserting an implant adjacent to at least one of the anatomical features; and tracking the position of the implant relative to the at least one anatomical feature during the inserting of the implant using the implantable sensors.

In some instances, at least one of the anatomical features is a vertebra. In some instances, at least one of the implantable sensors comprises a housing having a bone engaging portion. In some instances, at least one of the implantable sensors comprises an asymmetrical profile such that an orientation of the sensor with respect to the adjacent anatomical feature is detectable from the imaging. In some instances, the implant includes a sensor therein and wherein tracking the position of the implant comprises tracking the relative position of the sensor within the implant to at least one of the implantable sensors. In some instances, inserting the implant comprises grasping the implant with a surgical tool. In some instances, the surgical tool includes a sensor therein and wherein tracking the position of the implant comprises tracking the relative position of the sensor within the surgical tool to at least one of the implantable sensors. In some instances, tracking the position of the implant comprises visually monitoring the insertion of the implant. In some instances, the method further comprises monitoring the position of the implant relative to the at least one anatomical feature using the implantable sensors after insertion of the implant. In some instances, the implant comprises a spinal implant. In some instances, the implant comprises an artificial disc. In some instances, tracking the position of the implant relative to the at least one anatomical feature comprises tracking the relative position of a sensor associated with the implant to at least one of the plurality of implantable sensors. In some instances, the sensor associated with the implant is positioned within the implant. In some instances, the sensor associated with the implant is positioned in a surgical tool for inserting the implant. In some instances, the implant is inserted using an image-guided system.

In one embodiment, a method of inserting a spinal implant comprises: providing at least one sensor, the at least one sensor being positioned within a housing having a bone engaging portion and an asymmetrical head portion; engaging the bone engaging portion of the housing with a vertebra; imaging the patient to determine the relative position of the sensor relative to the vertebra using the asymmetrical head portion of the housing as a guide; inserting an implant adjacent to the vertebra; and tracking the position of the implant relative to the vertebra by correlating the relative position of the implant to the sensor to the vertebra. In some instances, the implant includes a sensor therein and wherein tracking the position of the implant comprises tracking the position of the sensor within the implant relative to the sensor positioned within the housing. In some instances, inserting the implant comprises using a surgical tool to guide the implant to a position adjacent to the vertebra, the implant having a fixed relationship with respect to the surgical tool when engaged with the surgical tool. In some instances, the surgical tool includes a sensor therein and tracking the position of the implant comprises tracking the position of the sensor positioned within the surgical tool relative to the sensor positioned within the housing. In some instances, the surgical tool is part of an image-guided system.

In one embodiment, a method of selecting implant parameters comprises: introducing one or more sensors adjacent to an anatomical feature; monitoring a motion sequence of the anatomical feature with the one or more sensors; analyzing the monitored motion sequence of the anatomical feature to detect a problem in the motion sequence of the anatomical feature; and determining a parameter for an implant for at least partially correcting the problem in the motion sequence of the anatomical feature. In some instances, the method further comprises monitoring the motion sequence of the anatomical feature with the one or more sensors after implantation of the implant. In some instances, the method further comprises: analyzing the monitored motion sequence of the anatomical feature after implantation of the implant to detect a remaining problem in the motion sequence of the anatomical feature; and determining a modification of at least one parameter of the implant to at least partially correct the remaining problem in the motion sequence of the anatomical feature.

In some instances, monitoring the motion sequence comprises tracking a position of the one or more sensors. In some instances, monitoring the motion sequence comprises tracking a position of the one or more sensors with respect to another of the one or more sensors. In some instances, introducing one or more sensors adjacent to an anatomical feature comprises implanting the one or more sensors. In some instances, analyzing the monitored motion sequence of the anatomical feature comprises utilizing a computer system. In some instances, utilizing the computer system comprises creating an animated model of the motion sequence. In some instances, detecting the problem in the motion sequence comprises comparing the animated model of the motion sequence to a standardized model. In some instances, the anatomical feature is a spinal joint. In some instances, introducing one or more sensors comprises securing the one or more sensors to at least one vertebra. In some instances, the method further comprises identifying one or more spinal implants for at least partially correcting the detected problem in the motion sequence of the spinal joint. In some instances, at least one of the one or more spinal implant is adjustable such that at least one parameter of the spinal implant is modifiable. In some instances, the method further comprises modifying the at least one parameter of the adjustable spinal implant to substantially match the determined parameter for correcting the problem in the motion sequence of the anatomical feature.

In one embodiment, a method of selecting a spinal implant and its parameters comprises: introducing a plurality of sensors adjacent to a pair of vertebrae defining a spinal joint; monitoring a motion sequence of the spinal joint with the plurality of sensors; analyzing the monitored motion sequence of the vertebrae to detect an initial problem in the motion sequence of the spinal joint; determining a parameter for an implant for correcting the initial problem in the motion sequence of the spinal joint; identifying at least one spinal implant with the parameter for correcting the initial problem in the motion sequence of the spinal joint.

In some instances, the method further comprises monitoring the motion sequence of the spinal joint after implantation of a spinal implant with the parameter for correcting the problem in the motion sequence of the joint to detect a remaining problem in the motion sequence of the spinal joint. In some instances, monitoring the motion sequence of the spinal joint after implantation comprises monitoring the motion sequence with at least one sensor positioned within the spinal implant. In some instances, monitoring the motion sequence of the spinal joint after implantation comprises monitoring the motion sequence with the plurality of sensors. In some instances, the method further comprises determining a factor for an implant for correcting the remaining problem in the motion sequence of the spinal joint; and identifying at least one spinal implant with the factor for correcting the remaining problem in the motion sequence of the spinal joint. In some instances, identifying the at least one spinal implant with the factor for correcting the remaining problem comprises identifying a modification to the spinal implant with the parameter for correcting the initial problem in the motion sequence of the spinal joint.

In one embodiment, a method of detecting implant loosening comprises: providing an implant for fixedly engaging with an anatomical feature of a patient, the implant having a first sensor secured thereto; tracking a first motion pattern of the first sensor; tracking a second motion pattern of a second sensor secured to the anatomical feature; determining a relative motion between the first sensor and the second sensor based on the first and second motion patterns; and identifying implant loosening by analyzing the relative motion between the first sensor and the second sensor.

In some instances, identifying implant loosening comprises identifying differences between the first motion pattern and the second motion pattern. In some instances, a magnitude in the differences between the first motion pattern and the second motion pattern is indicative of the degree of loosening. In some instances, determining a relative motion between the first and second sensors comprising monitoring the relative angle of the first sensor to the second sensor. In some instances, identifying implant loosening comprises identifying a change in the relative angle of the first sensor to the second sensor indicative of implant loosening. In some instances, the implant is for fixedly engaging with a bone. In some instances, the first sensor secured to the implant is embedded within the implant. In some instances, the implant is a spinal prosthetic. In some instances, the implant is a fixation device. In some instances, the implant is configured for insertion into an intramedullary canal of a long bone. In some instances, the first and second sensors comprise accelerometers.

In one embodiment, a method of detecting implant loosening comprises: inserting a first sensor into a bone structure; securing the first sensor in a fixed position with respect to the bone structure; engaging an implant with at least a portion of the bone structure, the implant having a second sensor positioned therein; securing the implant with the portion of the bone structure such that the second sensor is substantially fixed with respect to the bone structure and the first sensor; and monitoring the position of the second sensor with respect to the first sensor to identify implant loosening.

In some instances, monitoring the position of the second sensor with respect to the first sensor comprises monitoring the relative angle of the second sensor to the first sensor. In some instances, a change in the angle between the second sensor and first sensor is indicative of implant loosening. In some instances, monitoring the position of the second sensor with respect to the first sensor comprises monitoring motion patterns of the first and second sensors. In some instances, a difference between the motion patterns of the first and second sensors is indicative of implant loosening. In some instances, inserting the first sensor into the bone structure comprises engaging a housing of the first sensor with a vertebra. In some instances, engaging the implant with at least a portion of the bone structure comprises inserting a spinal implant. In some instances, the steps of inserting and securing the first sensor comprise positioning the first sensor within a portion of a long bone. In some instances, engaging the implant with at least a portion of the bone structure comprises inserting an elongated implant into an intramedullary canal of the long bone.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure. Further, while numerous embodiments have been described it is fully contemplated that steps from various methods may be combined and components from various devices and systems may be combined, even if not explicitly described herein.

What is claimed is:

1. A method of patient assessment and outcome modeling, comprising:

obtaining, using a processor, patient characteristic information associated with a current patient, wherein said obtaining operation includes:

identifying at least one patient symptom, selecting at least one patient category from a predefined set of patient categories associated with the at least one patient symptom, and depending on the selected category, obtaining the patient characteristic information corresponding to the at least one patient category, defining, using the processor, one or more desirable outcome factors based on the characteristic information of the current patient;

weighting, using the processor, the one or more desirable outcome factors;

accessing, using the processor, at least one database having medical records of prior patients, the medical records including at least prior patient characteristic information, prior patient treatment plan, and prior patient outcome;

comparing, using the processor, the weighted factors of the current patient to the medical records of the prior patients to identify one or more prior patient records relevant to the patient characteristic information of the current patient;

retrieving, using the processor, at least a portion of the relevant prior patient records, the portion including at least the prior patient treatment plan and the prior patient outcome; and performing, using the processor, a simulation of at least one of the prior patient treatment plans based on the current patient's characteristic information.

2. The method of claim 1, further comprising identifying at least two available treatment plans for the current patient and ranking the at least two available treatment plans.

3. The method of claim 2, further comprising performing a simulation of the at least two available treatment plans and wherein the ranking is at least partially based on the simulations.

4. The method of claim 3, wherein the ranking is at least partially based on the success of the available treatment plans for the one or more relevant prior patient records.

5. The method of claim 4, wherein said prior treatments and said available treatments include a spinal surgical procedure.

6. The method of claim 5, further comprising:
selecting one of the at least two available treatment plans;
performing the selected treatment plan;
comparing one or more actual outcome factors to the one or more desirable outcome factors; and
updating the at least one database with a medical record of the current patient, including at least the selected treatment plan and the one or more actual outcome factors.

7. A method for identifying available treatment options for a patient having an increased likelihood of success, comprising:
obtaining, using a processor, a plurality of therapeutic factors associated with a current patient, said factors based at least partially on the current patient's physical characteristics, pathology, and desired therapeutic outcomes, wherein said obtaining operation includes:
identifying at least one patient symptom,
selecting at least one patient category from a predefined set of patient categories associated with the at least one patient symptom, and
depending on the selected category, obtaining the plurality of therapeutic factors corresponding to the at least one patient category;
weighting, using the processor, the therapeutic factors;
accessing, using the processor, at least one database having records of prior patient treatments, including prior patient therapeutic factors, treatment plans, and treatment outcomes;
comparing, using the processor, the weighted therapeutic factors of the current patient with the prior patient therapeutic factors in the records of the database to identify prior patients with similar therapeutic factors;

retrieving, using the processor, from the database at least a portion of one or more records of prior patients with similar therapeutic factors; and identifying, using the processor, available treatment options for the current patient based at least in part on the records of the prior patients with similar therapeutic factors.

8. The method of claim 7, wherein the available treatment options are identified based on the success of the treatment options with prior patients with similar therapeutic factors.

9. The method of claim 8, further comprising simulating the one or more available treatment options based on the current patient's physical characteristics, pathology, and desired therapeutic outcomes.

10. The method of claim 9, wherein a specific treatment option is selected from the one or more available treatment options at least partially based on the simulating of the one or more treatment plans.

11. The method of claim 10, wherein the specific treatment option is selected at least partially based on the treatment outcomes of the prior patients with similar therapeutic factors.

12. The method of claim 11, further comprising ranking the available treatment options.

13. The method of claim 12, wherein the ranking is at least partially based on simulating the available treatment options.

14. The method of claim 13, wherein the ranking is at least partially based on the prior patient outcomes.

15. The method of claim 7, further comprising:
analyzing the obtained patient characteristic information corresponding to the at least one patient category; and
providing a summary of the analysis, wherein the summary includes data related to the current patient's medical condition and available treatment options.

16. The method of claim 7, wherein each patient category of the predefined set of patient categories includes an associated data collection set that defines a plurality of data items corresponding to the patient category.

17. The method of claim 16, wherein said comparing operation further includes comparing the summary to a prior patient data set to identify previously successful treatment plans of prior patients in a similar patient category.

18. A system for identifying available treatment options for a current patient having an increased likelihood of success, comprising:
at least one local database storage device storing a plurality of records of prior local patients, the records including patient characteristic information, treatment information, and outcome information;
at least one remote database storage device storing a plurality of records of prior remote patients, the records including patient characteristic information, treatment information, and outcome information; and
at least one processing system operatively connected to the local and remote database storage devices, the at least one processing system comprising a computer-readable medium including computer-executable instructions related to a diagnostic module, a modeling module, and a treatment module, and a processor that causes:
the diagnostic module to receive and weight current patient information, compare the current patient information to the plurality of records of in the local and remote databases, and retrieve records of prior patients with similar characteristic information from the local and remote databases, wherein to receive the current patient information, the diagnostic module is configured to:

identify at least one patient symptom, select at least one patient category from a predefined set of patient categories associated with the at least one patient symptom, and depending on the selected category, obtain the current patient information corresponding to the at least one patient category, the treatment module to identify available treatment options for the current patient based at least partially on the records retrieved from the local and remote databases by the diagnostic module, and the modeling module to simulate the available treatment options for the current patient identified by the treatment module, wherein the simulation is at least partially based on the outcome information from the records of prior patients retrieved from the local and remote databases.

19. The system of claim 18, wherein the treatment information stored in the local and remote database storage devices includes medical products used in the treatment.

* * * * *